(12) United States Patent
Bonas et al.

(10) Patent No.: US 10,590,175 B2
(45) Date of Patent: *Mar. 17, 2020

(54) MODULAR DNA-BINDING DOMAINS AND METHODS OF USE

(71) Applicants: Ulla Bonas, Halle (DE); Jens Boch, Wunstorf (DE); Sebastian Schornack, Cambridge (GB); Thomas Lahaye, Mossingen (DE)

(72) Inventors: Ulla Bonas, Halle (DE); Jens Boch, Wunstorf (DE); Sebastian Schornack, Cambridge (GB); Thomas Lahaye, Mossingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/724,420

(22) Filed: Oct. 4, 2017

(65) Prior Publication Data
US 2018/0141979 A1 May 24, 2018

Related U.S. Application Data

(60) Division of application No. 15/222,498, filed on Jul. 28, 2016, now Pat. No. 9,809,628, which is a division of application No. 14/625,698, filed on Feb. 19, 2015, now Pat. No. 9,453,054, which is a continuation of application No. 14/153,241, filed on Jan. 13, 2014, now Pat. No. 9,017,967, which is a continuation of application No. 13/755,826, filed on Jan. 31, 2013, now abandoned, which is a continuation of application No. 13/019,526, filed on Feb. 2, 2011, now abandoned, which is a continuation-in-part of application No. 13/016,297, filed on Jan. 28, 2011, now Pat. No. 9,353,378, which is a continuation of application No. PCT/IB2010/000154, filed on Jan. 12, 2010.

(60) Provisional application No. 61/225,043, filed on Jul. 13, 2009.

(30) Foreign Application Priority Data

Jan. 12, 2009 (DE) .................... 10 2009 004 659
Jul. 13, 2009 (EP) .................... 09165328

(51) Int. Cl.
| | | |
|---|---|---|
| *C07K 14/195* | (2006.01) | |
| *C12N 15/10* | (2006.01) | |
| *C12N 15/82* | (2006.01) | |
| *C12Q 1/6816* | (2018.01) | |
| *G01N 33/53* | (2006.01) | |
| *C12N 1/20* | (2006.01) | |
| *C12N 5/04* | (2006.01) | |
| *C12N 5/071* | (2010.01) | |
| *C07K 14/00* | (2006.01) | |
| *C07H 21/04* | (2006.01) | |

(52) U.S. Cl.
CPC .......... *C07K 14/195* (2013.01); *C07H 21/04* (2013.01); *C07K 14/001* (2013.01); *C12N 1/20* (2013.01); *C12N 5/04* (2013.01); *C12N 5/0602* (2013.01); *C12N 15/1034* (2013.01); *C12N 15/825* (2013.01); *C12N 15/8216* (2013.01); *C12N 15/8217* (2013.01); *C12N 15/8238* (2013.01); *C12N 15/8239* (2013.01); *C12N 15/8279* (2013.01); *C12Q 1/6816* (2013.01); *G01N 33/5308* (2013.01); *C07K 2319/09* (2013.01); *C07K 2319/60* (2013.01); *C07K 2319/80* (2013.01); *C12N 2501/998* (2013.01); *C12Q 2563/119* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |

(Continued)

FOREIGN PATENT DOCUMENTS

| | | |
|---|---|---|
| EP | 0 242 246 | 10/1987 |
| EP | 2 206 723 A1 | 7/2010 |

(Continued)

OTHER PUBLICATIONS

Boch, J., et al., "Breaking the Code of DNA Binding Specificity of TAL-Type III Effectors," *Science*, 2009, vol. 326(5959), pp. 1509-1512.

Boch, J., et al., "*Xanthomonas* AvrBs3 Family-type III Effectors: Discovery and Function," *Annu. Rev. Phytopathol.*, 2010, vol. 48, pp. 20.1-20.18.

Boch, et al., "Breaking the code of DNA binding specificity of TAL-type III efectors," *Science*, 2009, vol. 326(5959), pp. 1509-1512.

(Continued)

*Primary Examiner* — Addison D Ault
(74) *Attorney, Agent, or Firm* — David M. Saravitz; Williams Mullen

(57) ABSTRACT

The present invention refers to methods for selectively recognizing a base pair in a DNA sequence by a polypeptide, to modified polypeptides which specifically recognize one or more base pairs in a DNA sequence and, to DNA which is modified so that it can be specifically recognized by a polypeptide and to uses of the polypeptide and DNA in specific DNA targeting as well as to methods of modulating expression of target genes in a cell.

9 Claims, 46 Drawing Sheets

Specification includes a Sequence Listing.

(56) References Cited

U.S. PATENT DOCUMENTS

| | | | |
|---|---|---|---|
| 5,276,268 | A | 1/1994 | Strauch et al. |
| 5,356,802 | A | 10/1994 | Chandrasegaran |
| 5,436,150 | A | 7/1995 | Chandrasegaran |
| 5,487,994 | A | 1/1996 | Chandrasegaran |
| 5,501,967 | A | 3/1996 | Offringa et al. |
| 5,538,880 | A | 7/1996 | Lundquist et al. |
| 5,554,798 | A | 9/1996 | Lundquist et al. |
| 5,561,236 | A | 10/1996 | Leemans et al. |
| 5,591,616 | A | 1/1997 | Hiei et al. |
| 5,767,366 | A | 6/1998 | Sathasivan et al. |
| 5,792,640 | A | 8/1998 | Chandrasegaran |
| 5,879,903 | A | 3/1999 | Strauch et al. |
| 5,928,937 | A | 7/1999 | Kakefuda et al. |
| 6,084,155 | A | 7/2000 | Volrath et al. |
| 6,326,166 | B1 | 12/2001 | Pomerantz et al. |
| 6,329,571 | B1 | 12/2001 | Hiei |
| 6,368,227 | B1 | 4/2002 | Olson |
| 6,451,732 | B1 | 9/2002 | Beckett et al. |
| 6,451,735 | B1 | 9/2002 | Ottaway et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,001,768 | B2 | 2/2006 | Wolffe |
| 7,013,219 | B2 | 3/2006 | Case et al. |
| 7,070,934 | B2 | 7/2006 | Cox, III et al. |
| 7,163,824 | B2 | 1/2007 | Cox, III et al. |
| 7,220,719 | B2 | 5/2007 | Case et al. |
| 7,262,054 | B2 | 8/2007 | Jamieson et al. |
| 7,273,923 | B2 | 9/2007 | Jamieson et al. |
| 7,285,416 | B2 | 10/2007 | Choo et al. |
| 7,361,635 | B2 | 4/2008 | Miller et al. |
| 7,521,241 | B2 | 4/2009 | Choo et al. |
| 7,842,489 | B2 | 11/2010 | Arnould et al. |
| 2001/0016956 | A1 | 8/2001 | Ward et al. |
| 2005/0064474 | A1 | 3/2005 | Umov et al. |
| 2005/0222012 | A1 | 10/2005 | Hemmenway |
| 2007/0141038 | A1 | 6/2007 | Choulika et al. |
| 2009/0133158 | A1 | 5/2009 | Lahaye et al. |
| 2009/0271881 | A1 | 10/2009 | Arnould et al. |
| 2009/0305402 | A1 | 12/2009 | Liljedahl et al. |
| 2010/0132069 | A1 | 5/2010 | Lahaye et al. |
| 2010/0218264 | A1 | 8/2010 | Cui et al. |
| 2011/0041195 | A1 | 2/2011 | Doyon et al. |
| 2011/0207221 | A1 | 2/2011 | Cost et al. |
| 2011/0265198 | A1 | 4/2011 | Gregory et al. |
| 2011/0301073 | A1 | 5/2011 | Gregory et al. |
| 2011/0129898 | A1 | 6/2011 | Doyon |
| 2011/0136895 | A1 | 6/2011 | Gregory et al. |
| 2011/0145940 | A1 | 6/2011 | Voytas et al. |
| 2011/0158957 | A1 | 6/2011 | Bonini et al. |
| 2011/0167521 | A1 | 7/2011 | DeKelver et al. |
| 2011/0287545 | A1 | 7/2011 | Cost et al. |
| 2011/0201055 | A1 | 8/2011 | Doyon et al. |
| 2011/0201118 | A1 | 8/2011 | Yang et al. |
| 2011/0203012 | A1 | 8/2011 | Dotson et al. |
| 2011/0247089 | A1 | 10/2011 | Doyon et al. |
| 2011/0269234 | A1 | 11/2011 | Doyon et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2012/0246764 | A1 | 9/2012 | Hlubek et al. |
| 2012/0284877 | A1 | 11/2012 | Hlubek et al. |
| 2012/0324603 | A1 | 12/2012 | Hlubek et al. |

FOREIGN PATENT DOCUMENTS

| | | |
|---|---|---|
| EP | 2 392 208 A1 | 12/2011 |
| WO | WO 94/18313 A1 | 8/1994 |
| WO | WO 95/09233 A1 | 4/1995 |
| WO | WO 2007/060495 A1 | 5/2007 |
| WO | WO 2009/095793 A1 | 8/2009 |
| WO | WO 2010/079430 A1 | 7/2010 |
| WO | WO 2011/002503 A1 | 1/2011 |
| WO | WO 2011/017293 A2 | 2/2011 |
| WO | WO 2011/019385 | 2/2011 |
| WO | WO 2011/072246 A2 | 6/2011 |
| WO | WO 2011/100058 | 8/2011 |
| WO | WO 2011/146121 | 11/2011 |
| WO | WO 2011/154393 A1 | 12/2011 |

OTHER PUBLICATIONS

Bogdanove, A., et al., "TAL effectors: finding plant gens for disease and defense," *Current Opinion in Plant Biology*, 2010, vol. 13, pp. 394-401.

Bonas, U., et al., "Resistance in tomato to *Xanthomonas campestris* pv *vesicatoria* is determined by alleles of the pepper-specific avirulence gene avrBs3," *Mol Gen Genet*, 1993, vol. 238, pp. 261-269.

Chevalier, B., et al., Design, Activity, and Structure of a Highly Specific Artificial Endonuclease, *Molecular Cell*, 2002, vol. 10, pp. 895-905.

Christian, M., et al., "Targeting DNA Double-Strand Breaks with TAL Effector Nucleases," *Genetics*, 2010, vol. 186, pp. 757-761.

Durai, S., el al., "Survey and Summary—Zinc finger nucleases: custom-designed molecular scissors for genome engineering of plant and mammalian cells." *Nucleic Acids Research*, 2005. vol. 33(18), pp. 5978-5990.

European Search Report for EP 09165328.7-2403, dated Jan. 12, 2009 (6 pages).

First Examination Report for Australia Patent Application No. 2010204105, dated 2012, 2 pages.

Gu, K., et al., "Transcription activator-like type III effector AvrXa27 depends on OsTFIIA γ5 for the activation of Xa27 transcription in rice that triggers disease resistance to *Xanthomonas oryzae* pv. *oryzae*," *Molecular Plant Pathology*, 2009, vol. 10(6), pp. 829-835.

Gürlebeck, et al., "Dimerization of the bacterial effector protein AvrBs3 in the plant cell cytoplasm prior to nuclear import," *The Plant Journal*, 2005, vol. 42(2), pp. 175-187.

Gürlebeck, et al., "Type III effector proteins from the plant pathogen *Xanthomonas* and their role in the interaction with the host plant," *Journal of Plant Physiology*, 2006, vol. 163(3), pp. 233-255.

Hockemeyer, D., et al., "Genetic engineering of human pluripotent cells using TALE nucleases," *Nature Biotechnology*, 2011, vol. 29(8), pp. 731-734.

Huang, P., et al., "Heritable gene targeting in zebrafish using customized TALENs," 2011, vol. 29(8), pp. 699-700.

Jackel, C., et al., "Protein Design by Directed Evolution," *Annu. Rev. Biophys.*, 2008, vol. 37, pp. 153-173.

Kay, S., et al., "A Bacterial Effector Acts as a Plant Transcription Factor and Induces a Cell Size Regulator," *Science*, 2007, vol. 318(5850), pp. 648-651.

Kay, S., et al., "Detailed analysis of the DNA recognition motifs of the *Xanthomonas* type III effectors AvrBs3 and AvrBs3Δrep16," *The Plant Journal*, 2009, vol. 59, pp. 859-871.

Kay et al., "A bacterial effector acts as a plant transcription factor and induces a cell size regulator," *Science*, 2007, vol. 318(5850), pp. 648-651.

Kay et al., "Detailed analysis of the DNA recognition motifs of the *Xanthomonas* type III effectors AvrBs3 and AvrBs3Δrep16," *Plant Journal*, 2009, vol. 59(6), pp. 859-871.

Kay, S., et al., "Supporting Online Material for "Bacterial Effector Acts as a Plant Transcription Factor and Induces a Cell Size Regulator," *Science*, 2007, vol. 318(5850), pp. 648-651", www.sciencemag.org/cgi/content/full/318/5850/648/DCI, printed May 18, 2012, pp. 1-20.

Li, T., et al., "TAL nucleases (TALNs): hybrid proteins composed of TAL effectors and FokI DNA-cleavage domain," *Nucleic Acids Research*, 2010, Advanced Access, pp. 1-14; 2011, vol. 39(1), pp. 359-372.

Morbitzer, R., et al., "Regulation of selected genome loci using de novo-engineered transcription activator-like effector (TALE)-type transcription factors," *PNAS*, 2010, vol. 107(50), pp. 21617-21622.

Moscou, J., et al., "A Simple Cipher Governs DNA Recognition by TAL Effectors," *Science*, 2009, vol. 326, pp. 1501.

(56) References Cited

OTHER PUBLICATIONS

Römer, P., et al., "A single plant resistance gene promoter engineered to recognize multiple TAL effectors from disparate pathogens," *PNAS*, 2009, vol. 106(48), pp. 20526-20531.
Römer, P. et al., "Promoter elements of rice susceptibility genes are bound and activated by specific TAL effectors from the bacterial blight pathogen, *Xanthomonas oryzae* pv. *oryzae*," *New Phytologist*, 2010, vol. 187, pp. 1048-1057.
Römer, et al., "Plant pathogen recognition mediated by promoter activation of the pepper Bs3 resistance gene," *Science, American Association For The Advancement Of Science, U.S., Washington, DC*, 2007, vol. 318(5850), pp. 645-648.
Römer, et al., "Recognition of AvrBs3-Like Proteins Is Mediated by Specific Binding to Promoters of Matching Pepper Bs3 Alleles," *Plant Physiology*, 2009, vol. 150(4), pp. 1697-1712.
Römer, et al., "A single plant resistance gene promoter engineered to recognize multiple TAL effectors from disparate pathogens," *Proceedings Of The National Academy Of Sciences Of The United Sates Of America*, 2009, vol. 106(48), pp. 20526-20531.
Scholze, H., et al., "'TAL effector-DNA specificity," *Virulence*, 2010, vol. 1(5), pp. 428-432.
Szurek, B., et al., "Type III-dependent translocation of *Xanthomonas* AvrBs3 protein into the plant cell," *Molecular Microbiology*, 2002, vol. 46(1), pp. 13-23.
"Third Party Observations Pursuant to ART. 115 EPC-EP 2 379 583 (Appl.: Bonas, Boch, Schornack, Lahaye)—Title: Modular DNA-binding domains and methods of use," EPO-Munich, 2012, pp. 1/6-6/6.
Townsend, J., et al., "High-frequency modification of plant genes using engineered zinc-finger nucleases," *Nature: International Weekly Journal Of Science*, 2009, vol. 459(7245), pp. 442-445.
Voytas, D., et al., "DNA Binding Made Easy," *Science*, 2009, vol. 326, pp. 1491-1492.
"Written Opinion" for Singapore Application No. 201105017-6, dated 2012, 6 pages.
Yang, B., et al., "The virulence factor AvrXa7 of *Xanthomonas oryzae* pv. *oryzae* is a type III secretion pathway-dependent nuclear-localized double-stranded DNA-binding protein," *PNAS*, 2000, vol. 97(17), pp. 9807-9812.
Zhang, F. et al., "Efficient construction of sequence-specific TAL effectors for modulating mammalian transcription," *Nature Biotechnology*, 2011, vol. 29(2), pp. 149-153.
Zhu, W., et al., "AvrXa10 Contains an Acidic Transcriptional Activation Domain in the Functionally Conserved C Terminus," *MPMI*, 1998, vol. 11(8), pp. 824-832.
Zhu et al., "The C Terminus of AvrXa10 Can Be Replaced by the Transcriptional Activation Domain of VP 16 from the Herpes Simplex Virus," *The Plant Cell*, Sep. 1999, pp. 1665-1674, vol. 11, The American Society of Plant Physiologists.
Mahfouz, Magdy M. et al., "De novo-engineered transcription activator-like effector (TALE) hybrid nuclease with novel DNA binding specificity creates double-strand breaks", Proc. Natl. Acad, Sci. USA, epub Jan. 24, 2011, vol. 108, No. 6, pp. 2623-2628.
NCBI GenBank Accession No. AAT46122, Nov. 12, 2004, 2 pages.
Iowa State University Research Foundation, Inc. et al., PCT/US2011/024515, Notification of Transmittal of the International Search Report and The Written Opinion of the International Searching Authority, or the Declaration, dated Feb. 11, 2011, 7 pages.
Hummel, Poster—"A cipher-like mechanism governs TAL effector-DNA recognition", Jun. 14, 2010.
Alam and Sittman, "Characterization of the cytotoxic effect of a chimeric restriction enzyme, H1°—FokI," Gene Ther. Mol. Biol., 10:147-160, 2006.
Alam, "Characterization of the cytotoxic effect of a novel chimeric restriction nuclease, H1°—FokI, in mouse fibroblast cells: Implications for chromatin mapping and gene therapy studies," Ph.D. Thesis, The University of Mississippi Medical Center, 2006, 227 pages.

Beretta et al., "Tethering a type IB topoisomerase to a DNA site by enzyme fission to a heterologous site-selective DNA-binding protein domain," Cancer Res., 59:3689-3697, 1999.
Carlson et al., "Targeting DNA With Fingers and TALENs", Mol. Ther. Nucl. Acids, 1:e3; doi: 10.1038/mtna.2011.5; published online Jan. 24, 2012.
Fonfara et al., "Creating highly specific nucleases by fusion of active restriction endonucleases and catalytically inactive homing endonucleases," Nucl. Acids Res., 40(2): 847-860, 2011.
Gabriel et al., "An unbiased genome-wide analysis of zinc-finger nuclease specificity," Nat. Biotechnol., 29:816-823, 2011.
Halford et al., "The reaction mechanism of FokI excludes the possibility of targeting zinc finger nucleases to unique DNA sites," Biochem. Soc. Trans., 39:584-588, 2011.
Kim et al., "Construction of a Z-DNA-specific restriction endonuclease," Proc. Natl. Acad. Sci. USA, 94(24):12875-12879, 1997.
Kim et al., "Site-specific cleavage of DNA-RNA hybrids by zinc finger/FokI cleavage domain fusions," Gene, 203(1):43-49, 1997.
Miller et al., "An improved zinc-finger nuclease architecture for highly specific genome editing," Nature Biotechnol., 25:778-785, 2007.
Pattanayak et al., "Revealing off-target cleavage specificities of zinc-finger nucleases by in vitro selection," Nat. Methods, 8:765-770, 2011.
Podhajska and Szybalski, "Conversion of the FokI endonuclease to a universal restriction enzyme: cleavage of phage M13mp7 DNA at predetermined sites," Gene, 40(2-3):175-182, 1985.
Radecke et al., "Zinc-finger nuclease-induced gene repair with oligodeoxynucleotides: wanted and unwanted target locus modifications," Mol. Ther., 18(4):743-753, 2010.
Santiago et al., "Targeted gene knockout in mammalian cells by using engineered zinc-finger nucleases," Proc. Natl. Acad. Sci. USA, 105(15):5809-5814, 2008.
Wah et al., "Structure of FokI has implications for DNA cleavage," Proc. Natl. Acad. Sci. USA, 95(18):10564-10569, 1998.
Wah et al., "Structure of the multimodular endonuclease FokI bound to DNA," Nature, 388(3):97-100, 1997.
Wright et al., "High-frequency homologous recombination in plants mediated by zinc-finger nucleases," Plant J., 44(4):693-705, 2005.
Hummel et al., "Rice gene activation by transcription activator-like effectors of *Xanthomonas oryzae* pvs. *oryzae* and *oryzicola*" (abstract), and "A cipher-like mechanism governs TAL effector-DNA recognition," (poster presentation), XIV International Congress on Molecular Plant-Microbe Interactions, Quebec City, Canada, Jul. 19-23, 2009, 3 pages.
Ledford, "Plant genes get fine tailoring," Nature News [online], Apr. 29, 2009 [retrieved on Jan. 4, 2013]. Retrieved from the Internet: <URL: http://www.nature.com/news/2009/090429/full/news.2009.415.html>, 3 pages.
Pavletich and Pabo, "Zinc finger-DNA recognition: crystal structure of a Zif268-DNA complex at 2.1 A," Science, 252:809-817, 1991.
Pearson, "The fate of fingers." Nature. 455:160-164, 2008.
Porteus, "Zinc fingers on target," Nature, 459: 337-338, 2009.
Shukla et al., "Precise genome modification in the crop species *Zea mays* using zinc-finger nucleases," Nature, 459(7245):437-441, 2009.
Bibikova et al., "Stimulation of homologous recombination through targeted cleavage by chimeric nucleases." Mol. Cell Biol., 21(1):289-297, 2001.
Kim and Chandrasegaran, "Chimeric restriction endonuclease," Proc. Natl. Acad. Sci. USA,91(3):883-887,1994.
Zou H, Zhao W, Zhang X, Han Y, Zou L, Chen G. "Identification of an avirulence gene, avrxa5, from the rice pathogen *Xanthomonas oryzae* pv. *oryzae*." Sci China Life Sci. Dec. 2010;53(12):1440-9. Epub Dec. 23, 2010.
Antony G, Zhou J, Huang S, Li T, Liu B, White F, Yang B. "Rice xa13 recessive resistance to bacterial blight is defeated by induction of the disease susceptibility gene Os-11N3". Plant Cell. Nov. 2010; 22(11):3864-76. Epub Nov. 23, 2010.
Domingues MN, De Souza TA, Cernadas RA, de Oliveira ML, Docena C, Farah CS, Benedetti CE. "The Xanthomonas citri effector protein PthA interacts with citrus proteins involved in

(56) References Cited

OTHER PUBLICATIONS nuclear transport, protein folding and ubiquitination associated with DNA repair". Mol Plant Pathol. Sep. 2010; 11(5):663-75.

Athinuwat D, Prathuangwong S, Cursino L, Burr T. "*Xanthomonas axonopodis* pv. *glycines* soybean cultivar virulence specificity is determined by avrBs3 homolog avrXg1". Phytopathology. Aug. 2009; 99(8):996-1004.

Rybak M, Minsavage GV, Stall RE, Jones JB. "Identification of *Xanthomonas citri* ssp. *citri* host specificity genes in a heterologous expression host". Mol Plant Pathol. Mar. 2009; 10(2):249-62.
Gürlebeck D, Jahn S, Gürlebeck N, Szczesny R, Szurek B, Hahn S, Hause G, Bonas U. "Visualization of novel virulence activities of the Xanthomonas type III effectors AvrBs1, AvrBs3 and AvrBs4". Mol Plant Pathol. Mar. 2009; 10(2):175-88.
Kay S, Bonas U. "How Xanthomonas type III effectors manipulate the host plant". Curr Opin Microbiol. Feb. 2009; 12(1):37-43. Epub Jan. 23, 2009. Review.
Park HJ, Han SW, Oh C, Lee S, Ra D, Lee SH, Heu S. "Avirulence gene diversity of *Xanthomonas axonopodis* pv. *glycines* isolated in Korea", J Microbiol Biotechnol. Sep. 2008; 18(9):1500-9.
Schornack S, Minsavage CV, Stall RE, Jones JB, Lahaye T. "Characterization of AvrHah1, a novel AvrBs3-like effector from Xanthomonas gardneri with virulence and avirulence activity". New Phytol. Jul. 2008; 179(2):546-56.
Hu J, Zhang Y, Qian W, He C. "Avirulence gene and insertion dement-based RFLP as well as RAPD markers reveal high levels of genomic polymorphism in the rice pathogen *Xanthomonas oryzae* pv. *oryzae*". Syst Appl Microbiol., vol. 30, 2007.
Thieme F, Szczesny R, Urban A, Kirchner O, Hause G, Boras U. "New type III effectors from *Xanthomonas campestris* pv. *vesicatoria* trigger plant reactions dependent on a conserved N-myristoylation motif". Mol Plant Microbe Interact. Oct. 2007; 20(10):1250-61.
Heuer H, Yin YN, Xue QY, Smalla K, Guo JH. "Repeat domain diversity of avrBs3-like genes in Ralstonia solatiacearum strains and association with host preferences in the field". Appl Environ Microbiol. Jul. 2007; 73(13):4379-84, Epub Apr. 27, 2007.
Sugio A, Yang B, Zhu T, White FF. "Two type III effector genes of *Xanthomonas oryzae* pv. *oryzae* control the induction of the host genes OsTFIIAgamma1 and OsTFX1 during bacterial blight of rice". Proc Natl Acad Sci U S A. Jun. 19, 2007; 104(25):10720-5, Epub Jun. 11, 2007.
Gonzalez C, Szurek B, Manceau C, Mathieu T, Séré Y, Verdier V. "Molecular and pathotypic characterization of new Xanthomonas oryzae strains from West Africa". Mol Plant Microbe Interact. May 2007; 20(5):534-46.
Niño-Liu DO, Ronald PC, Bogdanove AJ. "Xanthomonas oryzae pathovars: model pathogens of a model crop". Mol Plant Pathol. Sep. 2006; 7(5):303-24.
Kim JG, Choi S, Oh J, Moon JS, Hwang I. "Comparative analysis of three indigenous plasmids from *Xanthomonas axonopodis* pv. *glycines*". Plasmid. Sep. 2006; 56(2):79-87, Epub May 11, 2006.
Jordan T, Römer P, Meyer A, Szczesny R, Pierre M, Piffanelli P, Bendahmane A, Bonas U, Lahaye T. "Physical delimitation of the pepper Bs3 resistance gene specifying recognition of the AvrBs3 protein from *Xanthomonas campestris* pv. *vesicatoria*". Theor Appl Genet. Sep. 2006; 113(5):895-905. Epub Jul. 28, 2006.
Fujikawa T, Ishihara H, Leach JE, Tsuyumu S. "Suppression of defense response in plants by the avrBs3/pthA gene family of *Xanthomonas* spp". Mol Plant Microbe Interact. Mar. 2006; 19(3):342-9.
Schornak S, Meyer A, Römer P, Jordan T, Lahaye T. "Gene-for-gene-mediated recognition of nuclear-targeted AvrBs3-like bacterial effector proteins". J Plant Physiol. Feb. 2006; 163(3):256-72. Epub Jan. 5, 2006. Review.
Büttner D, Lorenz C, Weber E, Bonas U. "Targeting of two effector protein classes to the type III secretion system by a HpaC- and HpaB-dependent protein complex from *Xanthomonas campestris* pv. *vesicatoria*". Mol Microbiol. Jan. 2006; 59(2):513-27.
Schornack S, Peter K, Bonas U, Lahaye T. "Expression levels of avrBs3-like genes affect recognition specificity in tomato Bs4- but not in pepper Bs3-mediated perception". Mol Plant Microbe Interact. Nov. 2005; 18(11):1215-25.
Kay S. Boch J, Bonas U. "Characterization of AvrBs3-like effectors from a Brassicaceae pathogen reveals virulence and avirulence activities and a protein with a novel repeat architecture". Mol Plant Microbe Interact. Aug. 2005; 18(8):838-48.
Weber E, Ojanen-Reuhs T, Huguet E, Hause G, Romantschuk M, Korhonen TK, Bonas U, Koebnik R. "The type III-dependent Hrp pilus is required for productive interaction of *Xanthomonas campestris* pv. *vesicatoria* with peppet host plants". J Bacteriol. Apr. 2005; 187(7):2458-68.
Yang B, Sugio A, White FF. "Avoidance of host recognition by alterations in the repetitive and C-terminal regions of AvrXa7, a type III effector of *Xanthomonas oryzae* pv. *oryzae*". Mol Plant Microbe Interact. Feb. 2005; 18(2):142-9.
Büttner D, Gürlebeck D, Noël LD, Bonas U. "HpaB from *Xanthomonas campestris* pv. *vesicatoria* acts as an exit control protein in type III-dependent protein secretion". Mol Microbiol. Nov. 2004; 54(3):755-68.
Yang B, White FF. "Diverse members of the AvrBs3/PthA family of type III effectors are major virulence detenninants in bacterial blight disease of rice". Mol Plant Microbe Interact. Nov. 2004; 17(11):1192-200.
Keshavarzi M, Soylu S, Brown I, Bonas U, Nicole M, Rossiter J, Mansfield J. "Basal defenses induced in pepper by lipopolysaccharides are suppressed by *Xanthomonas campestris* pv. *vesicatoria*". Mol Plant Microbe Interact. Jul. 2004;17(7):805-15. Erratum in: Mol Plant Microbe Interact. Sep. 2004; 17(9):1039.
Liang B, Yu TG, Guo B, Yang C, Dai L, Shea DL. "Cloning and chatactetization of a novel avirulence gene (arp3) from *Xanthomonas oryzae* pv. *oryzae*". DNA Seq. Apr. 2004; 15(2):110-7.
Schornack S, Ballvora A, Gürlebeck D, Peart J, Baulcombe D, Ganal M, Baker B, Boras U, Lahaye T. "The tomato resistance protein Bs4 is a predicted non-nuclear TIR-NB-3-LRR protein that mediates defense responses to severely truncated derivatives of AvrBs4 and overexpressed AvrBs3". Plant J. Jan. 2004; 37(1):46-60. Erratum in: Plant J. Mar. 2004; 37(5):787.
Noël L, Thieme F, Gäbler J, Büttner D, Bonas U. "XopC and XopJ, two novel type III effector proteins from *Xanthomonas campestris* pv. *vesicatoria*". J Bacteriol. Dec. 2003; 185(24):7092-102.
Büttner D, Bonas U. "Getting across—bacterial type III effector proteins on their way to the plant cell". EMBO J. Oct. 15, 2002; 21(20):5313-22. Review.
Marois E, Van den Ackerveken G, Bonus U. "The Xanthomonas type III effector protein AvrBs3 modulates plant gene expression and induces cell hypertrophy in the susceptible host". Mol Plant Microbe Interact. Jul. 2002; 15(7):637-46.
Büttner D, Nennstiel D, Klüsener B, Bonas U. "Functional analysis of HrpF, a putative type III translocon protein from *Xanthomonas campestris* pv. *vesicatoria*". J Bacteriol. May 2002; 184(9):2389-98.
Romero AM, Kousik CS, Ritchie DF. "Temperature Sensitivity of the Hypersensitive Response of Bell Pepper to *Xanthomonas axonopodis* pv. *vesicatoria*". Phytopathology. Feb. 2002; 92(2):197-203.
Lahaye T, Bonas U. "Molecular secrets of bacterial type III effector proteins". Trends Plant Sci. Oct. 2001; 6(10):479-85. Review.
Szurek B, Marois E, Bonas U, Van den Ackerveken G. "Eukaryotic features of the Xanthomonas type III effector AvrBs3: protein domains involved in transcriptional activation and the interaction with nuclear import receptors from pepper". Plant J. Jun. 2001; 26(5):523-34.
Ballvora A, Pierre M, van den Ackeiveken G, Schornack S, Rossier O, Ganal M, Lahaye T, Bonus U. "Genetic mapping and functional analysis of the tomato Bs4 locus governing recognition of the *Xanthomonas campestris* pv. *vesicatoria* AvrBs4 protein". Mol Plant Microbe Interact. May 2001; 14(5):629-38.
Bai J, Choi SH, Ponciano G, Leung H, Leach JE. "*Xanthomonas oryzae* pv. *oryzae* avirulence genes contribute differently and specifically to pathogen aggressiveness". Mol Plant Microbe Interact. Dec. 2000; 13(12):1322-9.

(56) References Cited

OTHER PUBLICATIONS

Rossier O, Van den Ackerveken G, Boras U. "HrpB2 and HrpF from Xanthomonas are type III-secreted proteins and essential for pathogenicity and recognition by the host plant". Mol Microbiol. Nov. 2000; 38(4):828-38.
Boras U, Van den Ackerveken G, Büttner D, Hahn K, Marois E, Nennstiel D, Noel L, Rossier O, Szurek B. "How the bacterial plant pathogen *Xanthomonas campestris* pv. *vesicatoria* conquers the host". Mol Plant Pathol. Jan. 2000; 1(1):73-6.
Rossier O, Wengelnik K, Hahn K, Bonas U. "The Xanthomonas Hrp type III system secretes proteins from plant and mammalian bacterial pathogens". Proc Natl. Acad. Sci U S A. Aug. 3, 1999; 96(16):9368-73.
Zhu W, Yang B, Chittoor JM, Johnson LB, White FF. "AvrXa10 contains an acidic transcriptional activation domain in the functionally conserved C terminus". Mol. Plant Microbe Interact. Aug. 1998; 11(8):824-32.
Van den Ackerveken G, Marois E, Boras U. "Recognition of the bacterial avirulence protein AvrBs3 occurs inside the host plant cell". Cell. Dec. 27, 1996; 87(7):1307-16.
De Feyter R, Yang Y, Gabriel DW. "Gene-for-genes interactions between cotton R genes and *Xanthomonas campestris* pv. *malvacearum* avr genes". Mol Plant Microbe Interact. Mar.-Apr. 1993; 6(2):225-37.
Hopkins CM, White FF, Choi SH, Guo A, Leach JE. "Identification of a family of avirulence genes from *Xanthomonas oryzae* pv. *oryzae*". Mol Plant Microbe Interact. Nov.-Dec. 1992; 5(6):451-9.
Swarup S, Yang Y, Kingsley MT, Gabriel DW. "An Xanthomonas citri pathogenicity gene, pthA, pleiotropically encodes gratuitous avirulence on nonhosts", Mol Plant Microbe Interact. May-Jun. 1992; 5(3): 204-13.
Knoop V, Staskawicz B, Bortas U. "Expression of the avirulence gene avrBs3 from *Xanthomonas campestris* pv. *vesicatoria* is not under the control of hrp genes and is independent of plant factors". J Bacteriol. Nov. 1991; 173(22):7142-50.
Canteros B, Minsavage G, Bonas U, Pring D, Stall R. "A gene from *Xanthomonas campestris* pv. *vesicatoria* that determines avirulence in tomato is related to avrBs3". Mol Plant Microbe Interact. Nov.-Dec. 1991; 4(6):628-32.
Bonas U, Stall RE, Staskawicz B. "Genetic and structural characterization of the avirulence gene avrBs3 from *Xanthomonas campestris* pv. *vesicatoria*". Mol Gen. Genet. Jul. 1989; 218(1):127-36.
Zhu. PL, Zhao S, Tang JL, Feng JX. "The rsmA-like gene ismA(Xoo) of *Xanthomonas oryzae* pv. *oryzae* regulates bacterial virulence and production of diffusible signal factor". Mol Plant Pathol. Apr. 2011; 12(3):227-37. doi:10.1111/j.1364-3703.2010.00661.x. Epub Oct. 1, 2010.
Yuan T, Li X, Xiao J, Wang J, Wang S. "Characterization of Xanthomonas oryzae-responsive cis-acting element in the promoter of rice race-specific susceptibility gene Xa13". Mol Plant. Mar. 2011; 4(2):300-9. Epub Jan. 5, 2011.
Bonas, "How *Xanthomonas* maniplulates the plant cell" (abstract), XIV International Congress on Molecular Plant-Microbe Interactions, Quebec City, Canada, Jul. 19-23, 2009, 2 pages.
Boch et al., "Molecular characterization of three AvrBs3-like effectors from the *Arabidopsis* pathogen *Xanthomonas campestris* pv. *armoraciae*" (abstract), XIV International Congress on Molecular Plant-Microbe Interactions, Quebec City, Canada, Jul. 19-23, 2009, 1 page.
Hahn et al., "New mechanistic insights into the virulence activity of the *Xanthomonas* type III effector AvrBs3" (abstract), XIV International Congress on Molecular Plant-Microbe Interactions, Quebec City, Canada, Jul. 19-23, 2009, 1 page.
Nature Reprint Collection [online]. "TAL effector nucleases," Oct. 2011, [retrieved on Mar. 14, 2012]. Retrieved from the Internet: URL <http://www.nature.com/nbt/collections/talen/index.html>. 32 pages.
Arimondo et at., "Exploring the cellular activity of camptothecin-triple-helix-forming oligonucleotide conjugates," Mol. Cell. Biol., 2006, 26:324-333.

Authorized Officer Thierry Seroz, International Search Report, PCl/US2010/059932, dated Nov. 22, 2011, 9 pages.
Authorized Officer E. Pepper Cano. Invitation to Pay Additional Fees, in International Application No. PCT/US2010/059932, dated May 24, 2011, 9 pages.
Bitinaite et al, "FokI dimerization is requited for DNA cleavage," Proc. Natl. Acad. Sci. USA, 1998, 95:10570-10575.
Bodganove et al., "TAL effectors: Customizable Proteins for DNA Targeting," Science 2011, 333: 1843-1846.
Busk, "Regulatory elements in vivo in the promoter of the abscisic acid responsive gene rab17 from maize," Plant J., 1997. 11:1285-1295.
Cathomen et al., "Zinc-finger nucleases: the next generation emerges," Molec. Ther., Jul. 2008, 16(7):1200-1207.
Christian et al., "Targeting DNA Double-Strand Breaks with TAL Effector Nucleases," Genetics, Oct. 2010, 186(2):757-761, and Supporting Information Retrieved from the Internet: URL http://www.genetics.org/cgi/content/full/genetics.110.120717/DCI, 8 pages.
Cole et at., "The Jpred 3 secondary structure prediction server," Nucl. Acids Res., 2008, 36:W197-W201.
DeFrancesco, L. "Move over ZFNs." Nat. Biotechnol., vol. 29, 2011, pp. 681-684.
Eisenschmidt et al., "Developing a programmed restriction endonuclease for highly specific DNA cleavage," Nucl. Acids Res., 2005, 33:7039-7047.
Engler et al., "A One Pot, One Step, Precision Cloning Method with High Throughput Capability," PLoS One, 2008, 3:e3647.
Engler et at, "Golden Gate Shuffling: A One-Pot DNA Shuffling Method Based on Type Its Restriction Enzymes," PLoS One, 2009, 4:e5553.
Foley et al., "Rapid Mutation of Endogenous Zebrafish Genes Using Zinc Finger Nucleases Made by Oligomerized Pool Engineering (OPEN)," PLoS One, 2009, 4:e4348.
GenBank Accession No. ACD58243, May 19, 2008, 2 pages.
GenBank Accession No. AY986492, Jun. 24, 2005, 2 pages.
GenBank Accession No. P14727, Jun. 28, 2011, 3 pages.
GenBank Accession No. X16130, Oct. 15, 2007, 3 pages.
Gonchar et al. 'Science.sebenzyme.com' [online]. PspXI, a novel restriction endonuclease that recognizes the unusual DNA sequence S'-VC; TCGAGB-3, 2005, [retrieved on Jan. 8, 2013]. Retrieved from the Internet: URL: <http://science.sibenzyme.com/article8_article_3_1.phtr>. 4 pages.
Gu et al.,"R gene expression induced by a type-III effector triggers disease resistance in rice," Nature, 2005, 435:1122-1125.
Haber, "In vivo biochemistry: Physical monitoring of recombination induced by site-specific endonucleases," Bioessays, 1995, 17:609-620.
Handel et al,, "Expanding or restricting the target site repertoire of zinc-finger nucleases: the inter-domain linker as a major determinant of target site selectivity," Mol. Ther., 2009, 17:104-111.
Herbers et al. "Race-specificity of plant resistance to bacterial spot disease determined by repetitive motifs in a bacterial avirulence protein," Nature, 1992, 356:172-174.
Kim et al., "Hybrid restriction enzymes: zinc finger fusions to FokI cleavage," Proc. Natl. Acad. Sci. USA, 1996, 93:1156-1160.
Moore et al., "Transactivated and chemically inducible gene expression in plants," The Plant Journal, 2006, 45:651-683.
Mussolino et al. "A novel TALE nuclease scaffold enables high genome editing activity in combination with low toxicity." Nucleic Acids Res, 2011, 39, 9283-9293.
Nissan et al. "The type III effectors HsvG and HsvB of gall-forming Pantoea agglomerans determine host specificity and function as transcriptional activators." *Molecular Microbiology*, 61(5), 2006, pp. 1118-1131.
Padidam, "Chemically regulated gene expression in plants," Curr. Opin. Plant Biol., 2003, 6:169-177.
Paques and Duchateau, "Meganucleascs and DNA Double-Strand Break-Induced recombination: Perspectives for Gene Therapy," Curr. Gene Ther., 2007, 7:49-66.
Porteus and Baltimore, "Chimeric nucleases stimulate gene targeting in human cells," Science, 2003, 300:763.
Porteus and Carroll, "Gene targeting using zinc finger nucleases," Nature Biotechnol., 2005, 23:967-973.

(56) References Cited

OTHER PUBLICATIONS

Simon et al., "Targeting DNA with triplex-forming oligonucleotides to modify gene sequence," Biochimie, 2008, 90:1109-1116.
Skipper, "The holy grail for plant biologists," *Nature Reviews*, Genetics, Jun. 2009. 10:350.
Tovkach et al., "A toolbox and procedural notes for characterizing novel zinc finger nucleases for genome editing in plant cells," The Plant Journal, 2009, 57:747-757.
Vergunst et al., "VirB/D4-Dependent Protein Translocation from Agrobacterium into Plant Cells," Science, 2000, 290:979-982.
Wang et al., "Chemically regulated expression systems and their applications in transgenic plants," Transgenic Res., 2003, 12:529-540.
Yang et al., "Os8N3 is a host disease-susceptibility gene for bacterial blight of rice," Proc. Natl. Acad. Sci. USA, 2006, 103:10503-10508.
Zhang et al., "High frequency targeted mutagenesis in *Arabidopsis thaliana* using zinc finger nucleases," Proc. Natl. Acad. Sci. USA, 2010, 107:12028-12033.
Zuo and Chua, "Chemical-inducible systems for regulated expression of plant genes," Curr. Opin. Biotechnol., 2000, 11:146-151.
Choulika et al., "induction of homologous recombination in mammalian chromosomes by using the I-Seel system of *Saccharomyces cerevisiae*," Mol. Cell. Bol., 15(4):1968-1973, 1995.
Gen Bank Accession No. CP000967, GI: 188518722, May 19, 2008, 171 pages.
Minczuk et al., "Development of a single-chain, quasi-dimeric zinc-finger nuclease for the selective degradation of mutated human mitochondria DNA," Nucl. Acids Res., 36(12):3926-3938, 2008.
Pingoud and Silva, "Precision genome surgery," Nature Biotechnol., 25(7):743-744, 2007.
Potenza et al., "Targeting transgene expression in research, agricultural, and environmental applications: Promoters used in plant transformation," In vitro Cell. Dev. Biol., 40(1):1-22, 2004.
Rouet et at., "Expression of a site-specific endonuclease stimulates homologous recombination in mammalian cells," Proc. Natl. Acad. Sci. USA, 91(13):6064-6068, 1994.
Rouet et at., "Introduction of double-strand breaks into the genome of mouse cells by expression of a rare-cutting endonuclease," Mol. Cell. Biol., 14(12):8096-8106, 1994.
Li T, Huang S, Zhao X, Wright DA, Carpenter S, et al. 2011, "Modularly assembled designer TAL effector nucleases for targeted gene knockout and gene replacement in eukaryotes". *Nucl Acids Res* 39:6315-25.
Mahfouz MM, Li L, Shamimuzzaman M, Wibowo A, Fang X, Zhu JK. 2011. "De novo-engineered transcription activator-like effector (TALE) tiyhrid nuclease with novel DNA binding specificity creates double-strand breaks". *Proc Natl Acad Sci USA* 108:2623-8.
Mak C. 2011. "Sequence-specific DNA-binding TALEs". Nat Biotechnol 29:43.
Miller JC, Tan S, Qiao G, Bartow KA, Wang J, et al. 2011. "A Tale nuclease architecture for efficient genome editing". *Nat Biotechnol* 29:143-8.
Scholze H, Boch J. 2011. "TAL effectors are remote controls for gene activation". *Curr Opin Microbiol* 14:47-53.
Antony G. 2010. "*Molecular basis of avrXa7 mediated virulence in bacterial blight of rice*". Kansas State University, Manhattan. 89 pp.
Cermak T, Christian M, Doyle E, Schmidt C, Bogdanove A, Voytas DF. "Engineered TAL effector nucleases: new tools for genome editing". *Proc. Workshop on Genome Engineering*, Nov. 16, 2010 (Abstract), 2 pages.
Murakami MT, Sforca ML, Neves JL, Paiva JH, Domingues MN, et al. 2010. "The repeat domain of the type III effector protein PthA shows a TPR-like structure and undergoes conformational changes upon DNA interaction". *Proteins* 78:3386-95.
White FF, Yang B. 2009. "Host and pathogen factors controlling the rice/*Xanthomonas oryzae* interaction", *Plant Physiol* 150:1677-86.
White FF, Potnis N, Jones JB, Koebnik R. 2009. "The type III effectors of *Xanthomonas*". *Mol Plant Pathol* 10:749-66.

Bibikova et al. (2003) "Enhancing Gene Targeting with Designed Zinc Finger Nucleases," Science 300(5620):764.
Fajardo-Sanchez et al. (2008) "Computer design of obligate heterodimer meganucleases allows efficient cutting of custom DNA sequences," Nucleic Acids Res. 36(7):2163-2173.
GenBank Accession No. J04623, Apr. 26, 1993, 2 pages.
GenBank Accession No. M28828, Apr. 26. 1993, 4 pages.
Choo et al. (1994) "In vivo repression by a site-specific DNA-binding protein designed against an oncogenic sequence," Nature 372(6507):642-645.
Greisman & Pabo (1997) "A General Strategy for Selecting High-Affinity Zinc Finger Proteins for Diverse DNA Target Sites," Science 275(5300):657-661.
Guan et al. (2002) "Heritable endogenous gene regulation in plants with designed polydactyl zinc finger transcription factors," Proc. Natl. Acad. Sci. USA 99(20):13296-13301.
Hurt et al. (2003) "Highly specific zinc finger proteins obtained by directed domain shuffling and cell-based selection," Proc Natl Acad Sci USA 100(21):12271-12276.
Isalan et al, (2001) "A rapid, generally applicable method to engineer zinc fingers illustrated by targeting the HIV-1 promoter," Nat Biotechnol 19(7):656-660.
Li et al. (1992) "Functional domains in Fok I restriction endonuclease," Proc. Natl. Acad. Sci. U.S.A 89 (10):4275-4279.
Liu et al., (1997) "Design of polydactyl zinc-finger proteins for unique addressing within complex genomes," Proc. Natl. Acad. Sci. USA 94(11):5525-5530.
Mino et al. (2009) "Efficient double-stranded DNA cleavage by artifical zinc-finger nucleases composed of one zinc-finger protein and a single-chain FokI dimer," J. Biotechnol. 140(3-4):156-161.
Pomerantz et al., (1995) "Stmcture-Based Design of Transcription Factors", Science 267(5194):93-96.
Puchta et al. (1993) "Homologous recombination in plant cells is enhanced by in vivo induction of double strand breaks into DNA by a site-specific endonuclease.," Nucleic Acids Res. 21 (22):5034-5040.
Segal et al. (1995) "Endonuclease-induced, targeted homologous extrachromosomal recombination in Xenopus oocytes," Proc. Natl. Acad. Sci. U.S.A. 92(3):806-810.
Sera (2005) "Inhibition of virus DNA replication by artificial zinc finger proteins.," J. Vir. 79(4):2614-2619.
Takenaka et al. (2007) "Inhibition of tomato yellow leaf curl virus replication by artificial zinc-finger proteins," Nucl Acids Symposium Series 51(1):429-430.
Thierry et al. (1991) "Cleavage of yeast and bacteriophage T7 genomes at a single site using the rare cutter endonuclease I-Sce I.," Nucleic Acids Res. 19(1):189-190.
Urnov et al. (2005) "Highly efficient endogenous human gene correction using designed zinc-finger nucleases,".Nature 435 (7042) : 646-651.
Al-Saadi et al., "All Five Host-Range Variants of *Xanthomonas citri* Carry One pthA Homolog With 17.5 Repeats That Determines Pathogenicity on Citrus, but None Determine Host-Range Variation," *MPMI*, 2007, pp. 934-943, vol. 20, No. 8, The American Phytopathological Society.
Studholme, et al., "Genome-wide sequencing data reveals virulence factors implicated in banana *Xanthomonas* wilt," *FEMS Microbiol Lett*, 2010, pp. 182-192, vol. 310, Blackwell Publishing Ltd.
Boller el al., "Innate inurtunity in plants: an arms race between pattern recognition receptors in plants and effectors in microbial pathogens," *Science*, 2009, vol. 324, pp. 742-744.
Borevitz et al., "Activation tagging identifies a conserved MYB regulator of phenylpropanoid biosynthesis," *Plant Cell*, 2000, vol. 12, pp. 2383-2394.
Cermak et al., Poster and Abstract—"Engineered TAL effector nucleases: new tools for genome editing," *Northwest Genome Engineering Consortium Workshop on Genome Engineering*, 2010, 3 pages.
Christian et al., Poster and Abstract—"Fusions of TAL effectors to the FokI endonuclease confer site specificity in DNA cleavage," IAPB 12th World Congress and In Vitro Biology Meeting, Jun. 2010, 4 pages.

(56) References Cited

OTHER PUBLICATIONS

Cornelius, "The type III secretion injectisome," *Nat. Rev. Microbiol.*, 2006, vol. 4, pp. 811-825.
Desjarlais el ai., "Toward rules relating zinc finger protein sequences and DNA binding site preferences," *Proc. Natl. Acad. Sci.*, USA, 1992. vol. 89, pp. 7345-7349.
Göhre et al., "Breaking the barriers: microbial effector molecules subvert plant immunity," *Ann. Rev. Phytopathol.*, 2008, vol. 46, pp. 189-215.
Jones et al., "The plant immune system," *Nature*, 2006, vol. 444, pp. 323-329.
Nakagawa et at., "Development of series of gateway binary vectors, pG WBs, for realizing efficient construction of fusion genes for plant transformation," *J. Biosci. Bioeng.*, 2007, vol. 104, pp. 24-41.
Pennist, "The Tale of the TALES," *Science*, 2012, vol. 338, pp. 1408-1411.
Morbitzer et al., "Assembly of custom TALE-type DNA binding domains by modular cloning," *Nucleic Acids Research*, 39(13):5790-5799, 2011.
Zhang, F., Broad Institute, Slides titled: "Informtional Seminar for United States Patent Office on TAL Effectors", pp. 1-37, Presented Dec. 5, 2012 at the USPTO Offices in Alexandria, VA.
Third Party Preissuance Submission Under 37 CFR § 1.290 dated Jun. 21, 2013 in U.S. Appl. No. 13/755,826.
Communication Pursuant to Rule 114(2) EPC dated Jun. 20, 2013 in European Application No. 10706358.8.
Geißler, R., et al., "Transcriptional Activators of Human Genes with Programmable DNA-Specificity," *PLoS One*, May 2011, pp. 1-7, vol. 6(5), Open Access.
Gürlebeck, D., et al., "Type III effector proteins from the plant pathogen *Xanthomonas* and their role in the interaction with the host plant," *Journal of Plant Physiology*, 2006, pp. 233-255, vol. 163, Elsevier.
Kay, S., et al., "A Bacterial Effector Acts as a Plant Transcription Factor and Induces a Cell Size Regulator," *Science*, Oct. 26, 2007, pp. 648-651, vol. 318, American Association for the Advancement of Science.
Miller, J,, et al., "A TALE nuclease architecture for efficient genome editing," *Nature Biotechnology*, Feb. 2011, pp. 143-148, vol. 29(2), Nature America, Inc.
Zhang, F., et al., "Efficient construction of sequence-specific TAL, effectors for modulating mammalian transcription." *Nature Biotechnology*, Feb. 2011, pp. 149-153, vol. 29(2), Nature America, Inc.
Pachuk el al., "Chain reaction cloning: a one-step method for directional ligation of multiple DNA fragments," *Gene*, 2000, pp. 19-25, vol. 243, Elsevier Science B.V.
Carroll, D., "Progress and prospects: Zinc-finger nucleases as gene therapy agents," *Gene Therapy*, 2008, pp. 1463-1468, vol. 15, Macmillan Publishers Limited.
Rosen, L., et al., "Homing endonuclease I-CreI derivatives with novel DNA target specificities," *Nucleic Acids Research*, 2006, pp. 4791-4800, vol. 34(17).
Gürlebeck, D., "Identifizierung and Analyse von Protein-Interaktionen des Typ III Effektors AvrBs3 aus *Xanthomonas campestris* pv. *vesicatoria*," Ph.D. Dissertation, Martin-Luther-Universität Halle-Wittenberg, 2007, 196 pages.
Figueiredo, J.F.L., "Genetic and Molecular Analysis of Pathogenicity Genes in *Xanthomonas citri* subsp. *citri*," Ph.D. Dissertation, University of Florida, 2009, 193 pages.
NCBI GenBank Accession No. CAA34257.1, Aug. 27, 2007, 2 pages.

FIG. 1A
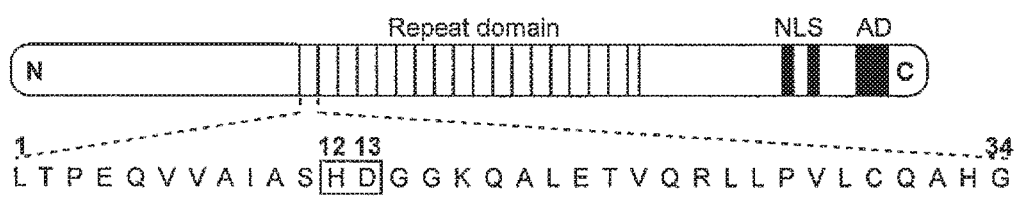
FIG. 1B
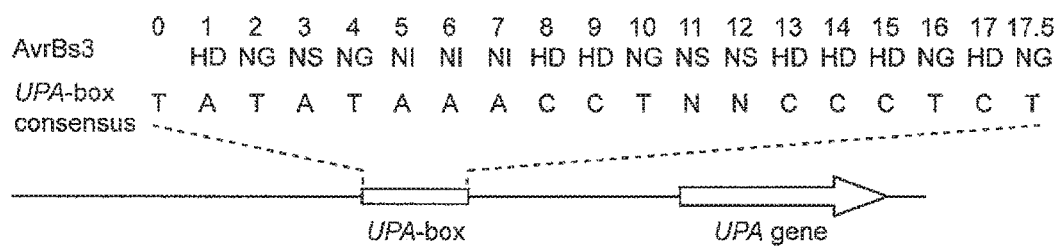
| | | HD | NI | NG | NS | NN | N* | HG | H* | IG |
|---|---|---|---|---|---|---|---|---|---|---|
| nucleotide frequency | A | 19 | 55 | 7 | 20 | 7 | 1 | 0 | 0 | 0 |
| | C | 69 | 5 | 12 | 10 | 2 | 7 | 2 | 0 | 0 |
| | G | 0 | 0 | 0 | 4 | 7 | 0 | 0 | 0 | 0 |
| | T | 5 | 0 | 50 | 3 | 1 | 1 | 2 | 1 | 1 |
hypervariable amino acids at position 12 + 13
FIG. 1C
| | repeat types | | | | | |
|---|---|---|---|---|---|---|
| | HD | NI | NG | NS | NN | IG |
| Code | C | A | T | N | R | T |
FIG. 1D FIG. 2A
| | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 21.5 |
|---|---|---|---|---|---|---|---|---|---|---|---|---|---|---|---|---|---|---|---|---|---|---|---|
| Hax2 | | NN | IG | NG | NI | NG | NG | HD | NG | HD | NI | HD | NI | HD | NG | HD | NG | HD | HD | NG | NG | NI | NG |
| Hax2-box | T | G | T | T | A | T | T | C | T | C | A | C | T | C | T | C | C | T | T | A | T | | |
| | 0 | 1 | 2 | 3 | 4 | 5 | 6 | 7 | 8 | 9 | 10 | 11 | 11.5 |
|---|---|---|---|---|---|---|---|---|---|---|---|---|---|
| Hax3 | | NI | HD | NI | HD | HD | HD | NS | NS | NS | HD | NI | NG |
| Hax3-box | T | A | C | A | C | C | A | A | A | C | A | T | |
| | 0 | 1 | 2 | 3 | 4 | 5 | 6 | 7 | 8 | 9 | 10 | 11 | 12 | 13 | 14 | 14.5 |
|---|---|---|---|---|---|---|---|---|---|---|---|---|---|---|---|---|
| Hax4 | | NI | HD | HD | NG | NS | NS | NI | HD | NG | NI | NS | NI | NG | NI | NG |
| Hax4-box | T | A | C | C | T | A | A | A | C | T | A | A | A | T | A | T |
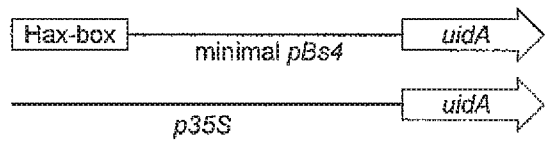
FIG. 2B
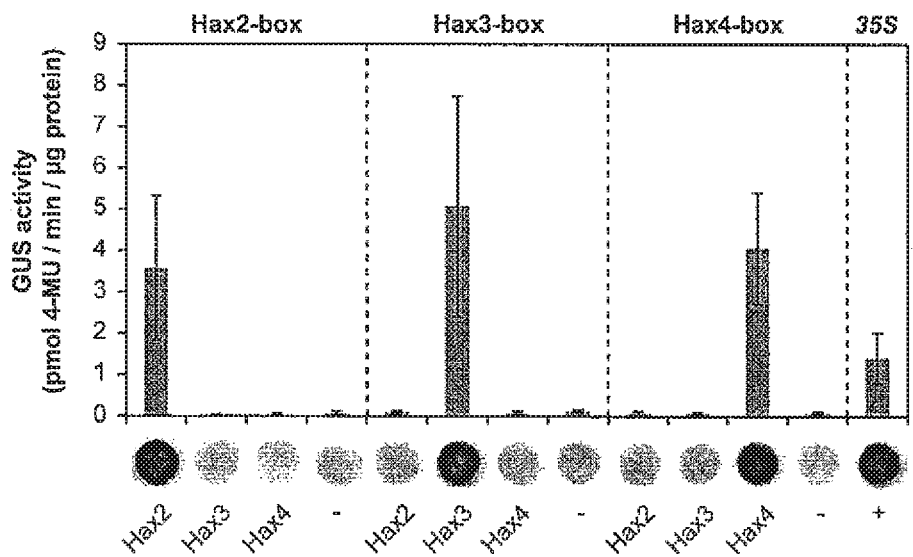
FIG. 2C

```
              0  1  2  3  4  5  6  7  8  9 10 11 12 13 14 15 16 16.5
                          1 - 16 x HD
ArtHD1.5    NI HD
ArtHD16.5   NI HD HD HD HD HD HD HD HD HD HD HD HD HD HD HD HD
ArtHD-box T A  C  C  C  C  C  C  C  C  C  C  C  C  C  C  C  C  C
```

FIG. 4B [ArtHD-box]—minimal pBs4—uidA→

FIG. 5A

| | | -120 | | | | | | | | | | | | | | | | | | -102 | HR (ECW-30R) |
|---|---|---|---|---|---|---|---|---|---|---|---|---|---|---|---|---|---|---|---|---|---|
| Bs3 UPA-box | | T | A | T | A | T | A | A | A | C | C | T | A | A | C | C | A | T | C | C | |
| AvrBs3 | | 0 | 1 | 2 | 3 | 4 | 5 | 6 | 7 | 8 | 9 | 10 | 11 | 12 | 13 | 14 | 15 | 16 | 17 17.5 | | + |
| | | HD | NG | NS | NG | NI | NI | NI | HD | HD | NG | NS | NS | HD | HD | HD | NG | HD | NG | | |
| AvrBs3Δrep16 | | 0 | 1 | 2 | 3 | 4 | 5 | 6 | 7 | 8 | 9 | 10 | 11 | 12 | 13 13.5 | | | | | | − |
| | | HD | NG | NS | NG | NI | NI | NI | HD | HD | NG | HD | NG | HD | NG | | | | | | |
| AvrBs3Δrep109 | | 0 | 1 | 2 | 3 | 4 | 5 | 6 | 7 | 8 | 9 | 10 | 11 | 12 | 13 | 14 14.5 | | | | | + |
| | | HD | NG | NS | NG | NI | NI | NI | HD | HD | NG | NS | NS | NG | HD | NG | | | | | |
| AvrHah1 | | | 0 | 1 | 2 | 3 | 4 | 5 | 6 | 7 | 8 | 9 | 10 | 11 | 12 | 13 13.5 | | | | | + |
| | | | NN | IG | NI | NI | NI | HD | HD | NG | NN | NI | HD | HD | HD | NG | | | | | |

FIG. 5B

| | | -133 | | | | | | | | | | | | | | | | | | -115 | HR (ECW) |
|---|---|---|---|---|---|---|---|---|---|---|---|---|---|---|---|---|---|---|---|---|---|
| Bs3-E UPA-like-box | | T | A | T | A | T | A | A | A | C | C | T | C | T | C | T | A | T | T | C | |
| AvrBs3 | | 0 | 1 | 2 | 3 | 4 | 5 | 6 | 7 | 8 | 9 | 10 | 11 | 12 | 13 | 14 | 15 | 16 | 17 17.5 | | − |
| | | HD | NG | NS | NG | NI | NI | NI | HD | HD | NG | NS | NS | HD | HD | HD | NG | HD | NG | | |
| AvrBs3Δrep16 | | 0 | 1 | 2 | 3 | 4 | 5 | 6 | 7 | 8 | 9 | 10 | 11 | 12 | 13 13.5 | | | | | | + |
| | | HD | NG | NS | NG | NI | NI | NI | HD | HD | NG | HD | NG | HD | NG | | | | | | |
| AvrBs3Δrep109 | | 0 | 1 | 2 | 3 | 4 | 5 | 6 | 7 | 8 | 9 | 10 | 11 | 12 | 13 | 14 14.5 | | | | | − |
| | | HD | NG | NS | NG | NI | NI | NI | HD | HD | NG | NS | NS | NG | HD | NG | | | | | |
| AvrHah1 | | | 0 | 1 | 2 | 3 | 4 | 5 | 6 | 7 | 8 | 9 | 10 | 11 | 12 | 13 13.5 | | | | | − |
| | | | NN | IG | NI | NI | NI | HD | HD | NG | NN | NI | HD | HD | HD | NG | | | | | |

FIG. 5C

| | -87 | | | | | | | | | | | | | | | | | -70 | HR |
|---|---|---|---|---|---|---|---|---|---|---|---|---|---|---|---|---|---|---|---|
| Xa27 | T | A | G | A | A | G | A | A | G | A | G | A | C | C | C | A | T | A | + |
| xa27 | -84 T | A | G | A | A | G | A | G | A | C | C | A | A | T | A | G | A | -67 G | − |
| AvrXa27 | 0 | 1 | 2 | 3 | 4 | 5 | 6 | 7 | 8 | 9 | 10 | 11 | 12 | 13 | 14 | 15 | 16 16.5 | | |
| | NI | NN | N* | NG | NS | NN | NN | NN | NI | NN | NI | N* | HD | HD | NI | NG | NG | | |

FIG. 5D

```
                                                                      Gene
            -251                                              -227  induction
    Xa13    T G C A T C T C C C C T A C T G T A C A C C A C       +
            -223                                              -199
    xa13    G A T A T G T C C C C T C C A A C T A T A T A A
            0  1  2  3  4  5  6  7  8  9 10 11 12 13 14 15 16 17 18 19 20 21 22 2323.5
    PthXo1  NN HD NI HG HD NG N* HD HD NI NG NG NI HD NG NN NG NI NI NI NI N* NS N*
```

FIG. 5E

```
            -136                                          -113
    OsTFX1  T A T A A A A G G C C C T C A C C A A C C C A T     +
            0  1  2  3  4  5  6  7  8  9 10 11 12 13 14 15 16 17 18 19 20 21 2222.5
    PthXo6  NI H* NI NN NN NN NN NN HD NI HD HG HD NI N* NS NI NI HG HD NS NS NG
```

FIG. 5F

```
            -469                                          -447
    OsTFIIAγ1 T A T A A T C C C C A A A T C C C T C C T C      +
            0  1  2  3  4  5  6  7  8  9 10 11 12 13 14 15 16 17 18 19 20 2121.5
    PthXo7  NI NG NI NI N* NN HD HD N* NI NI NI NG HD HG NN NS NN HD HD NG N*
```

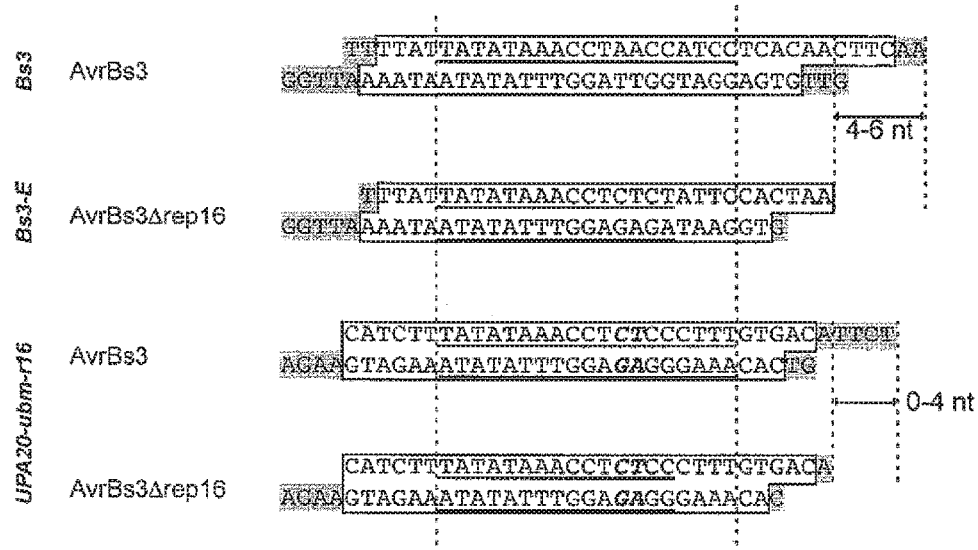

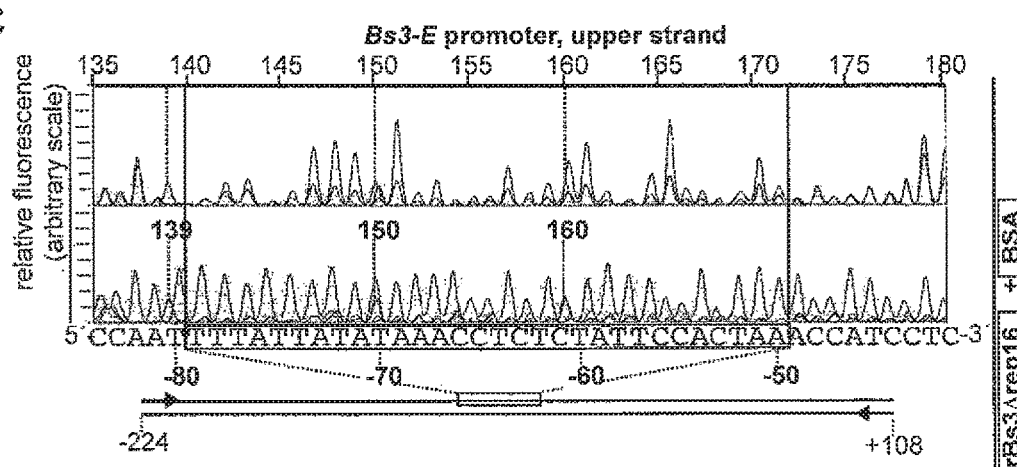

FIG. 10A
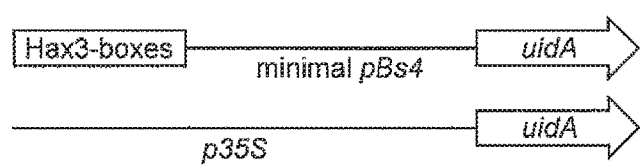
FIG. 10B
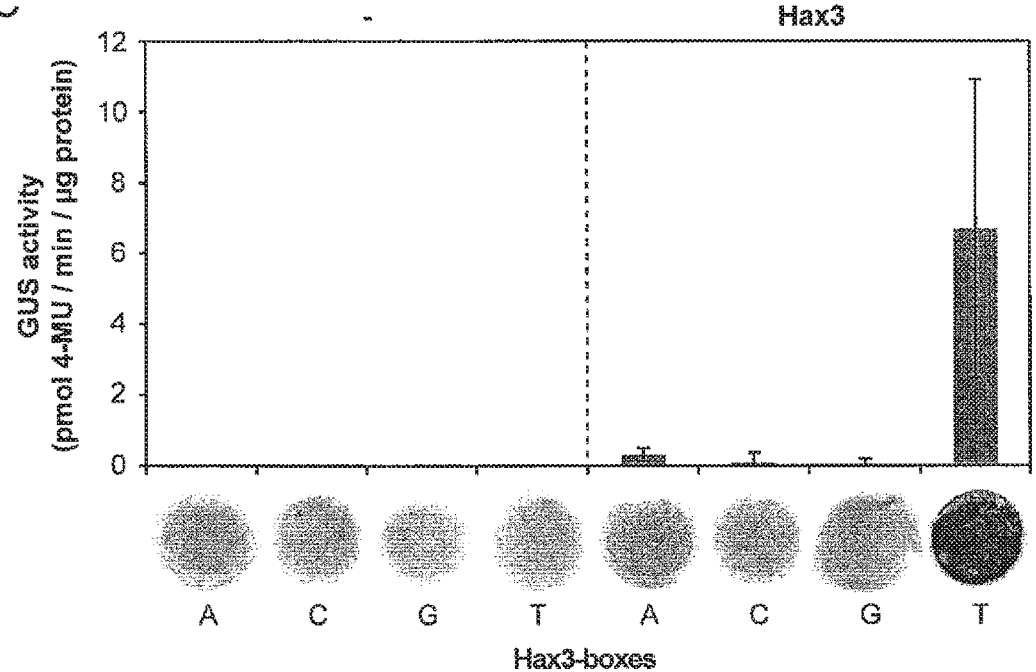
FIG. 10C

FIG. 12A
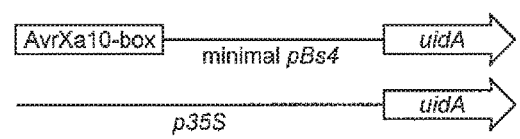
FIG. 12B
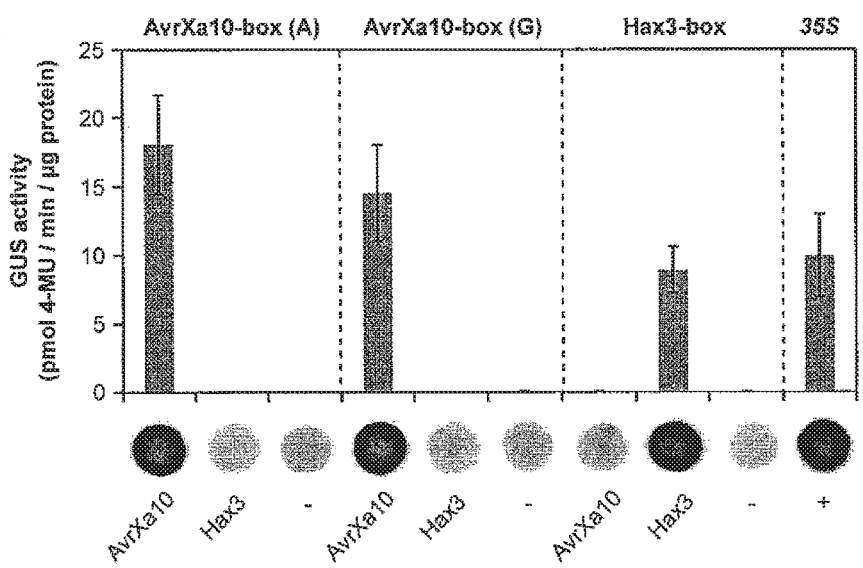
FIG. 12C

FIG. 13A
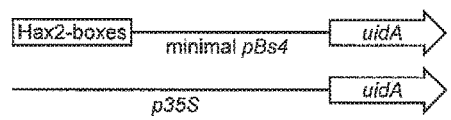
FIG. 13B
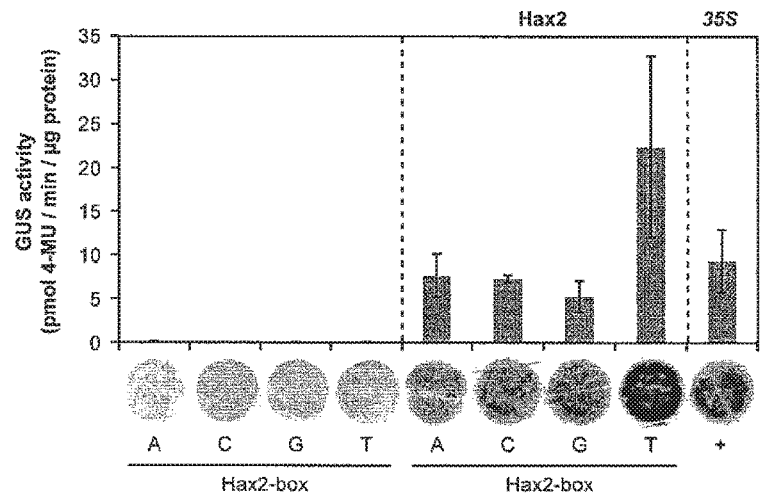
FIG. 13C

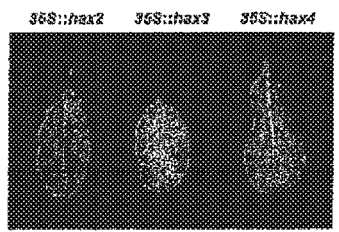
FIG. 14A
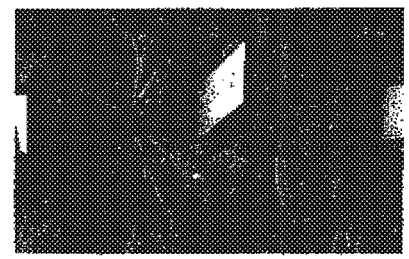
FIG. 14B
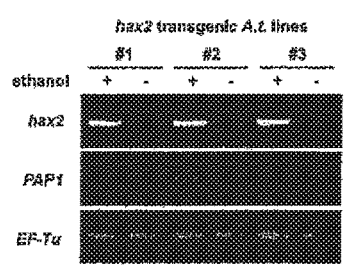
FIG. 14C
FIG. 14D
Hax2       0  1  2  3  4  5  6  7  8  9  10 11 12 13 14 15 16 17 18 19 20 21 21.5
           NN IG NG NI NG NG HD NG HD NI HD NI HD NG HD NG HD HD NG NG NI NG
Hax2-box    T  G  T  T  A  T  T  C  T  C  A  C  T  C  T  C  C  T  T  A  T
FIG. 14E
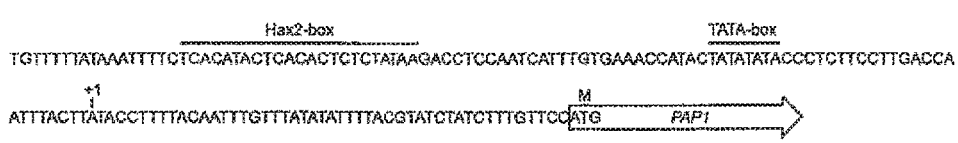

FIG. 15A

| Organism[a] | TAL effector | Repeats[b] (amino acid 12 + 13) | Predicted target DNA sequences[c] | Accession |
|---|---|---|---|---|
| TAL effectors with shown specificity (this work and others) | | | | |
| Xcv 71-21 | AvrBs3 | HD-NG-NS-NG-NI-NI-NI-HD-HD-NG-NS-NS-HD-HD-HD-NG-HD-NG | TCTNTAAACCTNNCCCTCT | CAA34257 |
| Xg XV444 | AvrHah1 | NN-IG-NI-NI-NI-HD-HD-NG-NN-NI-HD-HD-HD-NG | TRTAAACCTRACCCT | ABP97430 |
| Xca 5 | Hax2 | NN-IG-NG-NI-NG-NG-HD-NG-HD-NI-HD-NI-HD-NG-HD-NG-HD-NG-NG-NI-NG | TGTTATTCTCACACTCTCCTTAT | AAY43358 |
| Xca 5 | Hax3 | NI-HD-NI-HD-HD-HD-NS-NS-NS-HD-NI-NG | TACACCCNNNCAT | AAY43359 |
| Xca 5 | Hax4 | NI-HD-HD-NG-NS-NS-NI-HD-NG-NI-NS-NI-NG-NI-NG | TACCTNNACTANATAT | AAY43360 |
| Xoo PXO86 | AvrXa10 | NI-HG-NI-HG-NI-NI-NN-HD-NI-HD-NN-HG-NS-NG-HD-NG | TA•A•AARCACR•NTCT | AAA92974 |
| Xoo PXO99A | AvrXa27 | NI-NN-N*-NG-NS-NN-NN-NN-NI-NN-NI-N*-HD-HD-NI-NG-NG | TAR•TNRRRARA•CCATT | AAY54168 |
| Xoo PXO99A | PthXo1 | NN-HD-NI-HG-HD-NG-N*-HD-HD-NI-NG-NG-NI-HD-NG-NN-NG-NI-NI-NI-NI-N*-NS-N* | TRCA•CT•CCATTACTRTAAAA•N• | AAS46025 |
| Xoo PXO99A | PthXo6 | NI-H*-NI-NN-NN-NN-NN-NN-HD-NI-HD-HG-HD-NI-N*-NS-NI-NI-HG-HD-NS-NS-NG | TA•ARRRRRCAC•CA•NAA•CNNT | ABB70183 |
| Xoo PXO99A | PthXo7 | NI-NG-NI-NI-N*-NN-HD-HD-N*-NI-NI-NI-NG-HD-HG-NN-NS-NN-HD-HD-NG-N* | TATAA•RCC•AAATC•RNRCCT• | ABB70129 |
| TAL effectors with so far unknown specificity | | | | |
| Xcv 82-8 | AvrBs4 | NI-NG-NI-NI-NG-NG-NI-NS-NG-NI-NS-NG-HD-HD-NS-HD-NG-NG | TATAATTANTANTCCNCTT | CAA48680 |
| Xac NA-1 | Apl1 | NI-NG-NI-NI-NI-HD-HD-NG-HD-NG-NG-NG-NG-NS-HD-HD-NG-NG | TATAAACCTCTTTTNCCTT | BAA37119 |
| Xac NA-1 | Apl2 | NI-NG-NI-HD-NI-HD-HD-NG-HD-NG-NG-NG-NG-NI-HD-NG | TATACACCTCTTTTACT | BAA37120 |
| Xac NA-1 | Apl3 | NI-HD-NI-HD-NI-HD-HD-NG-HD-NG-NG-NI-HD-HD-NI-HD-HD-NG-HD-NG-NI-HD-NG-NG | TACACACCTCCTACCACCTCTACTT | BAA37121 |
| Xac 3213 | PthA | NI-NG-NI-NI-NI-NG-HD-NG-HD-NG-NG-NG-NG-NS-HD-HD-NG-NG | TATAAATCTCTTTTNCCTT | AAC43587 |
| Xac | PthB | HD-NG-HD-NG-NI-NG-HD-NG-HD-NI-NI-HD-HD-HD-HD-NG-NG-NG | TCTCTATCTCAACCCCTTT | AAO72098 |
| Xau C340 | PthC | HD-NG-HD-HD-NI-NG-NI-NG-NI-NI-HD-NG-HD-HD-HD-NG-NG-NG | TCTCCATATAACTCCCTTT | ABO77782 |
| Xac KC21 | HssB3.0 | NI-HD-NI-HD-NI-NG-N*-NI-N*-NI-HD-HD-NI-HD-NG | TACACAT•A•ACCACT | BAF46269 |
| Xcm | Avrb6 | HD-NI-NG-HD-HD-NI-HD-NI-NS-HD-HD-HD-NN-NG | TCATCCACANCCCRT | AAB00675 |
| Xcm XcmN | PthN | NI-HD-HD-NI-HD-NI-NG-NI-NN-HD-NI-NG-NG-NN | TACCACATARCATTR | AAB69865 |
| Xam CFBP1851 | PTHB | NI-NI-NN-NI-HD-NS-NS-NN-NG-HD-NN-NI-NG | TAARACNNRTCRAT | AAD01494 |
| Xoo JXOIII | AvrXa3 | HD-HD-HD-NG-NG-NN-HD-HD-NG | TCCCTTRCCT | AAN01357 |
| Xoo PXO2684 | AvrXa7 | NI-HG-NI-NI-NS-HD-NN-HD-HD-HD-NS-N*-N*-HD-HD-NS-NS-NN-NN-NI-NG-NN-NI-N*-NS-N* | TA•AANCRCCCN••CCNNRRATRA•N• | AAF98343 |
| Xoo | PthA1 | NN-HD-NS-NG-HD-NN-NG-NI-HD-NS- | TRCNTCRTACNCRCRCRRRRRRRCT | YP_200770 |

FIG. 15B

| | | | | |
|---|---|---|---|---|
| KACC10331 | | HD-NN-HD-NN-HD-NN-NN-NN-NN-NN-NN-NN-HD-NG | | |
| Xac 306 | PthA1 | NI-N*-NI-N*-NI-HD-HD-N*-NI-HD-NI-HD-N*-NI-HD-HD-NG | TA•A•ACC•ACAC•ACCT | NP_644708 |
| Xoo KACC10331 | PthA2 | NI-NG-NN-NG-NK-NG-NI-NN-NI-NN-NI-NN-NS-NG-NS-NN-NI-NG-NS-NG | TATRT•TARARARNTNRATNT | YP_201652 |
| Xac 306 | PthA2 | NI-HD-NI-HD-NI-HD-HD-NG-HD-NG-NG-NG-NG-NI-NI-NG | TACACACCTCTTTTAAT | NP_644725 |
| Xoo KACC10331 | PthA3 | NI-HG-NI-NI-NS-HD-NN-HD-HD-HD-NS-NG-N*-HD-HD-NS-NS-NN-NG | TA•AANCRCCCNT•CCNNRT | YP_201654 |
| Xac 306 | PthA3 | NI-HD-NI-HD-NI-NG-HD-NG-NG-NG-NI-NI-NI-NI-HD-NG | TACACATCTTTAAAACT | NP_644743 |
| Xoo KACC10331 | PthA4 | NI-N*-NI-NS-NN-NG-NN-NS-N*-NS-NN-NS-N*-HD-HG-HD-HD-HD-NS-N*-HD-HG-HD-HD-HD-HD-NG | TA•ANRTRN•NRN•C•CCCN•C•CCCCT | YP_200914 |
| Xac 306 | PthA4 | NI-N*-NI-NI-NI-HD-HD-NG-HD-NG-NG-NG-NG-NS-HD-HD-NG-NG | TA•AAACCTCTTTTNCCTT | NP_644793 |
| Xoo JXO1 | PthXo2 | NI-HG-NI-NN-NN-NI-NN-HD-NI-HD-NS-NS-NS-HD-NN-HD-NG-HD-HD-HD-NG-NG | TA•ARRARCACNNNCRCTCCCTT | AAS46026 |
| Xoo PXO61 | PthXo3 | NI-HG-NI-HG-NI-NI-NI-HD-NN-HD-HD-HD-NG-HD-NG-NI-HD-HD-NN-NS-NI-NN-NN-NG-NN-HD-N*-NS-N* | TA•A•AAACRCCCTCTACCRNARRTRC•N• | AAS46027 |
| Xoo PXO99A | Tal2a | NI-NG-NN-NG-NK-NG-NI-NN-NI-NN-NI-HD-N*-NS-NG | TATRT•TARARAC•NT | YP_001912778 |
| Xoo PXO99A | Tal4 | NI-NN-NN-NI-NI-NI-HD-NS-HG-NN-NN-NN-NI-NI-HG-HD | TARRAAACN•RRRAA•C | YP_001913182 |
| Xoo PXO99A | Tal5a | NI-NS-HD-HG-NS-NN-HD-H*-NG-NN-NN-HD-HD-NG-HD-NG | TANC•NRC•TRRCCTCT | YP_001913457 |
| Xoo PXO99A | Tal6a | NI-N*-NI-NS-NN-NG-NN-NS-N*-NS-NN-NS-N*-NI-HG-HD-NI-HD-HD-NG | TA•ANRTRN•NRN•A•CACCT | YP_001913480 |
| Xoo PXO99A | Tal7a | NI-HG-NI-NI-NI-NN-HD-NS-NN-NS-NN-HD-NN-NI-HD-NN-NS-NG | TA•AAARCNRNRCRACRNT | YP_001913755 |
| Xoo PXO99A | Tal7b | NI-HG-NS-HG-HG-HD-NS-NG-HD-NN-NG-HG-NG-HD-HG-HD-HD-NI-NN-NG | TA•N••CNTCRT•TC•CCART | YP_001913759 |
| Xoo PXO99A | Tal8a | NI-HG-NI-NI-NI-NN-HD-NS-NN-NS-NN-HD-NN-NI-HD-NN-NS-NG | TA•AAARCNRNRCRACRNT | YP_001913948 |
| Xoo PXO99A | Tal8b | NI-HG-NS-HG-HG-HD-NS-NG-HD-NN-NG-HG-NG-HD-HG-HD-HD-NI-NN-NG | TA•N••CNTCRT•TC•CCART | YP_001913952 |
| Xoo PXO99A | Tal9a | HD-HD-HD-NG-N*-NN-HD-HD-N*-NI-NI-NN-HD-HI-ND-HD-NI-HD-NG-NG | TCCCT•RCC•AARC••CACTT | YP_001915089 |
| Xoo PXO99A | Tal9b | HD-HD-NN-NN-NG-NG-HD-NS-HG-HD-NG-N*-HD-HD-HD-N*-NN-NI-NN-HD-HI-ND-HD-HG-NN-HG-NG | TCCRRTTCN•CT•CCC•RARC••C•R•T | YP_001915093 |
| Xoo PXO99A | Tal9d | NI-NN-NI-HG-HG-NN-HG-HD-HG-HD-HD-HD-NG | TARA••R•C•CCCT | YP_001915101 |
| Xoo PXO99A | Tal9e | NN-HD-NS-NG-HD-NN-N*-NI-HD-NS-HD-NN-HD-NN-HD-NN-NN-NN-NN-NN-NN-HD-NG | TRCNTCR•ACNCRCRCRRRRRRRCT | YP_001915105 |
| Xoo C8 | PthC8a | NN-HD-HD-HD-NI-NI-NN-NI-HD-HD-HD-HG-NN-NN-HD-NS-NN-HD-N*-NS-N* | TRCCCAARACCC•RRCNRC•N• | ABY60855 |
| Xoo C8 | PthC8b | NI-HG-NI-NI-NI-NN-HD-NS-NN-NS-NN-HD-NN-NI-HD-NN-NS-NG | TA•AAARCNRNRCRACRNT | ACD11364 |
| Xoc | Avr/Pth3 | NS-HD-NI-NG-NI-HG-NG-HD-NN-NI-NG-HD-NN-NS-NN-NG-NN | TNCATATTCRATCRNRTR | AAW59492 |
| Xoc | Avr/Pth14 | NS-HD-NI-NG-NI-HG-NI-NI-NG-NG-HD-NN-NI-NG-HD-NN-NS-NN-NG-NN | TNCATATAATTCRATCRNRTR | AAW59493 |
| Xac 12879 | avrTaw | NI-NG-NI-NI-HD-NI-HD-HD-HD-NG-HD-NS-NI-HD-NI-NG-NI-NS-NG | TATAACACCCTCNACATANT | ACN39605 |

FIG. 16A

AvrBs3

Protein sequence:
MDPIRSRTPSPARELLPGPQPDGVQPTADRGVSPPAGGPLDGLPARRTMSRTRLPSPPAPSPAFSAGSFSDLLRQF
DPSLFNTSLFDSLPPFGAHHTEAATGEWDEVQSGLRAADAPPPTMRVAVTAARPPRAKPAPRRRAAQPSDASPAAQ
VDLRTLGYSQQQQEKIKPKVRSTVAQHHEALVGHGFTHAHIVALSQHPAALGTVAVKYQDMIAALPEATHEAIVGV
GKQWSGARALEALLTVAGELRGPPLQLDTGQLLKIAKRGGVTAVEAVHAWRNALTGAPLNLTPEQVVAIASHDGGK
QALETVQRLLPVLCQAHGLTPQQVVAIASNGGGKQALETVQRLLPVLCQAHGLTPQQVVAIASNSGGKQALETVQR
LLPVLCQAHGLTPEQVVAIASNGGGKQALETVQRLLPVLCQAHGLTPEQVVAIASNIGGKQALETVQALLPVLCQA
HGLTPEQVVAIASNIGGKQALETVQALLPVLCQAHGLTPEQVVAIASNIGGKQALETVQALLPVLCQAHGLTPEQV
VAIASHDGGKQALETVQRLLPVLCQAHGLTPEQVVAIASHDGGKQALETVQRLLPVLCQAHGLTPQQVVAIASNGG
GKQALETVQRLLPVLCQAHGLTPEQVVAIASNSGGKQALETVQALLPVLCQAHGLTPEQVVAIASNSGGKQALETV
QRLLPVLCQAHGLTPEQVVAIASHDGGKQALETVQRLLPVLCQAHGLTPEQVVAIASHDGGKQALETVQRLLPVLC
QAHGLTPEQVVAIASHDGGKQALETVQRLLPVLCQAHGLTPQQVVAIASNGGGRPALETVQRLLPVLCQAHGLTPE
QVVAIASHDGGKQALETVQRLLPVLCQAHGLTPQQVVAIASNGGRPALESIVAQLSRPDPALAALTNDHLVALAC
LGGRPALDAVKKGLPHAPALIKRTNRRIPERTSHRVADHAQVVRVLGFFQCHSHPAQAFDDAMTQFGMSRHGLLQL
PRRVGVTELEARSGTLPPASQRWDRILQASGMKRAKPSPTSTQTPDQASLHAFADSLERDLDAFSPMHEGDQTRAS
SRKRSRSDRAVTGPSAQQSFEVRVPEQRDALHLPLSWRVKRPRTSIGGGLPDPGTPTAADLAASSTVMREQDEDPF
AGAADDFPAFNEEELAWLMELLFQ Accession:
CAA34257.1

Organism:
Xanthomonas campestris pv. vesicatoria strain 71-21

Description of the AvrBs3 protein sequence:
N-Terminus: amino acid (AA) 1-288
MDPIRSRTPSPARELLPGPQPDGVQPTADRGVSPPAGGPLDGLPARRTMSRTRLPSPPAPSPAFSAGSFSDLLRQF
DPSLFNTSLFDSLPPFGAHHTEAATGEWDEVQSGLRAADAPPPTMRVAVTAARPPRAKPAPRRRAAQPSDASPAAQ
VDLRTLGYSQQQQEKIKPKVRSTVAQHHEALVGHGFTHAHIVALSQHPAALGTVAVKYQDMIAALPEATHEAIVGV
GKQWSGARALEALLTVAGELRGPPLQLDTGQLLKIAKRGGVTAVEAVHAWRNALTGAPLN Repeat 1: AA 289-322
LTPEQVVAIASHDGGKQALETVQRLLPVLCQAHG Repeat 2: AA 323-356
LTPQQVVAIASNGGGKQALETVQRLLPVLCQAHG Repeat 3: AA 357-390
LTPQQVVAIASNSGGKQALETVQRLLPVLCQAHG Repeat 4: AA 391-424
LTPEQVVAIASNGGGKQALETVQRLLPVLCQAHG Repeat 5: AA 425-458
LTPEQVVAIASNIGGKQALETVQALLPVLCQAHG Repeat 6: AA 459-492
LTPEQVVAIASNIGGKQALETVQALLPVLCQAHG Repeat 7: AA 493-526
LTPEQVVAIASNIGGKQALETVQALLPVLCQAHG Repeat 8: AA 527-560
LTPEQVVAIASHDGGKQALETVQRLLPVLCQAHG Repeat 9: AA 561-594
LTPEQVVAIASHDGGKQALETVQRLLPVLCQAHG Repeat 10: AA 595-628
LTPQQVVAIASNGGGKQALETVQRLLPVLCQAHG Repeat 11: AA 629-662
LTPEQVVAIASNSGGKQALETVQALLPVLCQAHG

FIG. 16B

Repeat 12: AA 663-696
LTPEQVVAIASNSGGKQALETVQRLLPVLCQAHG

Repeat 13: AA 697-730
LTPEQVVAIASHDGGKQALETVQRLLPVLCQAHG

Repeat 14: AA 731-764
LTPEQVVAIASHDGGKQALETVQRLLPVLCQAHG

Repeat 15: AA 765-798
LTPEQVVAIASHDGGKQALETVQRLLPVLCQAHG

Repeat 16: AA 799-832
LTPQQVVAIASNGGGRPALETVQRLLPVLCQAHG

Repeat 17: AA 833-866
LTPEQVVAIASHDGGKQALETVQRLLPVLCQAHG

Repeat 17.5: AA 867-886
LTPQQVVAIASNGGGRPALE

C-Terminus: AA 887-1164
SIVAQLSRPDPALAALTNDHLVALACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDRILQASGMKRAKPSPTSTQTPDQASL
HAFADSLERDLDAPSPMHEGDQTRASSRKRSRSDRAVTGPSAQQSFEVRVPEQRDALHLPLSWRVKRPRTSIGGGL
PDPGTPTAADLAASSTVMREQDEDPFAGAADDFPAFNEEELAWLMELLPQ Hax2

Protein sequence:
MDPIRSRTPSPARELLSGPQPDGVQPTADRGVSPPAGGPLDGLPARRTMSRTRLPSPPAPSPAFSADSFS
DLLRQFDPSLFNTSLFDSLPPFGAHHTEAATGEWDEVQSGLRAADAPPPTMRVAVTAARPPRAKPAPRRR
AAQPSDASPAAQVDLRTLGYSQQQQEKIKPKVRSTVAQHHEALVGHGFTHAHIVALSQHPAALGTVAVKY
QDMIAALPEATHEAIVGVGKQWSGARALEALLTVAGELRGPPLQLDTGQLLKIAKRGGVTAVEAVHAWRN
ALTGAPLNLTPEQVVAIASNNGGKQALETVQRLLPVLCQAPHDLTPEQVVAIASIGGGKQALETVQRLLP
VLCQAPHDLTPEQVVAIASNGGKQALETVQRLLPVLCQAPHCLTPEQVVAIASNIGGKQALETVQALLP
VLCQAPHCLTPEQVVAIASNGGGKQALETVQRLLPVLCQAPHDLTPEQVVAIASNGGGKQALETVQRLLP
VLCQAPHDLTPEQVVAIASHDGGKQALETVQRLLPVLCQAPHDLTPQQVVAIASNGGGKQALETVQRLLP
VLCQAPHDLTPEQVVAIASHDGGKQALETVQRLLPVLCQAPHDLTPEQVVAIASNIGGKQALETVQALLP
VLCQAPHCLTPEQVVAIASHDGGKQALETVQALLPVLCQAPHDLTPEQVVAIASNIGGKQALETVQRLLP
VLCQAPHDLTPEQVVAIASHDGGKQALETVQRLLPVLCQAPHDLTPEQVVAIASNGGGKQALETVQRLLP
VLCQAPHDLTPEQVVAIASHDGGKQALETVQRLLPVLCQAPHDLTPEQVVAIASNGGGKQALETVQRLLP
VLCQAPHDLTPEQVVAIASHDGGKQALETVQRLLPVLCQAPHDLTPEQVVAIASHDGGKQALETVQRLLP
VLCQAPHDLTPEQVVAIASNGGGKQALETVQRLLPVLCQAPHDLTPEQVVAIASNGGGKQALETVQALLP
VLCQAPHDLTPEQVVAIASNIGGKQALETVQRLLPVLCQAPHDLTPEQVVAIASNGGGKQALESIFAQLS
RPDPALAALTNDRLVALACIGGRSALNAVKDGLPNALTLIRRANSRIPERTSHLVADHTQVVRVLGFFQC
HSHPAQAFDRAMTQFGMSRHGLLQLFRRVGVTELEARSGTLPPASQRWDRILQASGMKRAKPSPTSTQTP
DQASLHAFADSLERDLDAPSPMHEGDQTRASSRKRSRSDRAVTGPSAQQSFEVRVPEQRDALHLPLLSWG
VKRPRTRIGGLLDPGTPMDADLVASSTVVWEQDADPFAGTADDFPAFNEEELAWLMELLPH Accession:
AAY43358.1

Organis:
Xanthomonas campestris pv. armoraciae strain 5

Description of the Hax2 protein sequence
N-Terminus: amino acid (AA) 1-288
MDPIRSRTPSPARELLSGPQPDGVQPTADRGVSPPAGGPLDGLPARRTMSRTRLPSPPAPSPAFSADSFSDLLRQF
DPSLFNTSLFDSLPPFGAHHTEAATGEWDEVQSGLRAADAPPPTMRVAVTAARPPRAKPAPRRRAAQPSDASPAAQ
VDLRTLGYSQQQQEKIKPKVRSTVAQHHEALVGHGFTHAHIVALSQHPAALGTVAVKYQDMIAALPEATHEAIVGV
GKQWSGARALEALLTVAGELRGPPLQLDTGQLLKIAKRGGVTAVEAVHAWRNALTGAPLN Repeat 1: AA 289-323
LTPEQVVAIASNNGGKQALETVQRLLPVLCQAPHD

FIG. 16C

Repeat 2: AA 324-358
LTPEQVVAIASIGGGKQALETVQRLLPVLCQAPHD

Repeat 3: AA 359-393
LTPEQVVAIASNGGGKQALETVQRLLPVLCQAPHC

Repeat 4: AA 394-428
LTPEQVVAIASNIGGKQALETVQALLPVLCQAPHC

Repeat 5: AA 429-463
LTPEQVVAIASNGGGKQALETVQRLLPVLCQAPHD

Repeat 6: AA 464-498
LTPEQVVAIASNGGGKQALETVQRLLPVLCQAPHD

Repeat 7: AA 499-533
LTPEQVVAIASHDGGKQALETVQRLLPVLCQAPHD

Repeat 8: AA 534-568
LTPQQVVAIASNGGGKQALETVQRLLPVLCQAPHD

Repeat 9: AA 569-603
LTPEQVVAIASHDGGKQALETVQRLLPVLCQAPHD

Repeat 10: AA 604-638
LTPEQVVAIASNIGGKQALETVQALLPVLCQAPHC

Repeat 11: AA 639-673
LTPEQVVAIASHDGGKQALETVQALLPVLCQAPHD

Repeat 12: AA 674-708
LTPEQVVAIASNIGGKQALETVQRLLPVLCQAPHD

Repeat 13: AA 709-743
LTREQVVAIASHDGGKQALETVQRLLPVLCQAPHD

Repeat 14: AA 744-778
LTPEQVVAIASNGGGKQALETVQRLLPVLCQAPHD

Repeat 15: AA 779-813
LTPEQVVAIASHDGGKQALETVQRLLPVLCQAPHD

Repeat 16: AA 814-848
LTPEQVVAIASNGGGKQALETVQRLLPVLCQAPHD

Repeat 17: AA 849-883
LTPEQVVAIASHDGGKQALETVQRLLPVLCQAPHD

Repeat 18: AA 884-918
LTPEQVVAIASHDGGKQALETVQRLLPVLCQAPHD

Repeat 19: AA 919-953
LTPEQVVAIASNGGGKQALETVQRLLPVLCQAPHD

Repeat 20: AA 954-988
LTPEQVVAIASNGGGKQALETVQALLPVLCQAPHD

Repeat 21: AA 989-1023
LTPEQVVAIASNIGGKQALETVQRLLPVLCQAPHD

Repeat 21.5: AA 1024-1043
LTPEQVVAIASNGGGKQALE

C-Terminus: AA 1044-1321
SIFAQLSRPDPALAALTNDRLVALACIGGRSALNAVKDGLPNALTLIRRANSRIPERTSHLVADHTQVVRVLGFFQ
CHSHPAQAFDEAMTQFGMSRHGLLQLFRRVGVTELEARSGTLPPASQRWDRILQASGMKRAKPSPTSTQTPDQASL
HAFADSLERDLDAPSPMHEGDQTRASSRKRSRSDRAVTGPSAQQSFEVRVPEQRDALHLPLLSWGVKRPRTRIGGL
LDPGTPMDADLVASSTVVWEQDADPFAGTADDFPAFNEERLAWLMELLPH

FIG. 16B

Hax3

Protein sequence:
MDPIRSRTPSPARELLSGPQPDGVQPTADRGVSPPAGGPLDGLPARRTMSRTRLPSPPAPSPAFSADSFS
DLLRQFDPSLFNTSLFDSLPPFGAHHTEAATGEWDEVQSGLRAADAPPPTMRVAVTAARPPRAKPAPRRR
AAQPSDASPAAQVDLRTLGYSQQQQEKIKPKVRSTVAQHHEALVGHGFTHAHIVALSQHPAALGTVAVKY
QDMIAALPEATHEAIVGVGKQWSGARALEALLTVAGELRGPPIQLDTGQLLKIAKRGGVTAVEAVHAWRN
ALTGAPLNLTPEQVVAIASNIGGKQALETVQRLLPVLCQAHGLTPQQVVAIASHDGGKQALETVQRLLPV
LCQAHGLTPEQVVAIASNIGGKQALETVQALLPVLCQAHGLTPEQVVAIASHDGGKQALETVQRLLPVLC
QAHGLTPQQVVAIASHDGGKQALETVQRLLPVLCQAHGLTPQQVVAIASHDGGKQALETVQRLLPVLCQA
HGLTPQQVVAIASNSGGKQALETVQRLLPVLCQAHGLTPQQVVAIASNSGGKQALETVQRLLPVLCQAHG
LTPQQVVAIASNSGGKQALETVQRLLPVLCQAHGLTPEQVVAIASHDGGKQALETVQRLLPVLCQAHGLT
PEQVVAIASNIGGKQALETVQRLLPVLCQAHGLTPQQVVAIASNGGGRPALESIVAQLSRPDPALAALTN
DHLVALACLGGRPALDAVKKGLPHAPALIKRTNRRIPERTSHRVADHAQVVRVLGFFQCHSHPAQAFDDA
MTQFGMSRHGLLQLFRRVGVTELEARSGTLPPASQRWDRILQASGMKRAKPSPTSTQTPDQASLHAFADS
LERDLDAPSPMHEGDQTRASSRKRSRSDRAVTGPSAQQSFEVRVPEQRDALHLPLLSWGVKRPRTRIGGL
LDPGTPMDADLVASSTVVWEQDADPFAGTADDFPAFNEEELAWLMELLPQ Accession:
AAY43359.1

Organism:
Xanthomonas campestris pv. armoraciae strain 5

Description of the Hax3 protein sequence:
N-Terminus: amino acid (AA) 1-288
MDPIRSRTPSPARELLSGPQPDGVQPTADRGVSPPAGGPLDGLPARRTMSRTRLPSPPAPSPAFSADSFSDLLRQF
DPSLFNTSLFDSLPPFGAHHTEAATGEWDEVQSGLRAADAPPPTMRVAVTAARPPRAKPAPRRRAAQPSDASPAAQ
VDLRTLGYSQQQQEKIKPKVRSTVAQHHEALVGHGFTHAHIVALSQHPAALGTVAVKYQDMIAALPEATHEAIVGV
GKQWSGARALEALLTVAGELRGPPLQLDTGQLLKIAKRGGVTAVEAVHAWRNALTGAPLN Repeat 1: AA 289-322
LTPEQVVAIASNIGGKQALETVQRLLPVLCQAHG Repeat 2: AA 323-356
LTPQQVVAIASHDGGKQALETVQRLLPVLCQAHG Repeat 3: AA 357-390
LTPEQVVAIASNIGGKQALETVQALLPVLCQAHG Repeat 4: AA 391-424
LTPEQVVAIASHDGGKQALETVQRLLPVLCQAHG Repeat 5: AA 425-458
LTPQQVVAIASHDGGKQALETVQRLLPVLCQAHG Repeat 6: AA 459-492
LTPQQVVAIASHDGGKQALETVQRLLPVLCQAHG Repeat 7: AA 493-526
LTPQQVVAIASNSGGKQALETVQRLLPVLCQAHG Repeat 8: AA 527-560
LTPQQVVAIASNSGGKQALETVQRLLPVLCQAHG Repeat 9: AA 561-594
LTPQQVVAIASNSGGKQALETVQRLLPVLCQAHG Repeat 10: AA 595-628
LTPEQVVAIASHDGGKQALETVQRLLPVLCQAHG Repeat 11: AA 629-662
LTPEQVVAIASNIGGKQALETVQRLLPVLCQAHG Repeat 11.5: AA 663-682

FIG. 16K

LTPQQVVAIASNGGGRPALE

C-Terminus: AA 683-960
SIVAQLSRPDPALAALTNDHLVALACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDRILQASGMKRAKPSPTSTQTPDQASL
HAFADSLERDLDAPSPMHEGDQTRASSRKRSRSDRAVTGPSAQQSFEVRVPEQRDALHLPLLSWGVKRPRTRIGGL
LDPGTPMDADLVASSTVVWEQDADPFAGTADDFPAFNEEELAWLMELLPQ

---

Hax4

Protein sequence:
MDPIRSRTPSPARELLSGPQPDGVQPTADRGVSPPAGGPLDGLPARRTMSRTRLPSPPAPSPAFSADSFS
DLLRQFDPSLFNTSLFDSLPPFGAHHTEAATGEWDEVQSGLRAADAPPPTMRVAVTAARPPRAKPAPRRR
AAQPSDASPAAQVDLRTLGYSQQQQEKIKPKVRSTVAQHHEALVGHGFTHAHIVALSQHPAALGTVAVKY
QDMIAALPEATHEAIVGVGKQWSGARALEALLTVAGELRGPPLQLDTGQLLKIAKRGGVTAVEAVHAWRN
ALTGAPLNLTPEQVVAIASNIGGKQALETVQALLPVLCQAHGLTPQQVVAIASHDGGKQALETVQRLLPV
LCQAHGLTPEQVVAIASHDGGKQALETVQRLLPVLCQAHGLTPQQVVAIASNGGGKQALETVQRLLPVLC
QAHGLTPEQVVAIASNSGGKQALETVQALLPVLCQAHGLTPQQVVAIASNSGGKQALETVQALLPVLCQA
HGLTPEQVVAIASNIGGKQALETVQRLLPVLCQAHGLTPQQVVAIASHDGGKQALETVQRLLPVLCQAHG
LTPQQVVAIASNGGGKQALETVQRLLPVLCQAHGLTPEQVVAIASNIGGKQALETVQALLPVLCQAHGLT
PQQVVAIASNSGGKQALETVQALLPVLCQAHGLTPEQVVAIASNIGGKQALETVQRLLPVLCQAHGLTPE
QVVAIASNGGGKQALETVQRLLPVLCQAHGLTPEQVVAIASNIGGKQALETVQALLPVLCQAHGLTPEQV
VAIASNGGGRPALESIVAQLSRPDPALAALTNDHLVALACLGGRPALDAVKKGLPHAPALIKRTNRRIPE
RTSHRVADHAQVVRVLGFFQCHSHPAQAFDDAMTQFGMSRHGLLQLFRRVGVTELEARSGTLPPASQRWD
RILQASGMKRAKPSPTSTQTPDQASLHAFADSLERDLDAPSPMHEGDQTRASSRKRSRSDRAVTGPSAQQ
SFEVRVPEQRDALHLPLSWRVKRPRTSIGGGLPDPGTPTAADLAASSTVMREQDEDPFAGAADDFPAFNE
EELAWLMELLPQ Accession:
AAY43360.1

Organism:
Xanthomonas campestris pv. armoraciae strain 5

Description of the Hax4 protein sequence:
N-Terminus: amino acid (AA) 1-288
MDPIRSRTPSPARELLSGPQPDGVQPTADRGVSPPAGGPLDGLPARRTMSRTRLPSPPAPSPAFSADSFSDLLRQF
DPSLFNTSLFDSLPPFGAHHTEAATGEWDEVQSGLRAADAPPPTMRVAVTAARPPRAKPAPRRRAAQPSDASPAAQ
VDLRTLGYSQQQQEKIKPKVRSTVAQHHEALVGHGFTHAHIVALSQHPAALGTVAVKYQDMIAALPEATHEAIVGV
GKQWSGARALEALLTVAGELRGPPLQLDTGQLLKIAKRGGVTAVEAVHAWRNALTGAPLN Repeat 1: AA 289-322
LTPEQVVAIASNIGGKQALETVQALLPVLCQAHG Repeat 2: AA 323-356
LTPQQVVAIASHDGGKQALETVQRLLPVLCQAHG Repeat 3: AA 357-390
LTPEQVVAIASHDGGKQALETVQRLLPVLCQAHG Repeat 4: AA 391-424
LTPQQVVAIASNGGGKQALETVQRLLPVLCQAHG Repeat 5: AA 425-458
LTPEQVVAIASNSGGKQALETVQALLPVLCQAHG Repeat 6: AA 459-492
LTPQQVVAIASNSGGKQALETVQALLPVLCQAHG Repeat 7: AA 493-526
LTPEQVVAIASNIGGKQALETVQRLLPVLCQAHG Repeat 8: AA 527-560
LTPQQVVAIASHDGGKQALETVQRLLPVLCQAHG Repeat 9: AA 561-594

FIG. 16F

LTPQQVVAIASNGGGKQALETVQRLLPVLCQAHG

Repeat 10: AA 595-628
LTPEQVVAIASNIGGKQALETVQALLPVLCQAHG

Repeat 11: AA 629-662
LTPQQVVAIASNSGGKQALETVQALLPVLCQAHG

Repeat 12: AA 663-696
LTPEQVVAIASNIGGKQALETVQRLLPVLCQAHG

Repeat 13: AA 697-730
LTPEQVVAIASNGGGKQALETVQRLLPVLCQAHG

Repeat 14: AA 731-764
LTPEQVVAIASNIGGKQALETVQALLPVLCQAHG

Repeat 14.5: AA 765-784
LTPEQVVAIASNGGGRPALE

C-Terminus: AA 785-1062
SIVAQLSRPDPALAALTNDHLVALACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDRILQASGMKRAKFSPTSTQTPDQASL
HAFADSLERDLDAPSPMHEGDQTRASSRKRSRSDRAVTGPSAQQSFEVRVPEQRDALHLPLSWRVKRPRTSIGGGL
PDPGTPTAADLAASSTVMREQDEDPFAGAADDFPAFNEEEIAWLMBLLPQ FIG. 17A
| | | | | | | | | | | | | | | |
|---|---|---|---|---|---|---|---|---|---|---|---|---|---|---|
| Hax4 repeats | 0 | 1 | 2 | 3 | 4 | 5 | 6 | 7 | 8 | 9 | 10 | 11 | 12 | 13 14 14.5 |
| | | NI | HD | HD | NG | NS | NS | NI | HD | NG | NI | NS | NI | NG NI NG |
| Hax4 box | | T | A | C | C | T | A | A | A | C | T | A | A | A T A T |
| Hax4(mut) box | | T | A | C | C | [A] | A | A | A | C | [A] | A | A | [A] A [A] |
FIG. 17B
| | | | | | | | | | | | | |
|---|---|---|---|---|---|---|---|---|---|---|---|---|
| ARTBs4 repeats | 0 | 1 | 2 | 3 | 4 | 5 | 6 | 7 | 8 | 9 | 10 | 11 11.5 |
| | | NG | NN | NG | NI | NG | NI | NG | NI | NI | HD | NG NG |
| ARTBs4 box | | T | T | G | T | A | T | A | T | A | A | C T T |
FIG. 17C
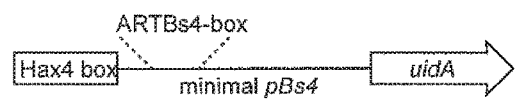
FIG. 17D
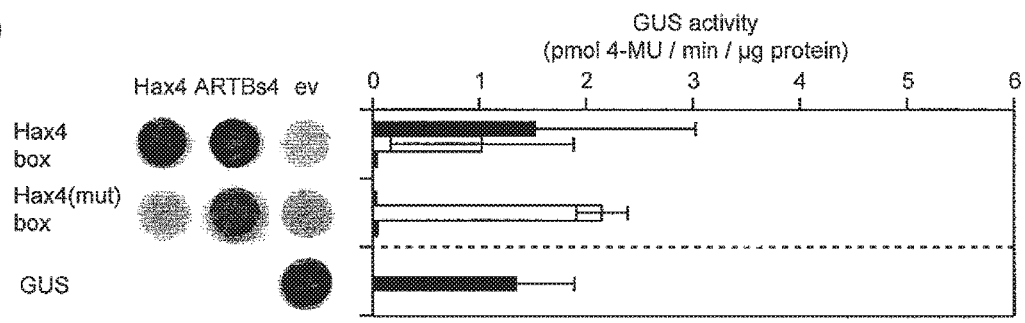

|  | 6 Hax3 repeats | | | | | | 6 x same repeat | | | | | |
|---|---|---|---|---|---|---|---|---|---|---|---|---|
| TAL effector: | | | | | | | | | | | | |
| Repeats | NI | HD | NI | HD | HD | HD | XX | XX | XX | XX | XX | XX |
| Target boxes: | | | | | | | | | | | | |
| Poly-A box | T | A | C | A | C | C | C | A | A | A | A | A | A |
| Poly-C box | T | A | C | A | C | C | C | C | C | C | C | C | C |
| Poly-G box | T | A | C | A | C | C | C | G | G | G | G | G | G |
| Poly-T box | T | A | C | A | C | C | C | T | T | T | T | T | T |

FIG. 20

MODULAR DNA-BINDING DOMAINS AND METHODS OF USE

CROSS-REFERENCE TO RELATED APPLICATIONS

This application is a divisional of U.S. application Ser. No. 15/222,498, filed Jul. 28, 2016, now U.S. Pat. No. 9,809,628, which is a divisional of U.S. application Ser. No. 14/625,698, filed Feb. 19, 2015, now U.S. Pat. No. 9,453,054, which is a continuation of U.S. Application No. 14/153,241, filed Jan. 13, 2014, now U.S. Pat. No. 9,017,967, which is a continuation of U.S. application Ser. No. 13/755,826, filed Jan. 31, 2013, now abandoned, which is a continuation of U.S. application Ser. No. 13/019,526, filed Feb. 2, 2011, now abandoned, which is a continuation-in-part of U.S. application Ser. No. 13/016,297, filed Jan. 28, 2011, now U.S. Pat. No. 9,353,378, which is a continuation of International Application PCT/IB2010/000154, filed Jan. 12, 2010, which designates the U.S and was published by the International Bureau in English on Jul. 15, 2010, and which claims the benefit of U.S. Provisional Patent Application No. 61/225,043, filed Jul. 13, 2009, European (EP) Patent Application No. 09165328.7, filed Jul. 13, 2009, German (DE) Patent Application No. 102009004659.3, filed Jan. 12, 2009; all of which are hereby incorporated herein in their entirety by reference.

TECHNICAL FIELD OF THE INVENTION

The present invention refers to methods for selectively recognizing a base pair in a target DNA sequence by a polypeptide, to modified polypeptides which specifically recognize one or more base pairs in a target DNA sequence and, to DNA which is modified so that it can be specifically recognized by a polypeptide and to uses of the polypeptide and DNA in specific DNA targeting as well as to methods of modulating expression of target genes in a cell.

BACKGROUND OF THE INVENTION

Phytopathogenic bacteria of the genus Xanthomonas cause severe diseases on many important crop plants. The bacteria translocate an arsenal of effectors including members of the large transcription activator-like (TAL)/AvrBs3-like effector family via the type III secretion system into plant cells (Kay & Bonas (2009) Curr. Opin. Microbiol. 12:37-43, White & Yang (2009) Plant Physiol. doi:10.1104/pp.1109.139360; Schornack et al. (2006) J. Plant Physiol. 163:256-272). TAL effectors, key virulence factors of Xanthomonas, contain a central domain of tandem repeats, nuclear localization signals (NLSs), and an activation domain (AD) and act as transcription factors in plant cells (Kay et al. (2007) Science 318:648-651; Römer et. al (2007) Science 318:645-648; Gu et al. (2005) Nature 435, 1122-1125; FIG. 1a). The type member of this effector family, AvrBs3 from Xanthomonas campestris pv. vesicatoria, contains 17.5 repeats and induces expression of UPA (upregulated by AvrBs3) genes including the Bs3 resistance gene in pepper plants (Kay et al. (2007) Science 318:648-651; Römer et al. (2007) Science 318:645-648; Marois et al. (2002) Mol. Plant-Microbe Interact. 15:637-646). The number and order of repeats in a TAL effector determine its specific activity (Herbers et al. (1992) Nature 356:172-174). The repeats were shown to be essential for DNA-binding of AvrBs3 and constitute a novel DNA-binding domain (Kay et al. (2007) Science 318:648-651). How this domain contacts DNA and what determines specificity has remained enigmatic.

Selective gene expression is mediated via the interaction of protein transcription factors with specific nucleotide sequences within the regulatory region of the gene. The manner in which DNA-binding protein domains are able to discriminate between different DNA sequences is an important question in understanding crucial processes such as the control of gene expression in differentiation and development.

The ability to specifically design and generate DNA-binding domains that recognize a desired DNA target is highly desirable in biotechnology. Such ability can be useful for the development of custom transcription factors with the ability to modulate gene expression upon target DNA binding. Examples include the extensive work done with the design of custom zinc finger DNA-binding proteins specific for a desired target DNA sequence (Choo et al. (1994) Nature 372:645; Pomerantz et al., (1995) Science 267:93-96; Liu et al., Proc. Natl. Acad. Sci. USA 94:5525-5530 (1997); Guan et al. (2002) Proc. Natl. Acad. Sci. USA 99:13296-13301; U.S. Pat. Nos. 7,273,923; 7,220,719). Furthermore, polypeptides containing designer DNA-binding domains can be utilized to modify the actual target DNA sequence by the inclusion of DNA modifying domains, such as a nuclease catalytic domain, within the polypeptide. Examples of such include the DNA binding domain of a meganuclease/homing endonuclease DNA recognition site in combination with a non-specific nuclease domain (see US Pat. Appl. 2007/0141038), modified meganuclease DNA recognition site and/or nuclease domains from the same or different meganucleases (see U.S. Pat. App. Pub. 20090271881), and zinc finger domains in combination with a domain with nuclease activity, typically from a type IIS restriction endonuclease such as FokI (Bibikova et al. (2003) Science 300:764; Urnov et al. (2005) Nature 435, 646; Skukla, et al. (2009) Nature 459, 437-441; Townsend et al. (2009) Nature 459:442445; Kim et al. (1996) Proc. Natl Acad. Sci USA 93:1156-1160; U.S. Pat. No. 7,163,824). The current methods utilized for identifying custom zinc finger DNA-binding domains employ combinatorial selection-based methods utilizing large randomized libraries (typically >10$^8$ in size) to generate multi-finger domains with desired DNA specificity (Greisman & Pabo (1997) Science 275:657-661; Hurt et al. (2003) Proc Natl Acad Sci USA 100:12271-12276; Isalan et al. (2001) Nat Biotechnol 19:656-660. Such methods are time intensive, technically demanding and potentially quite costly. The identification of a simple recognition code for the engineering of DNA-binding polypeptides would represent a significant advancement over the current methods for designing DNA-binding domains that recognize a desired nucleotide target.

BRIEF SUMMARY OF THE INVENTION

The present invention provides a method for producing a polypeptide that selectively recognizes a base pair in a DNA sequence, the method comprising synthesizing a polypeptide comprising a repeat domain, wherein the repeat domain comprises at least one repeat unit derived from a transcription activator-like (TAL) effector, wherein the repeat unit comprises a hypervariable region which determines recognition of a base pair in the DNA sequence, wherein the repeat unit is responsible for the recognition of one base pair in the DNA sequence. These polypeptides of the invention comprise repeat units of the present invention and can be constructed by a modular approach by preassembling repeat units in target vectors that can subsequently be assembled into a final destination vector. The invention provides the polypeptide produced the this method as well as DNA sequences encoding the polypeptides and host organisms and cells comprising such DNA sequences.

The present invention provides a method for selectively recognizing a base pair in a target DNA sequence by a polypeptide wherein said polypeptide comprises at least a repeat domain comprising repeat units wherein in said repeat units each comprise a hypervariable region which determines recognition of a base pair in said target DNA sequence.

More specifically, the inventors have determined those amino acids in a DNA-binding polypeptide responsible for selective recognition of base pairs in a target DNA sequence. With elucidation of the recognition code, a general principle for recognizing specific base pairs in a target DNA sequence by selected amino acids in a polypeptide has been determined. The inventors have found that distinct types of repeat units that are part of a repeat unit array of varying length have the capacity to recognize one defined/specific base pair. Within each repeat unit forming a repeat domain, a hypervariable region is responsible for the specific recognition of a base pair in a target DNA sequence.

Thus, the present invention provides not only a method for selectively recognizing a base pair in a target DNA sequence by a polypeptide comprising at least a repeat domain comprising repeat units but also methods wherein target DNA sequences can be generated which are selectively recognized by repeat domains in a polypeptide.

The invention also provides for a method for constructing polypeptides that recognize specific DNA sequences. These polypeptides of the invention comprise repeat units of the present invention and can be constructed by a modular approach by preassembling repeat units in target vectors that can subsequently be assembled into a final destination vector.

The invention also provides a method for targeted modulation of gene expression by constructing modular repeat units specific for a target DNA sequence of interest, modifying a polypeptide by the addition of said repeat units so as to enable said polypeptide to now recognize the target DNA, introducing or expressing said modified polypeptide in a prokaryotic or eurkaryotic cell so as to enable said modified polypeptide to recognize the target DNA sequence, and modulation of the expression of said target gene in said cell as a result of such recognition.

The invention also provides for a method for directed modification of a target DNA sequence by the construction of a polypeptide including at least a repeat domain of the present invention that recognizes said target DNA sequence and that said polypeptide also contains a functional domain capable of modifying the target DNA (such as via site specific recombination, restriction or integration of donor target sequences) thereby enabling targeted DNA modifications in complex genomes.

The invention further provides for the production of modified polypeptides including at least a repeat domain comprising repeat units wherein a hypervariable region within each of the repeat units determines selective recognition of a base pair in a target DNA sequence.

In a further embodiment of the invention, DNA is provided which encodes for a polypeptide containing a repeat domain as described above.

In a still further embodiment of the invention, DNA is provided which is modified to include one or more base pairs located in a target DNA sequence so that said each of the base pairs can be specifically recognized by a polypeptide including a repeat domain having corresponding repeat units, each repeat unit comprising a hypervariable region which determines recognition of the corresponding base pair in said DNA.

In a still further embodiment of the invention, uses of those polypeptides and DNAs are provided. Additionally provided are plants, plant parts, seeds, plant cells and other non-human host cells transformed with the isolated nucleic acid molecules of the present invention and the proteins or polypeptides encoded by the coding sequences of the present invention. Still further, the polypeptides and DNA described herein can be introduced into animal and human cells as well as cells of other organisms like fungi or plants.

In summary, the invention focuses on a method for selectively recognizing base pairs in a target DNA sequence by a polypeptide wherein said polypeptide comprises at least a repeat domain comprising repeat units wherein each repeat unit contains a hypervariable region which determines recognition of a base pair in said target DNA sequence wherein consecutive repeat units correspond to consecutive base pairs in said target DNA sequence.

BRIEF DESCRIPTION OF THE FIGURES

FIGS. 1A-1D. Model for DNA-Target Specificity of TAL Effectors.

FIG. 1A. TAL effectors contain central tandem repeat units (red), nuclear localization signals (NLS) and an activation domain (AD). Amino acid sequence of the first repeat of AvrBs3 (SEQ ID NO:1). Hypervariable amino acids 12 and 13 are shaded in gray.

FIG. 1B. Hypervariable amino acids at position 12 and 13 of the 17.5 AvrBs3 repeat units are aligned to the UPA-box consensus (SEQ ID NO:2).

FIG. 1C. Repeat units of TAL effectors and predicted target sequences in promoters of induced genes were aligned manually. Nucleotides in the upper DNA strand that correspond to the hypervariable amino acids in each repeat were counted based on the following combinations of eight effectors and experimentally identified target genes: AvrBs3/Bs3, UPA10, UPA12, UPA14, UPA19, UPA20, UPA21, UPA23, UPA25, AvrBs3Δrep 16/Bs3-E, AvrBs3Δrep109/Bs3, AvrHah1/Bs3, AvrXa27/Xa27, PthXo1/Xa13, PthXo6/Os-TFX1, PthXo7/OsTFIIAγ1 (see FIG. 5). Predominant combinations (n>4) are shaded in gray. An asterisk indicates that amino acid 13 is missing in this repeat type.

FIG. 1D. DNA target specificity code (R=A/G; N=A/C/G/T) of repeat types based on the hypervariable amino acids 12 and 13 (experimentally proven in this study).

FIGS. 2A-2C. Target DNA Sequences of Hax2, Hax3, and Hax4.

FIG. 2A. Amino acids 12 and 13 of the Hax2, Hax3, and Hax4 repeat units and predicted target DNA specificities (Hax-box) for Hax2-box (SEQ ID NO:3), Hax3-box (SEQ ID NO:4) and Hax4-box (SEQ ID NO:5).

FIG. 2B. Hax-boxes were cloned in front of the minimal Bs4 promoter into a GUS reporter vector.

FIG. 2C. Specific inducibility of the Hax-boxes by Hax effectors. GUS reporter constructs were codelivered via *A. tumefaciens* into *N. benthamiana* with 35S-driven hax2, hax3, hax4, and empty T-DNA (−), respectively (error bars indicate SD; n=3 samples; 4-MU, 4-methyl-umbelliferone). 35S::uidA (+) served as control. Leaf discs were stained with X-Gluc (5-bromo-4-chloro-3-indolyl-β-D-glucuronide).

FIG. 3A. Hax4- and ArtX-box-derivatives were cloned in front of the minimal Bs4 promoter into a GUS reporter vector.

FIG. 3B. Specificity of NG-, HD-, NI-, and NS-repeat units. Hax4-inducibility of Hax4-box (SEQ ID NO:5) derivatives permutated in repeat type target bases (gray background). Hax4-box derivative sequences are listed from top to bottom in order as SEQ ID NOs:6-17.

FIG. 3C. Specificity of NN-repeat units. Artificial effector ArtX1 (SEQ ID NO:18) and predicted target DNA sequences. ArtX1-inducibility of ArtX1 box derivatives permutated in NN-repeat target bases (gray background). ArtX1-box derivative sequences are listed from top to bottom in order as SEQ ID NOs:19-21.

FIG. 3D. Artificial effectors ArtX2 and ArtX3 and derived DNA target sequences ArtX2-box (SEQ ID NO:22) and ArtX3-box (SEQ ID NO:23).

FIG. 3E. Specific inducibility of ArtX-boxes by artificial effectors.

For FIG. 3A-3E, the GUS reporter constructs were co-delivered via *A. tumefaciens* into *N. benthamiana* with 35S-driven hax4, artX1, artX2, or artX3 genes, and empty T-DNA (−), respectively. 35S::uidA (+) served as control. Leaf discs were stained with X-Gluc. For quantitative data see FIG. 11.

Figure 4A:
Figure 4C:
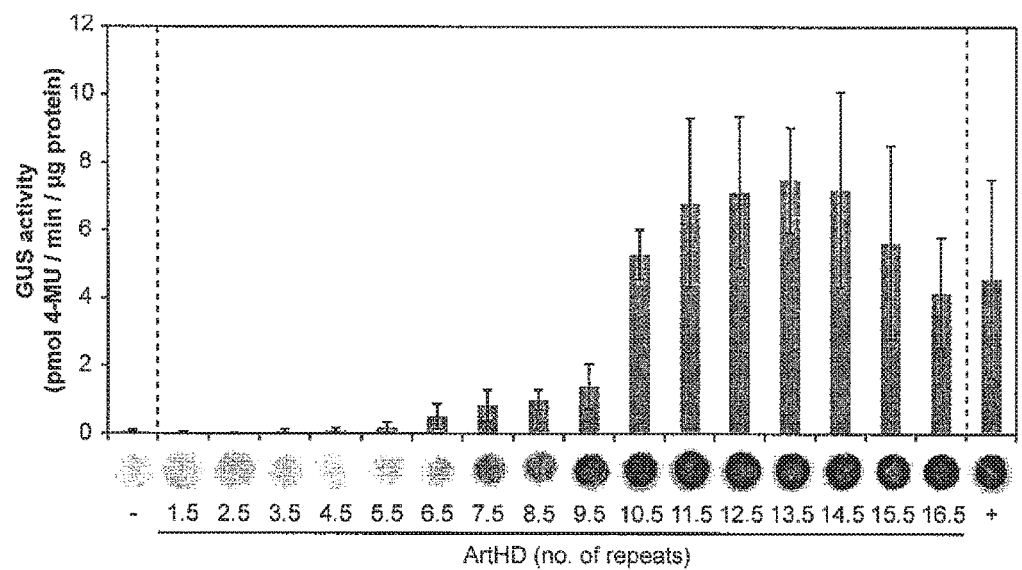

FIGS. 4A-4C. A Minimal Number of Repeat Units is Required for Transcriptional Activation.

FIG. 4A. Artificial ArtHD effectors with different numbers (0.5-15.5) of HD-repeat units (total 1.5 to 16.5 repeat units) and the ArtHD-box sequence (SEQ ID NO:24).

FIG. 4B. An ArtHD target box consisting of TA and 17 C was cloned in front of the minimal Bs4 promoter into a GUS reporter vector.

FIG. 4C. Promoter activation by ArtHD effectors with different number of repeat units. 35S-driven effector gene or empty T-DNA (−) were codelivered via *A. tumefaciens* with the GUS-reporter construct into *N. benthamiana* (error bars indicate SD; n=3 samples; 4-MU). 35S::uidA (+) served as control. Leaf discs were stained with X-Gluc.

FIGS. 5A-5F. Alignment of DNA Target Sequences in Promoters of Induced Genes with the Hypervariable Amino Acids 12 and 13 of TAL Effector Repeat Units.

FIG. 5A. Repeat units of AvrBs3, AvrBs3Δrep16, AvrBs3Δrep109, and AvrHah1 were aligned to the UPA-box (SEQ ID NO:25) in the promoter of the pepper ECW-30R Bs3 gene (accession: EU078684). AvrBs3Δrep16 and AvrBs3Δrep109 are deletion derivatives of AvrBs3 in which repeat units 11-14 and repeat units 12-14 were deleted, respectively. AvrBs3, AvrBs3Δrep109, and AvrHah1, but not AvrBs3Δrep16 induce the HR in ECW-30R plants.

FIG. 5B. Repeat units of AvrBs3, AvrBs3Δrep16, AvrBs3Δrep109, and AvrHah1 were aligned to the non-functional UPA-box (SEQ ID NO:26) in the promoter of the pepper ECW Bs3-E gene (accession: EU078683). AvrBs3Δrep16, but not AvrBs3, AvrBs3Δrep109, or AvrHah1 induce the HR in pepper ECW plants.

FIG. 5C. Repeat units of AvrXa27 were aligned to a putative target sequence in the promoter of the rice Xa27 gene (SEQ ID NO:27). Xa27 (accession: AY986492) is induced by AvrXa27 in rice cultivar IRBB27 leading to an HR, but not xa27 (accession: AY986491) (SEQ ID NO:28) in rice cultivar IR24.

FIG. 5D. Repeat units of PthXo1 were aligned to a putative target sequence in the promoter of the rice Xa13/Os8N3 gene (SEQ ID NO:29). Xa13 (accession: DQ421396) is induced by PthXo1 in rice cultivar IR24 leading to susceptibility, but not xa13 (accession: DQ421394) (SEQ ID NO:30) in rice cultivar IRBB13.

FIG. 5E. Repeat units of PthXo6 were aligned to a putative target sequence in the promoter of the rice OsTFX1 gene (accession: AK108319) (SEQ ID NO:31). OsTFX1 is induced by PthXo6 in rice cultivar IR24.

FIG. 5F. Repeat units of PthXo7 were aligned to a putative target sequence in the promoter of the rice OsTFIIAγ1 gene (CB097192) (SEQ ID NO:32). OsTFIIAγ1 is induced by PthXo7 in rice cultivar IR24.

In FIGS. 5A-5F, the numbers above the DNA sequences indicate nucleotide distance to the first ATG in the coding region. Repeat/base combinations not matching our predicted target specificity (amino acids 12/13: NI=A; HD=C; NG=T; NS=A/C/G/T; NN=A/G; IG=T) are coloured in red. Repeat units with unknown target DNA specificity are coloured in green.

FIGS. 6A-6B. The DNA Region Protected by AvrBs3Δrep16 is 4 bp Shorter than with AvrBs3.

Figure 7A:
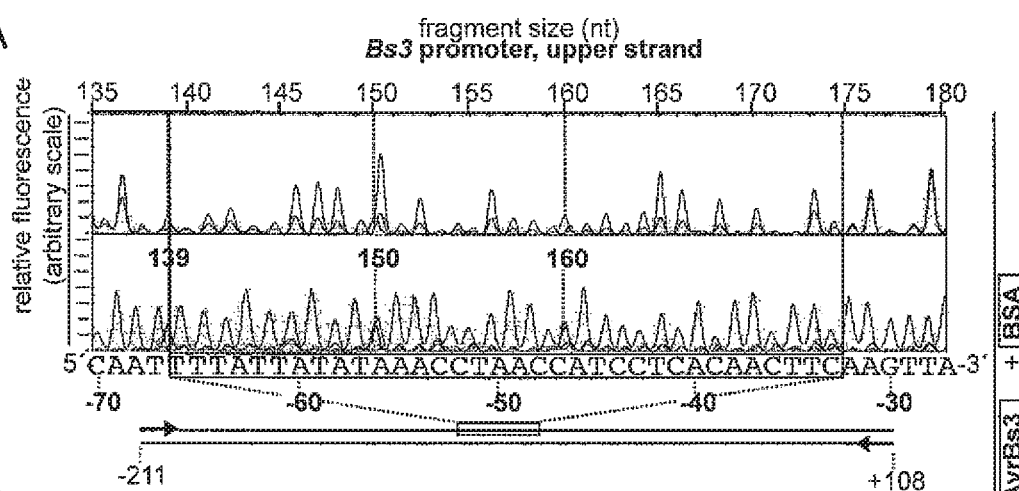
Figure 7B:
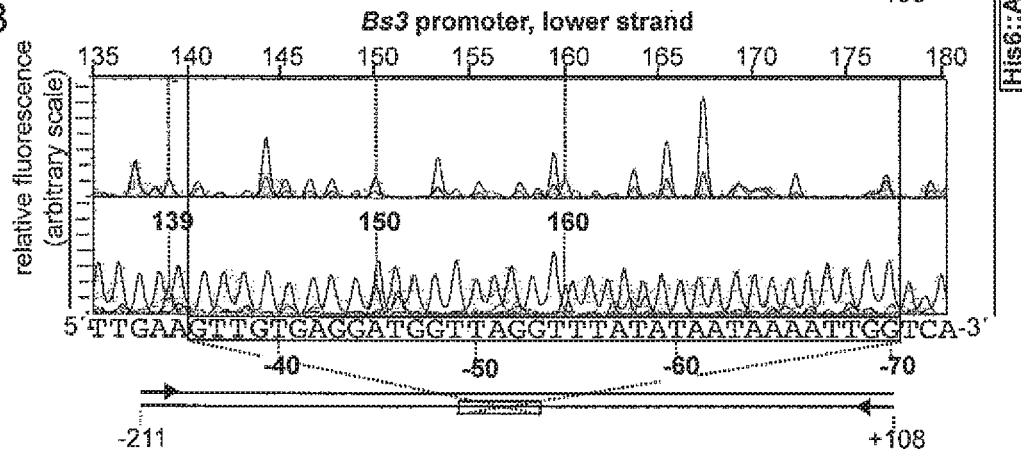

Summary of DNaseI footprint analyses with AvrBs3 and AvrBs3Δrep16 (see FIGS. 7, 8).

FIG. 6A. Bs3 (top) and Bs3-E (middle) promoter sequences protected by AvrBs3 and AvrBs3Δrep16, respectively. DNaseI footprinting revealed that AvrBs3 protected 37 nucleotides of the sense strand (SEQ ID NO:33) and 36 nucleotides of the antisense strand (SEQ ID NO:34) of the Bs3 promoter, and AvrBs3Δrep16 protected 30 nucleotides of the sense strand (SEQ ID NO:35) and 32 nucleotides of the antisense strand (SEQ ID NO:36) of the Bs3-E promoter. The UPA-box and the predicted AvrBs3Δrep16-box are underlined. UPA20-ubm-r16 (lower part) promoter sequences protected by AvrBs3 and AvrBs3Δrep16. The UPA20-ubmr16 promoter is a UPA20 promoter derivative with a 2 bp substitution (GA to CT, bold italic) that results in recognition by both, AvrBs3 and AvrBs3Δrep16. DNaseI footprinting revealed that 35 nucleotides of the sense strand (SEQ ID NO:37) and 34 nucleotides of the antisense strand (SEQ ID NO:38) are protected by AvrBs3 (UPA-box is underlined), and 31 nucleotides of the sense strand (SEQ ID NO:39) and 32 nucleotides of the antisense strand (SEQ ID NO:40) are protected by AvrBs3Δrep16 (AvrBs3Δrep16-box is underlined). DNA regions shaded in green (AvrBs3) or red (AvrBs3Δrep16) refer to the core footprints which were protected by AvrBs3 and AvrBs3Δrep16, respectively, in every experiment, even with low protein amounts (equal molarity of DNA and protein dimers). DNA regions shaded in gray refer to nucleotides which were not protected in all of the 4 experiments at all protein concentrations by the given proteins. Please note that the 5'ends of the AvrBs3- and AvrBs3Δrep16-protected regions are identical. Dashed vertical lines indicate the differences between the 3'ends of the AvrBs3- and AvrBs3Δrep16-protected promoter regions which corroborates our model that one repeat contacts one base pair in the DNA.

FIG. 6B. Alignment of AvrBs3 and AvrBs3Δrep16 target DNA sequences in the UPA20-ubm-r16 promoter (UPA20-ubm-r16-box) (SEQ ID NO:41) with AvrBs3 and AvrBs3Δrep16 repeat regions (hypervariable amino acids at position 12 and 13). Repeat/base combinations not matching our predicted target specificity (amino acids 12/13: NI=A; HD=C; NG=T; NS=A/C/G/T) are coloured in red.

FIGS. 7A-7D. Bs3 and Bs3-E Promoter Sequences Protected by AvrBs3 and AvrBs3Δrep16, Respectively.

A representative DNaseI footprint experiment is shown. AvrBs3 DNaseI footprint on the Bs3 promoter sequence (FIG. 7A, upper/sense DNA strand, SEQ ID NO:42; FIG.

7B, lower/antisense DNA strand, SEQ ID NO:43). AvrBs3Δrep16 DNaseI footprint on the Bs3-E promoter sequence (FIG. 7C, upper, sense DNA strand, SEQ ID NO:44); FIG. 7D, lower antisense DNA strand, SEQ ID NO:45).

For FIGS. 7A-7D (top), the fluorescently labelled PCR product was incubated with a 5× molar excess (calculated for protein dimers) of His6::AvrBs3, His6::AvrBs3Δrep16, and BSA, respectively, treated with DNaseI and analyzed on a capillary sequencer. The y axis of the electropherogram shows the relative fluorescence intensity corresponding to the 5'-6-FAM-labelled sense strand (a, c) or the 5'-HEX-labelled antisense strand (b, d) of the PCR product on an arbitrary scale. The traces for the reactions with His6::AvrBs3 (green) or His6::AvrBs3Δrep16 (red), respectively, and BSA (black, negative control) were superimposed. A reduction of peak height in the presence of AvrBs3 or AvrBs3Δrep16, respectively, in comparison to the negative control corresponds to protection. The protected region is indicated by green (AvrBs3) or red (AvrBs3Δrep16) vertical lines. (middle) Electropherogram of the DNA sequence. Orange coloured peaks with numbers correspond to the DNA nucleotide size standard. The predicted target boxes of the effectors in the DNA sequence are underlined. Nucleotides covered are marked by a green (AvrBs3) or red (AvrBs3Δrep16) box. Numbers below refer to nucleotide positions relative to the transcription start (+1) in the presence of AvrBs3 (a, b) or AvrBs3Δrep16 (c, d), respectively. (bottom) DNA PCR product used for DNaseI footprinting, amplified from the Bs3 (a, b) or Bs3-E (c, d) promoters, respectively. The protected regions on the single DNA strands are indicated by gray boxes. Numbers below refer to nucleotide positions relative to the transcription start (+1) in the presence of AvrBs3 (a, b) or AvrBs3Δrep16 (c, d), respectively. The experiments were repeated three times with similar results.

Figure 8A:
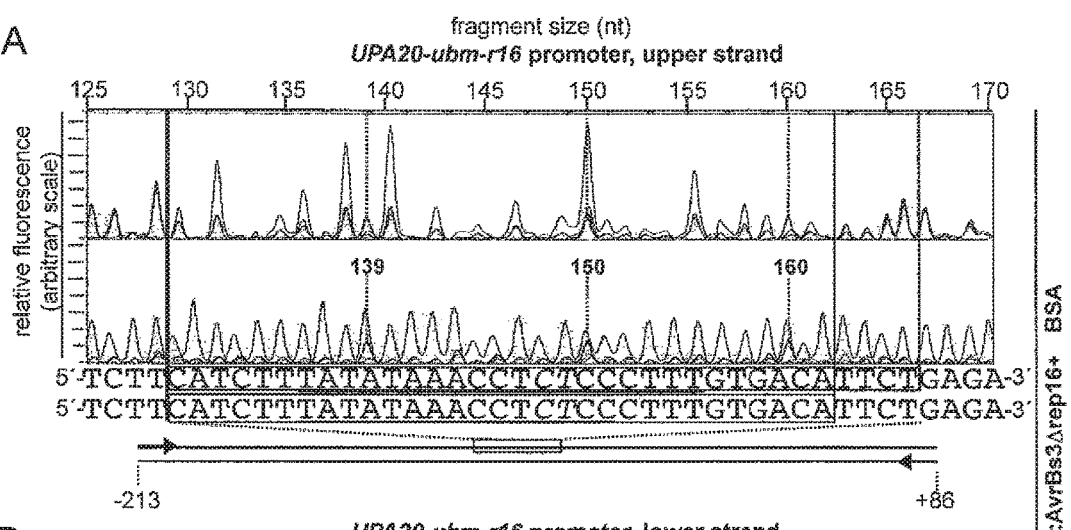
Figure 8B:
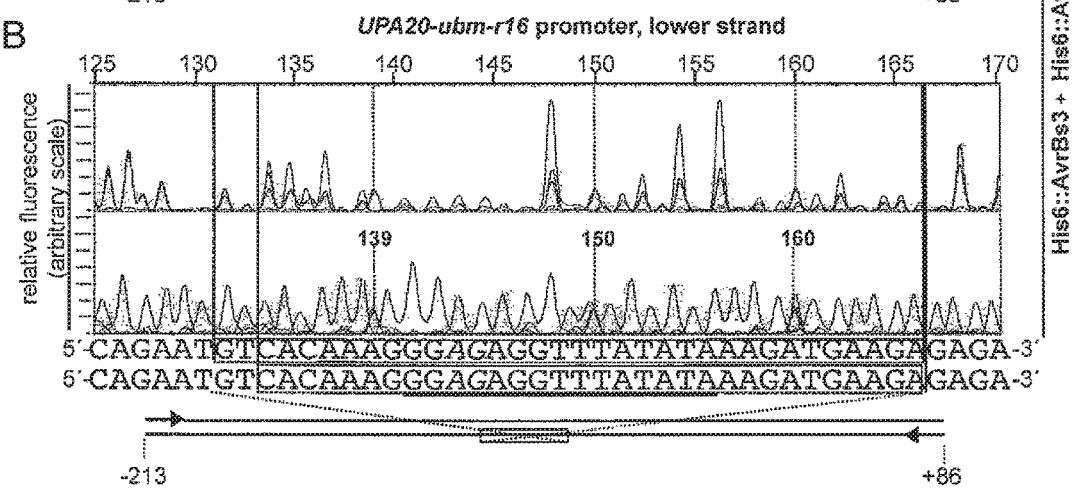

FIGS. 8A-8B. UPA20-ubm-r16 Promoter Sequence Protected by AvrBs3 and AvrBs3Δrep16.

A representative DNaseI footprint experiment. AvrBs3 and AvrBs3Δrep16 DNaseI footprint on the UPA20-ubm-r16 promoter sequence FIG. 8A, upper, sense DNA strand (SEQ ID NO:46); FIG. 8B lower, antisense DNA strand (SEQ ID NO:47)). (top Fluorescently labelled PCR product was incubated with a 5× molar excess of His6::AvrBs3, His6::AvrBs3Δrep16 and BSA (calculated for protein dimers), respectively, treated with DNaseI and analyzed on a capillary sequencer. The y axis of the electropherogram shows the relative fluorescence intensity corresponding to the 5'-6-FAM-labelled sense strand (a) or the 5'-HEX-labelled antisense strand (b) of the PCR product on an arbitrary scale. The traces for the reactions with His6::AvrBs3 (green), His6::AvrBs3Δrep16 (red) and the negative control BSA (black) were superimposed. A reduction of peak height in the presence of AvrBs3 and AvrBs3Δrep16 in comparison to the negative control corresponds to protection. The protected regions are indicated by green (AvrBs3) and red (AvrBs3Δrep16) vertical lines. (middle) Electropherogram of the DNA sequence. Orange coloured peaks with numbers correspond to the DNA nucleotide size standard. Nucleotides covered by AvrBs3 are marked by green lines and a green box (with the UPA box underlined), nucleotides covered by AvrBs3Δrep16 are marked by red lines and a red box (with the AvrBs3Δrep16-box underlined). The UPA20-ubm-r16 mutation (GA to CT) is indicated in italics. (bottom) DNA PCR product used for DNaseI footprinting, amplified from the UPA20-ubm-r16 promoter. The protected regions on the single DNA strands are indicated by gray boxes. Numbers below refer to nucleotide positions relative to the transcription start (+1) of the UPA20 wildtype promoter in the presence of AvrBs3. The experiment was repeated three times with similar results.

Figure 9:
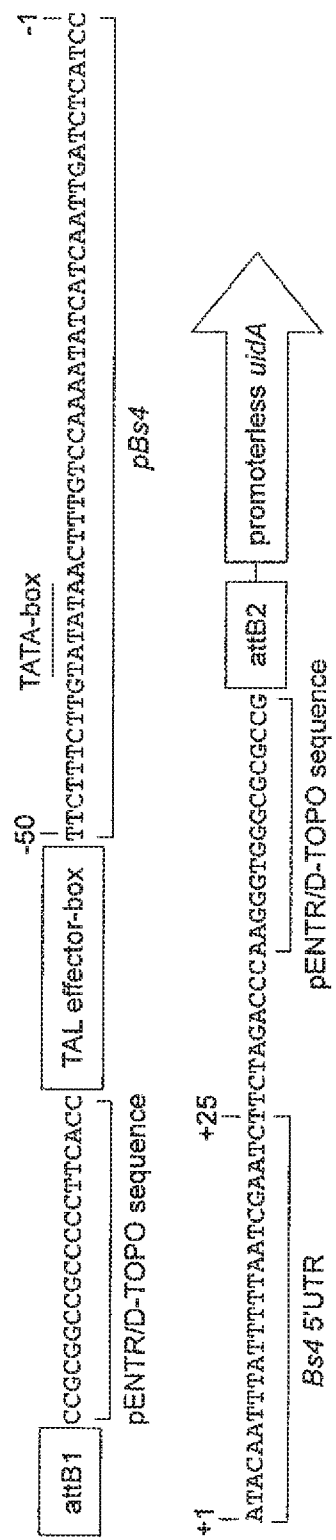

FIG. 9. GUS Reporter Constructs.

Target DNA sequences (TAL effector-box) were inserted 5' of the minimal tomato Bs4 promoter (41) (pBs4; −50 to +25) sequence and transferred by GATEWAY recombination into the A. tumefaciens T-DNA vector pGWB330 constructing a fusion to a promoterles uidA (β-glucuronidase, GUS) gene. attB1, attB2; GATEWAY recombination sites. The pENTR/D-TOPO sequence positioned between the attB1 site and the TAL effector-box is represented by SEQ ID NO:48, the pBs4 and Bs4 5'UTR sequences (ranging from −50 to +25) are collectively represented by SEQ ID NO:49, and the remaining nucleotide sequence shown through the attB2 site is represented by SEQ ID NO:50.

FIGS. 10A-10C. Recognition Specificity of the Putative Repeat 0 in Hax3.

FIG. 10A. Amino acids 12 and 13 of Hax3-repeat units and four possible target Hax3-boxes (shown from top to bottom in order as SEQ ID NOs:4 and 51-53) with permutations in the position corresponding to repeat 0.

FIG. 10B. The target boxes were cloned in front of the minimal tomato Bs4 promoter into a GUS reporter vector.

FIG. 10C. GUS activities with 35S-driven hax3 or empty T-DNA (−) codelivered via A. tumefaciens with the GUS reporter constructs into N. benthamiana leaf cells (4-MU, 4-methyl-umbelliferone; n=3; error bars indicate SD). For qualitative assays, leaf discs were stained with X-Gluc. The experiment was performed twice with similar results.

Figure 11A:
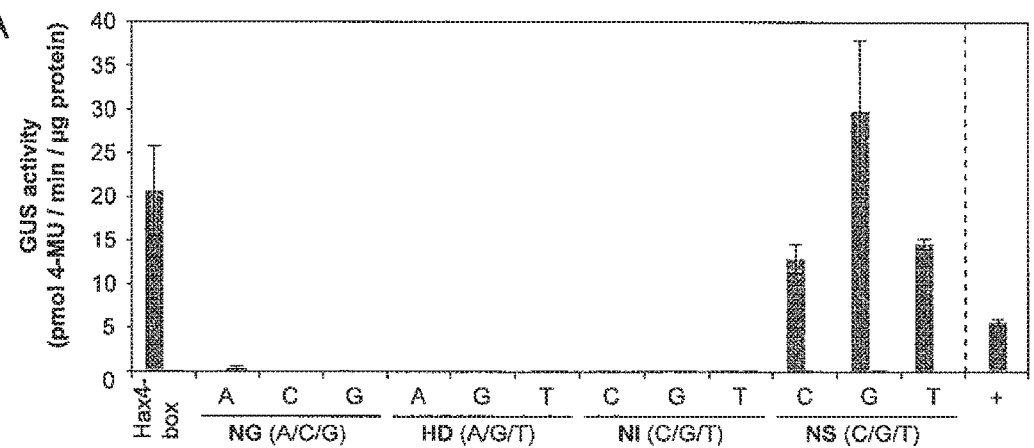
Figure 11B:
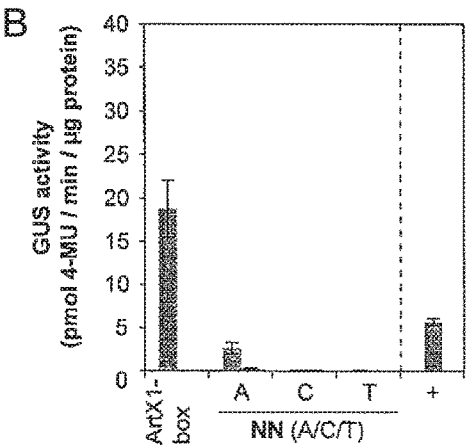
Figure 11C:
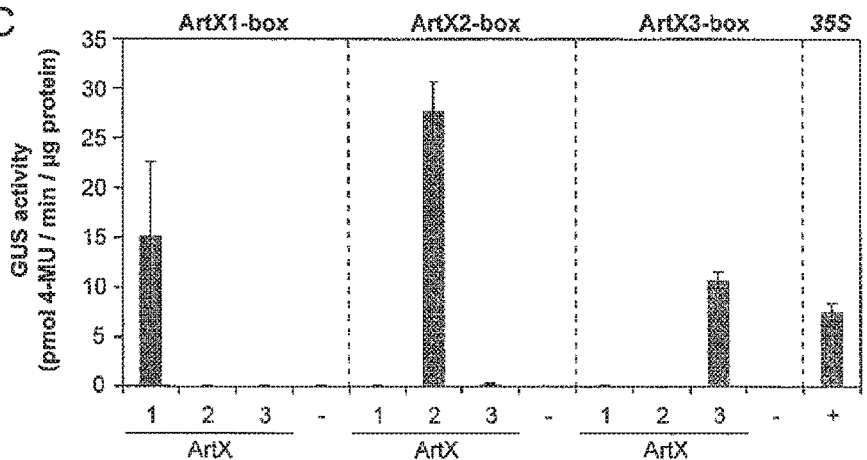

FIGS. 11A-11C. DNA Base Pair Recognition Specificities of Repeat Types

Hax4- and ArtX-box-derivatives were cloned in front of the minimal Bs4 promoter into a GUS reporter vector. Quantitative data to FIG. 3.

FIG. 11A. Specificity of NG-, HD-, NI-, and NS-repeat units. Hax4-inducibility of Hax4-box derivatives permutated in repeat type target bases.

FIG. 11B. Specificity of NN-repeat units. ArtX1-inducibility of ArtX1-box derivatives permutated in NN-repeat target bases.

FIG. 11C. Specific inducibility of ArtX-boxes by artificial effectors ArtX1, ArtX2, and ArtX3, respectively.

For FIG. 11A-11C, the GUS reporter constructs were codelivered via A. tumefaciens into N. benthamiana leaf cells together with 35S-driven hax4, artX1, artX2, artX3 genes (gray bars), and empty T-DNA (a, b, white bars; c, −), respectively (n=3; error bars indicate SD). 35S::uidA (+) served as control. The experiments were performed three times with similar results.

FIGS. 12A-12C. Predicted Target DNA Sequences for AvrXa10.

FIG. 12A. Amino acids 12 and 13 of the AvrXa10-repeat units and two possible target boxes with predicted NN type repeat-specificity A (SEQ ID NO:54) or G (SEQ ID NO:55).

FIG. 12B. AvrXa10 target boxes were cloned in front of the minimal Bs4 promoter into a GUS reporter vector.

FIG. 12C. GUS assay of 35S-driven avrXa1O, hax3 (specificity control), or empty T-DNA (−) codelivered via A. tumefaciens with GUS reporter constructs into N. benthamiana leaf cells. 35S::uidA (+) served as constitutive control (n=3; error bars indicate SD). For qualitative assays, leaf discs were stained with X-Gluc. The experiment was performed three times with similar results.

FIGS. 13A-13C. Recognition Specificity of the Repeat Type IG in Hax2.

FIG. 13A. Amino acids 12 and 13 of Hax2 repeat units and four possible target Hax2-boxes (shown from top to bottom in order as SEQ ID NOs:3 and 56-58) for repeat type IG.

FIG. 13B. The Hax2 target boxes were cloned in front of the minimal Bs4 promoter into a GUS reporter vector.

FIG. 13C. GUS assay of 35S promoter-driven hax2 or empty T-DNA (−) codelivered via *A. tumefaciens* with the GUS reporter constructs into *N. benthamiana* leaf cells. 35S::uidA (+) served as constitutive control (n=3; error bars indicate SD. For qualitative assays, leaf discs were stained with X-Gluc. The experiment was performed three times with similar results.

FIGS. 14A-14E. Hax2 induces expression of PAP1 in *A. thaliana*.

FIG. 14A. Leaves of *A. thaliana* were inoculated with *A. tumefaciens* strains delivering T-DNA constructs for 35S-driven expression of hax2, hax3, and hax4, respectively. Expression of hax2, but not of hax3 and hax4 induced purple pigmentation suggestive of anthocyanin production. The photograph was taken 7 days post inoculation.

FIG. 14B. Transgenic *A. thaliana* line carrying hax2 under control of an ethanol-inducible promoter. Plants of a segregating T2 population were sprayed with 10% ethanol to induce expression of the transgene. Only hax2-transgenic plants accumulated anthocyanin. The photograph was taken 6 days post treatment.

FIG. 14C. Semiquantitative RT-PCR of hax2 (29 cycles), PAP1 (32 cycles), and elongation factor Tu (EF-Tu, 32 cycles) with cDNA from hax2- transgenic plants of three independent *A. thaliana* lines before (−) and 24 h after (+) spraying with 10% ethanol.

FIG. 14D. Amino acids 12 and 13 of Hax2 repeat units and target DNA sequence of Hax2 (SEQ ID NO:62).

FIG. 14E. The promoter of PAP1 from *A. thaliana* Col-0 contains an imperfect Hax2-box.

Mismatches to the predicted Hax2-box are coloured in red. A putative TATA-box, the natural transcription start site (+1), and the first codon of the PAP1 coding sequence are indicated (SEQ ID NO:59).

FIGS. 15A-15B. Table I. Predicted DNA Target Sequences of TAL Effectors

The table shows repeat sequences of TAL effectors and the predicted DNA target sequences used from amino acids 12 and 13 of the repeat units. The predicted DNA sequences shown in the table from top to bottom are represented in order by SEQ ID NOs:60-109. A star (*) indicates a deletion of amino acid 13. Target DNA specificity deduced from amino acids 12 and 13 of the repeat units. A thymidine nucleotide is added at the 5' end due to the specificity of the putative repeat 0. The sequence of the upper (sense) strand of the double stranded DNA is given in ambiguous code (R=A/G; N=A/C/G/T; •=unknown specificity). Xcv, *Xanthomonas campestris* pv. *vesicatoria*; Xg, *Xanthomonas gardneri*; Xca, *Xanthomonas campestris* pv. *armoraciae*; Xoo, *Xanthomonas oryzae* pv. *oryzae*; Xac, *Xanthomonas axonopodis* pv. *citri*; Xau, *Xanthomonas citri* pv. *aurantifolii*; Xcm, *Xanthomonas campestris* pv. *malvacearum*; Xam, *Xanthomonas axonopodis* pv. *manihotis*; Xoc, *Xanthomonas oryzae* pv. *Oryzicola*.

FIGS. 16A-16F. Protein Sequences of AvrBs3, Hax2, Hax3, Hax4

For each of the protein sequences shown in FIG. 16A-FIG. 16F, the N-terminus, C-terminus as well as the single repeat sequences are shown. AvrBs3 is represented by SEQ ID NO:110, Hax2 is represented by SEQ ID NO:111, Hax3 is represented by SEQ ID NO:112, and Hax 4 is represented by SEQ ID NO:113.

FIGS. 17A-17D. The Effector ARTBs4 Induces Expression of the Minimal Bs4 Promoter FIG. 17A. Amino acids 12 and 13 of the Hax4 repeat units and predicted target DNA specificity (Hax4 box) (SEQ ID NO:5). The Hax4(mut) box (SEQ ID NO:6) contains four base pair exchanges in comparison to the Hax4 box.

FIG. 17B. Amino acids 12 and 13 of the artificial effector ARTBs4 repeat units and predicted target DNA specificity (ARTBs4 box) (SEQ ID NO:114).

FIG. 17C. The Hax4 box was cloned in front of the minimal Bs4 promoter into a GUS reporter vector. The ARTBs4 box is naturally present in the minimal Bs4 promoter.

FIG. 17D. Specific inducibility of the Hax4 and ARTBs4 boxes by Hax4 and ARTBs4, respectively. GUS reporter constructs were codelivered via *Agrobacterium tumefaciens* into *N. benthamiana* with 35S-driven hax4 (grey bars), ARTBs4 (white bars) and empty T-DNA (ev, black bars), respectively (error bars indicate SD). 4-MU, 4-methylumbelliferone. 35S::uidA (GUS, grey bar) served as control. Leaf disks were stained with X-Gluc (5-bromo-4-chloro-3-indolyl-β-D-glucuronide).

Figure 18A:
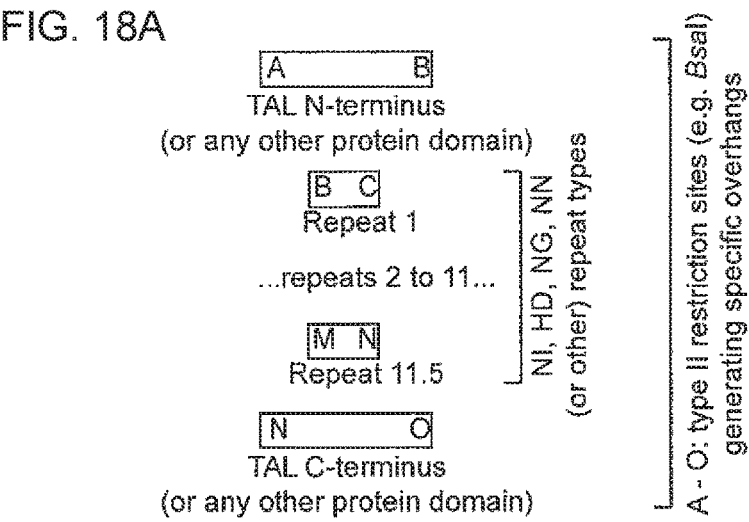
Figure 18B:
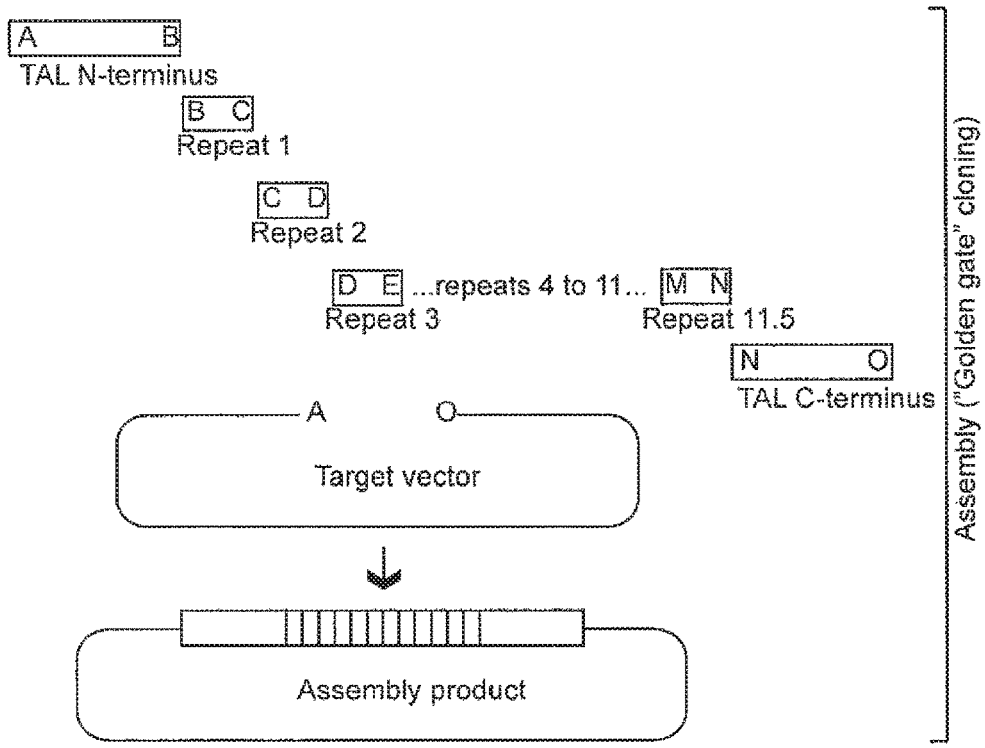
Figure 19A:
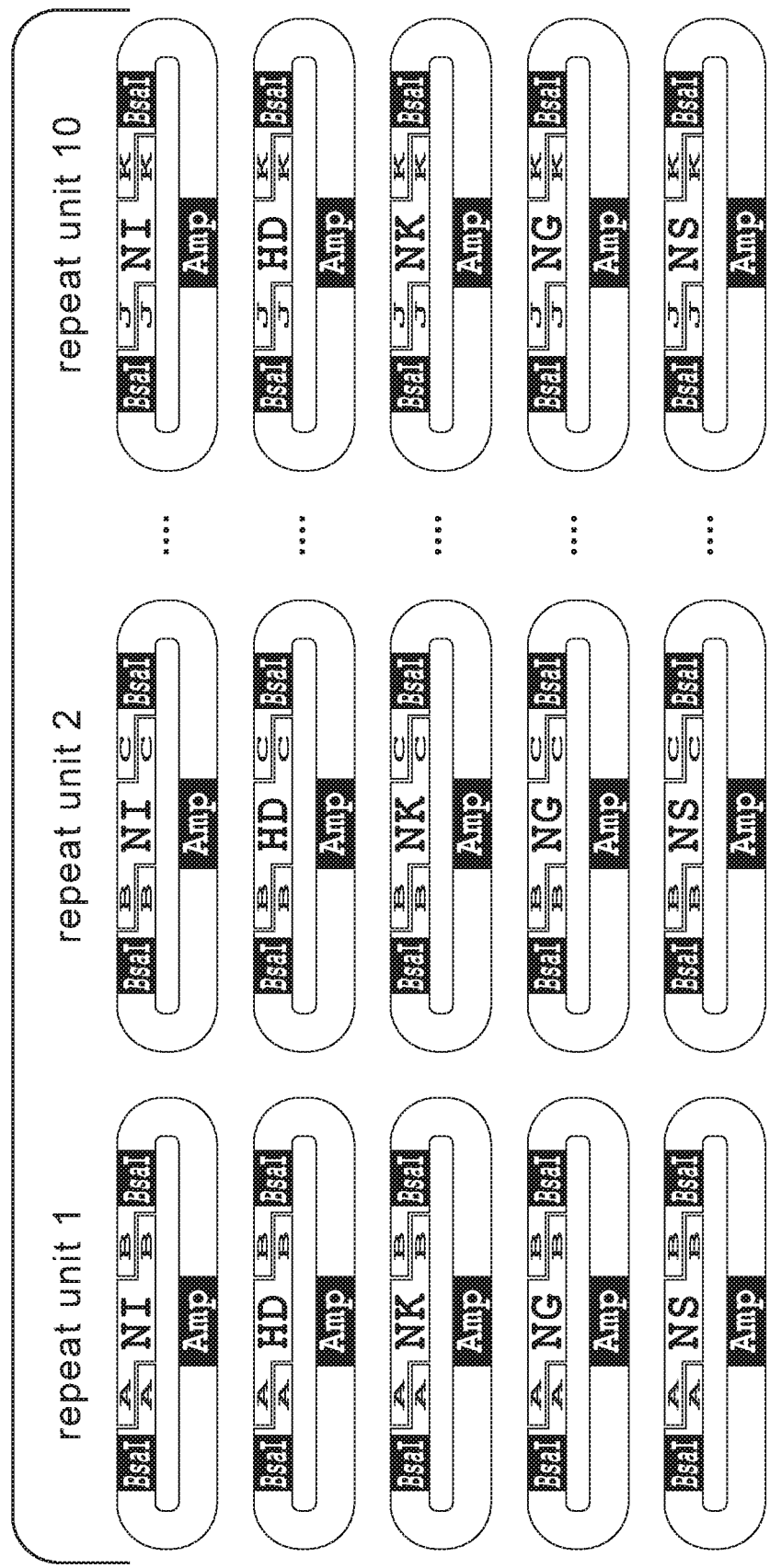
Figure 19B:
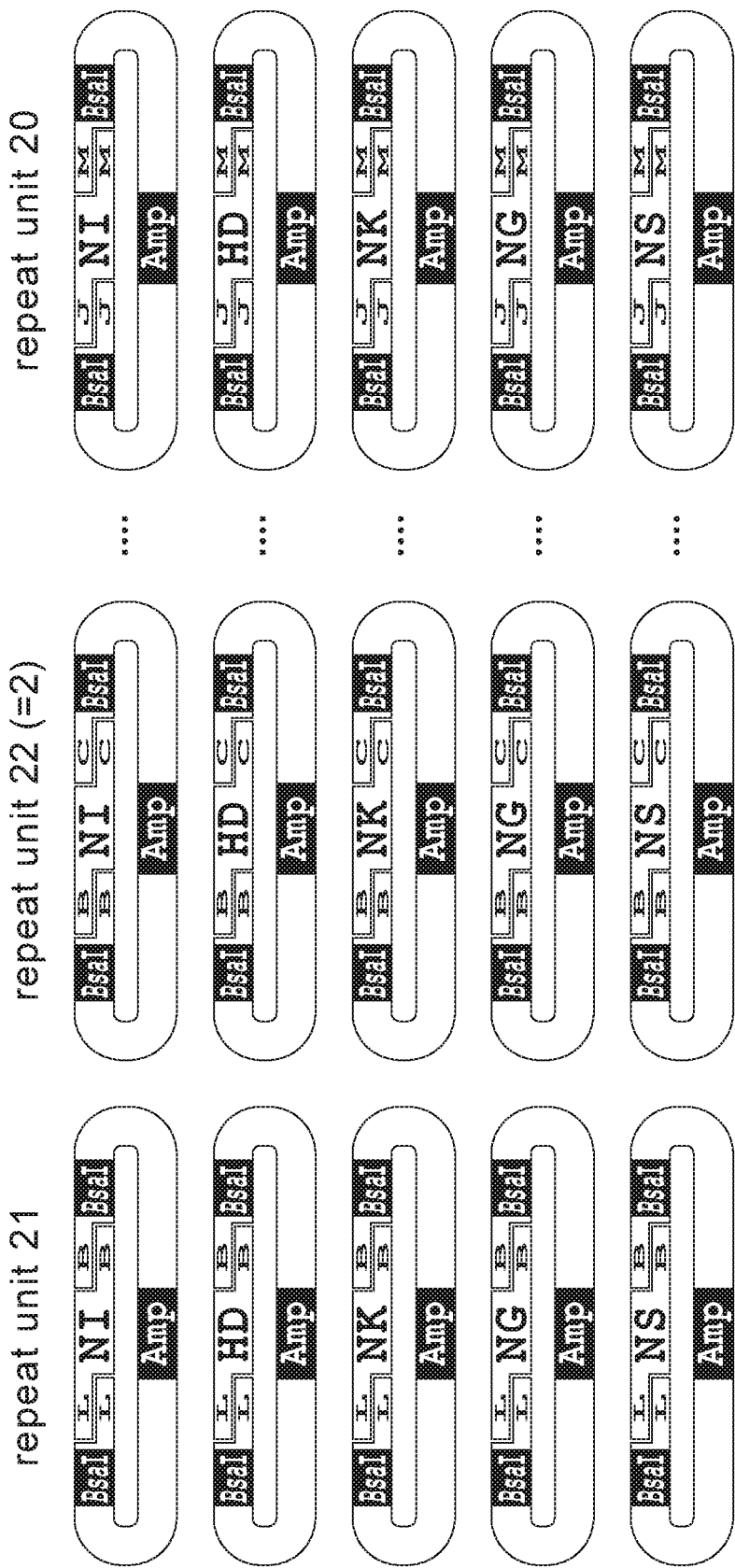
Figure 19C:
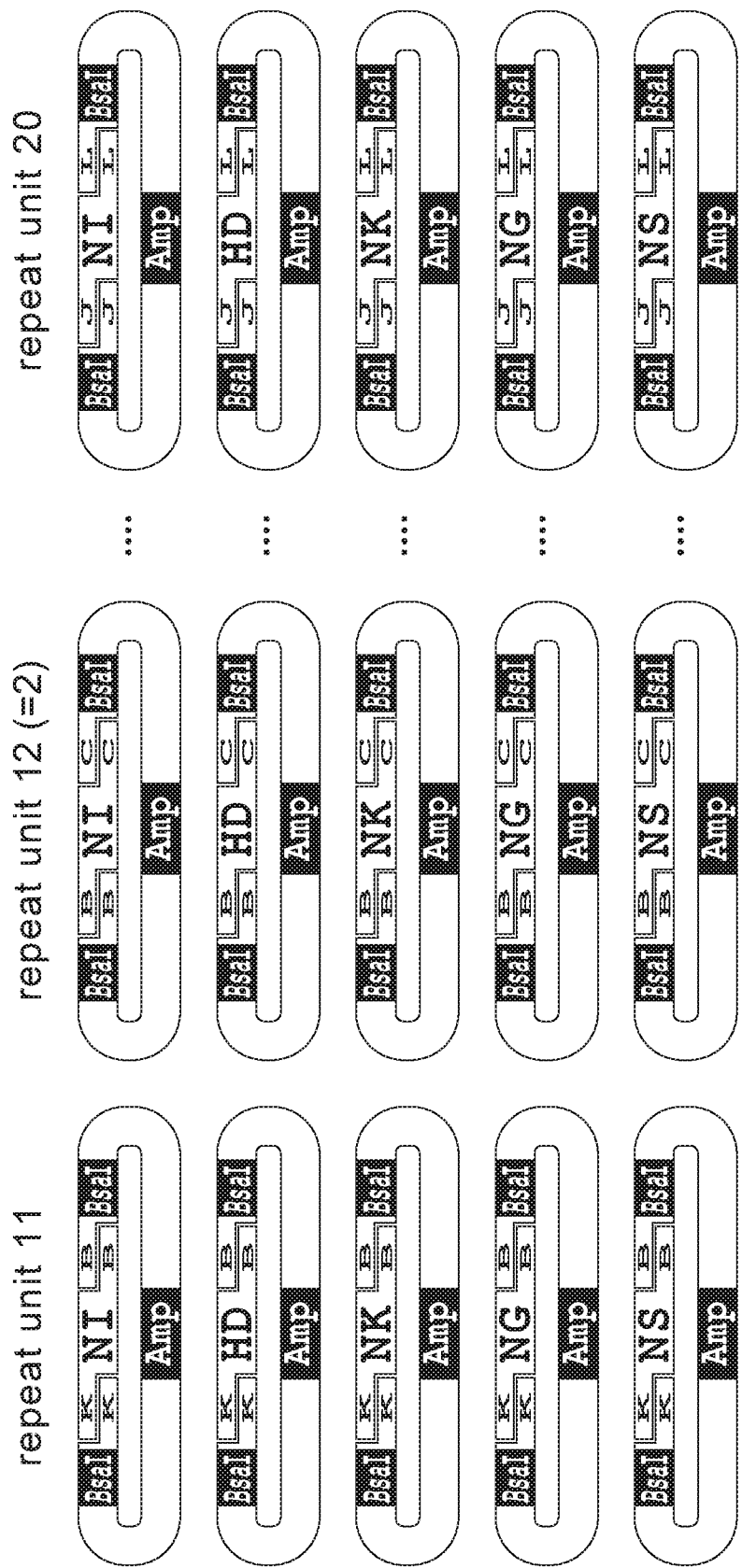
Figure 19D:
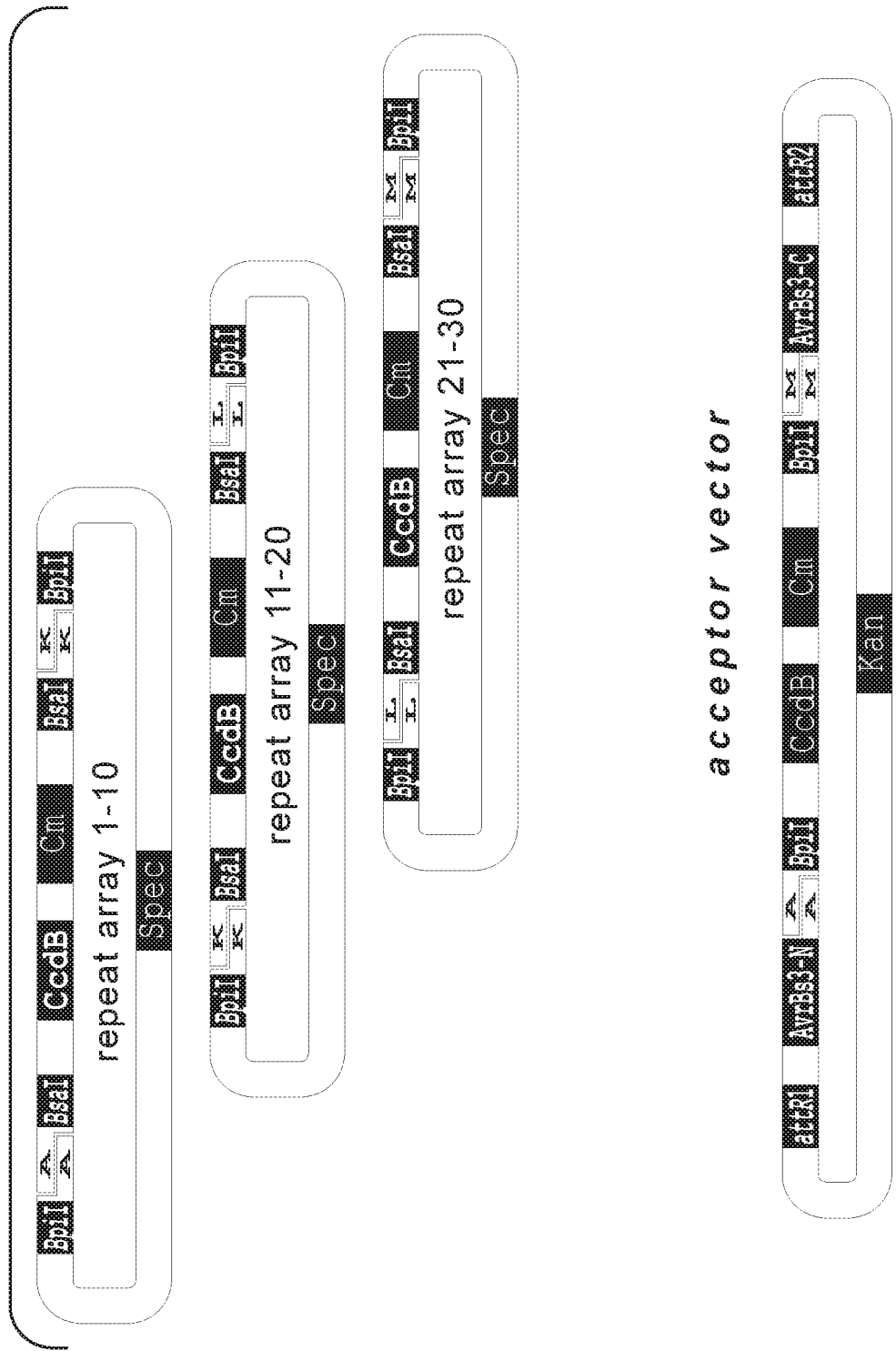
Figure 19E:
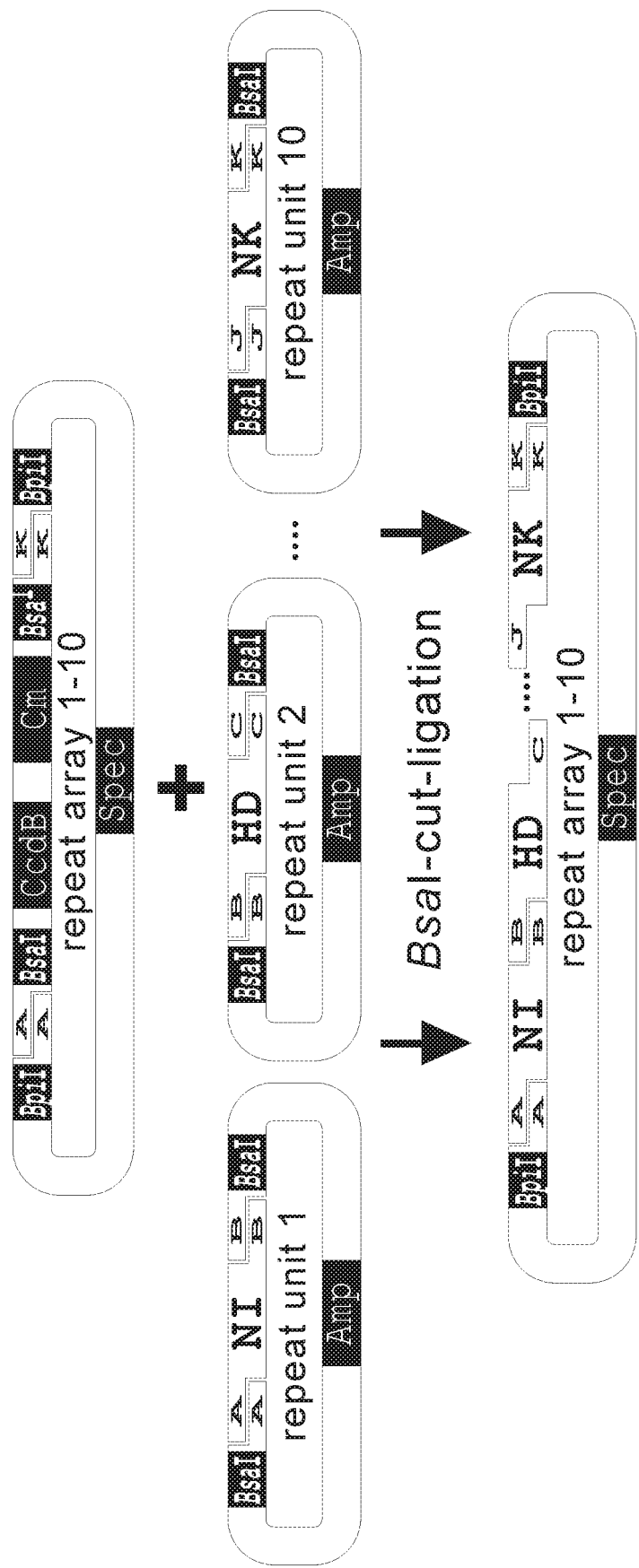
Figure 19F:
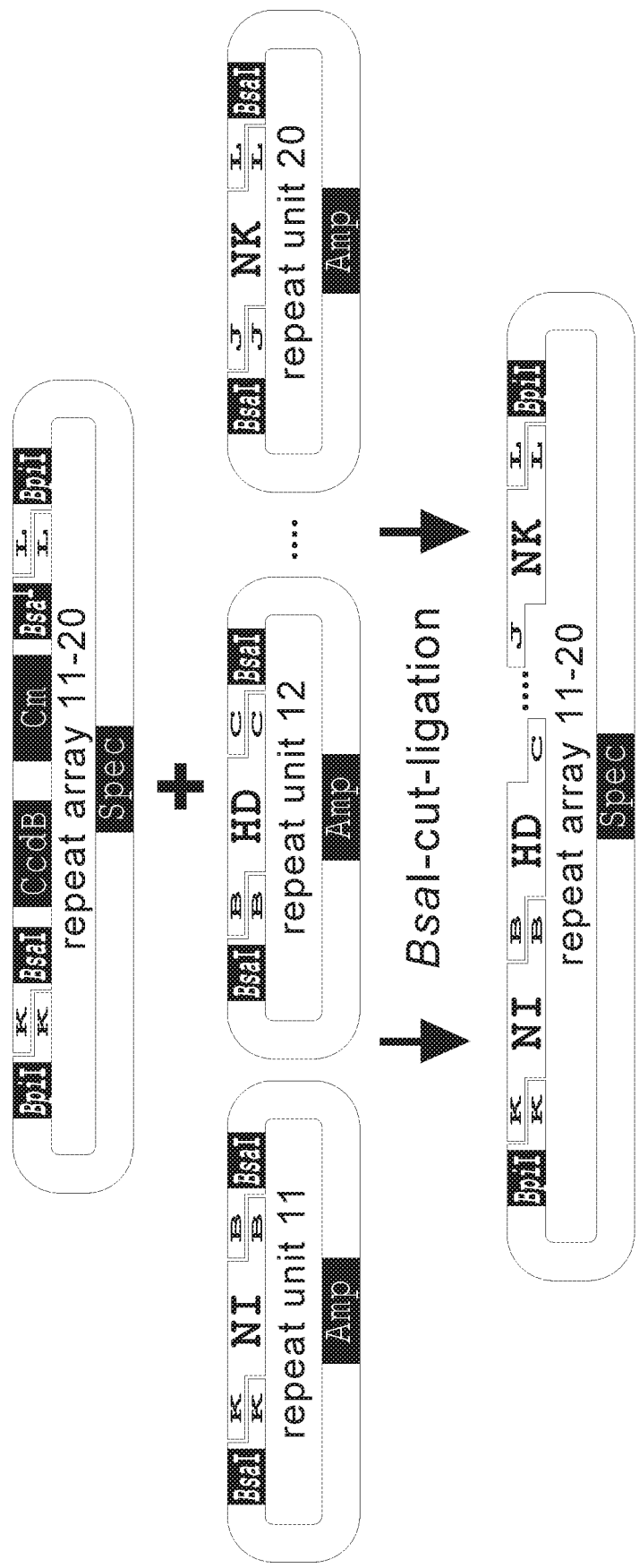
Figure 19G:
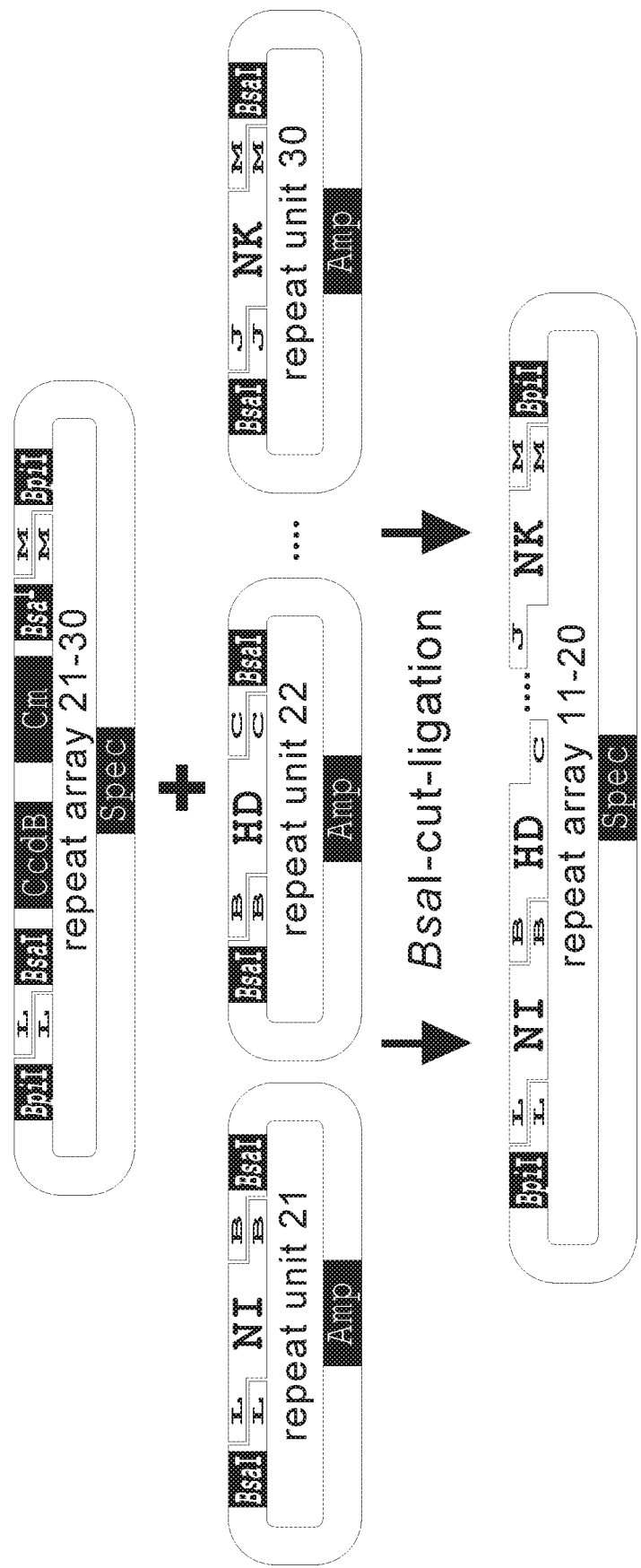
Figure 19H:
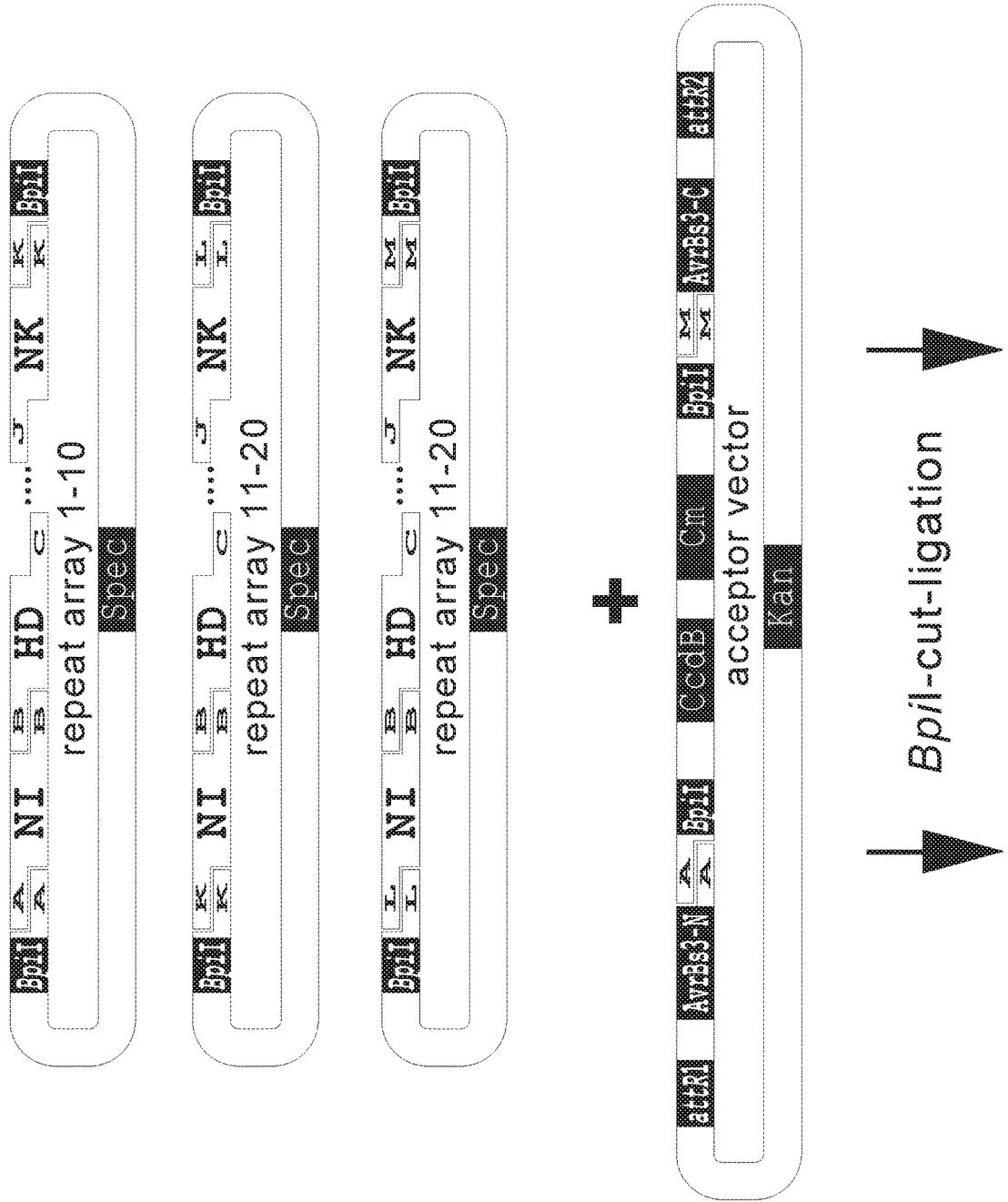
Figure 19I:
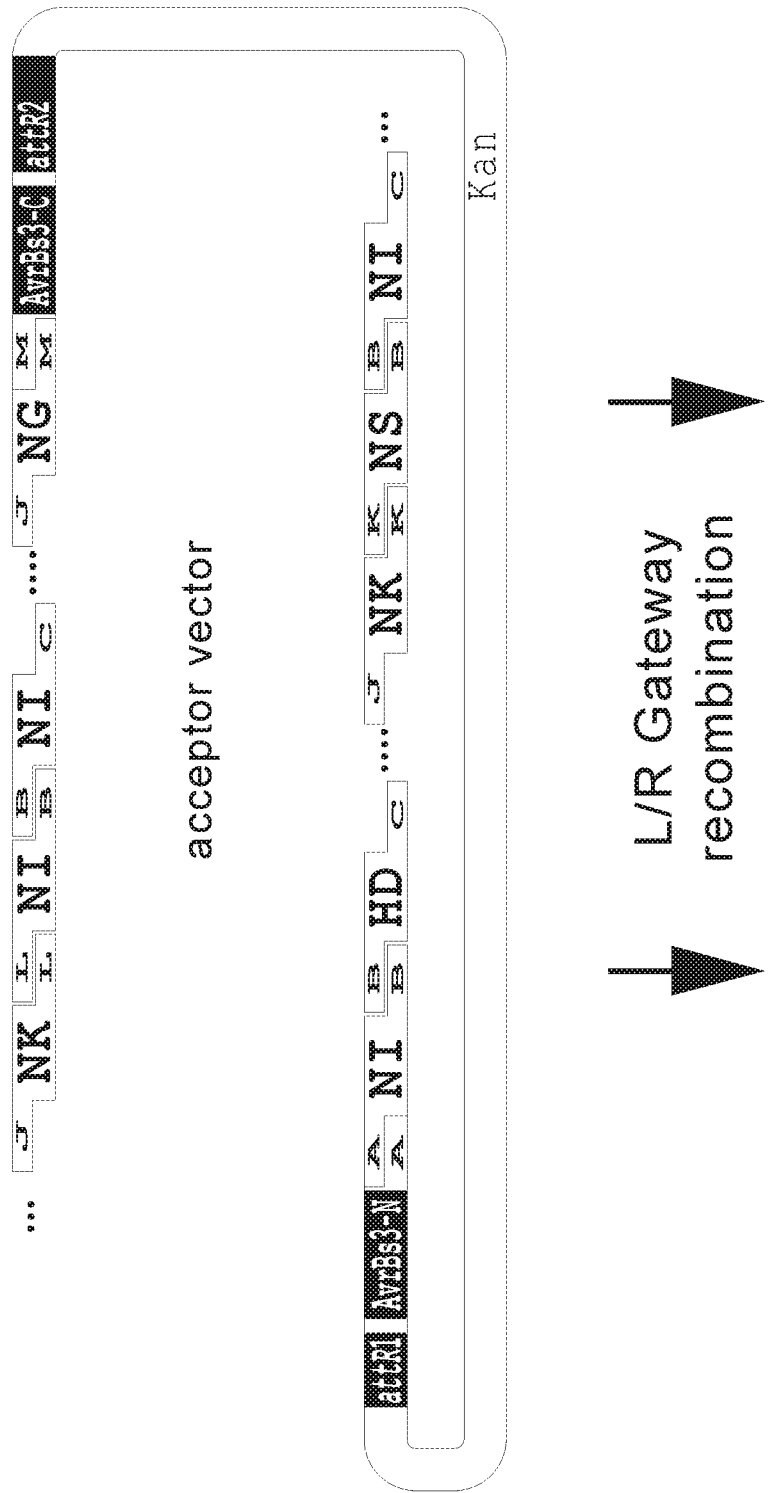

FIGS. 18A-18B. Diagram for "Golden gate" Cloning of Repeat Domanins and Effectors FIG. 18A. Building blocks consisting of individual repeat units (or other protein domains) are subcloned with flanking type II restriction enzyme target sites (e.g. BsaI) that generate specific overhangs. Matching overhangs are indicated with identical letters (A to O). Different repeat types are cloned as building blocks for each position (e.g. repeat 1, repeat 2, etc.). The repeat specificities are: NI=A, HD=C, NG=T, NN=G or A.

FIG. 18B. The building blocks are assembled into a target vector by ligation of matching overhangs using "Golden gate" cloning (restriction-ligation). In general, the resulting assembly product does not contain any of the target sites used for cloning.

FIGS. 19A-19I. Alternative Method for Generation of Designer Effectors via Golden Gate Cloning FIGS. 19A-19I depict various vectors described in the methods disclosed in Example 3 below as well as provide a schematic of the method.

FIG. 20. Experiments to Analyze Novel Repeat Specificities

Artificial TALs were assembled with the first six repeats of the TAL Hax3. Repeat 7 to 11.5 were assembled using one repeat type with unknown specificity. Four possible target DNA boxes were used containing six A (SEQ ID NO:115), C (SEQ ID NO:116), G (SEQ ID NO:117), or T (SEQ ID NO:118), respectively. Similarly, artificial TALs and reporter were constructed with 2, 3, or 4 repeats to test. The target DNA boxes were inserted into the Bs4 minimal promoter upstream of a promoterless uidA reporter gene.

Figure 21:
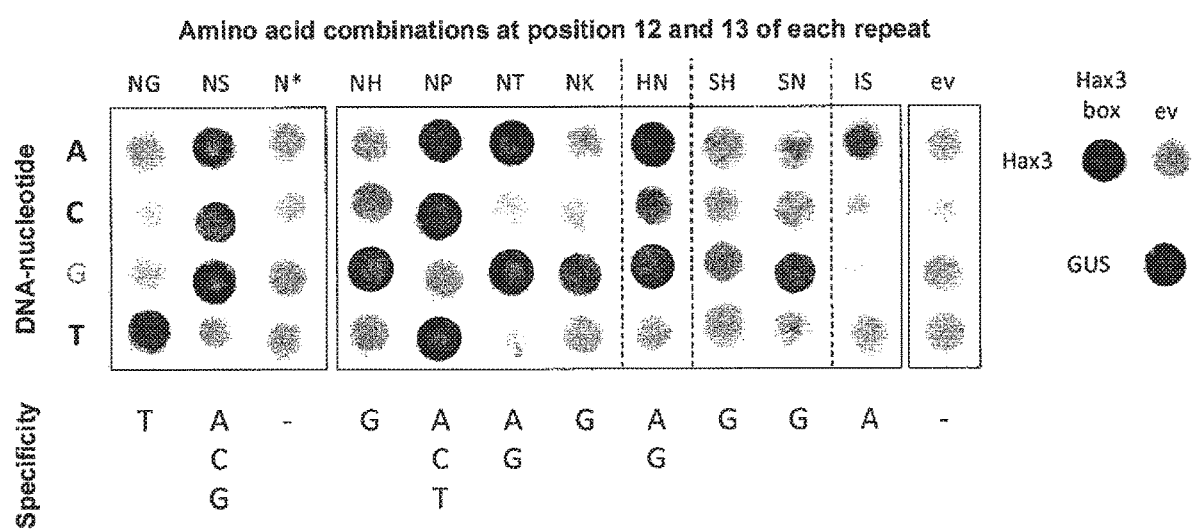

FIG. 21. TAL Repeat Specificities

*Agrobacterium*-mediated expression of artificial TALs and corresponding reporter constructs in *Nicotiana benthamiana*. Leaf disks were sampled two days post transformation, stained for GUS reporter activity and destained with ethanol. A blue colour indicates expression of the reporter construct and therefore, an activity of the TAL. Empty vector (ev) and constitutively expressed GUS were used as negative control, respectively. Novel repeat specificities are colored in red. Repeat types with strong DNA recognition properties are: NH, NP, NT, and HN. Repeat types with weak DNA recognition properties are: NG, N*, NK, SH, SN, IS.

Figure 22:
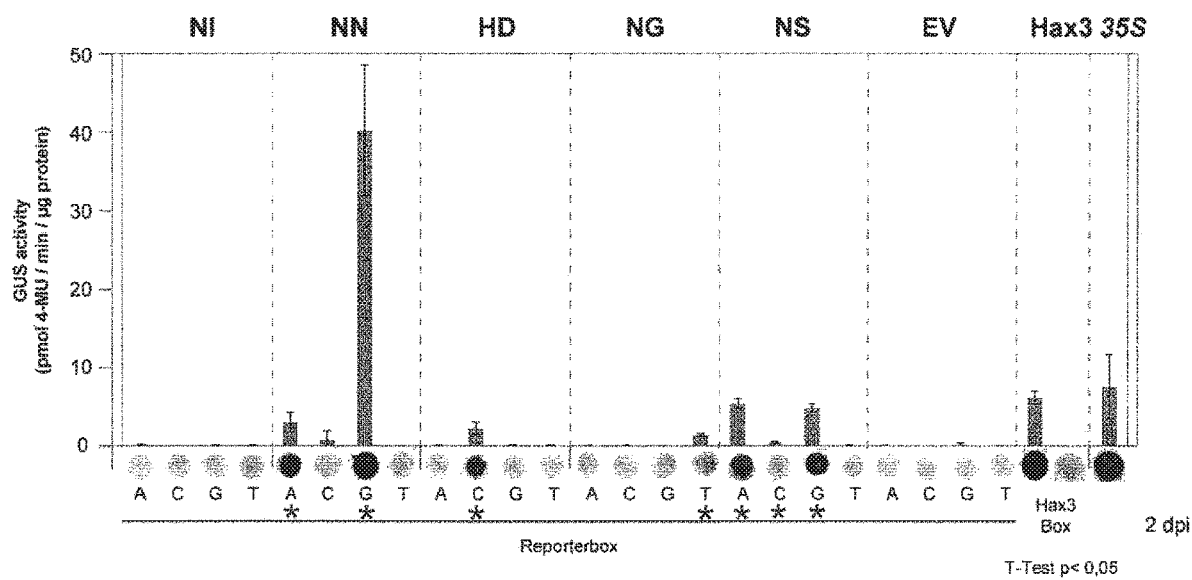

FIG. 22. Quantitative Analysis of known Repeat Specificities.

Artificial TALs were assembled with the first six repeats of the TAL Hax3. Repeat 7 to 11.5 were assembled using one repeat type. Four possible target DNA boxes were used containing six A, C, G, or T, respectively upstream of the Bs4 minimal promoter and a promoterless uidA reporter gene. The data show that repeat type NN has much stronger DNA-recognition properties than the other repeat types. Repeat type NI is very weak and does not show a preference in this setup. Repeat type NS was shown to recognize all four DNA bases, before, but does show a preference for A and G, here. EV: empty vector control.

Figure 23:
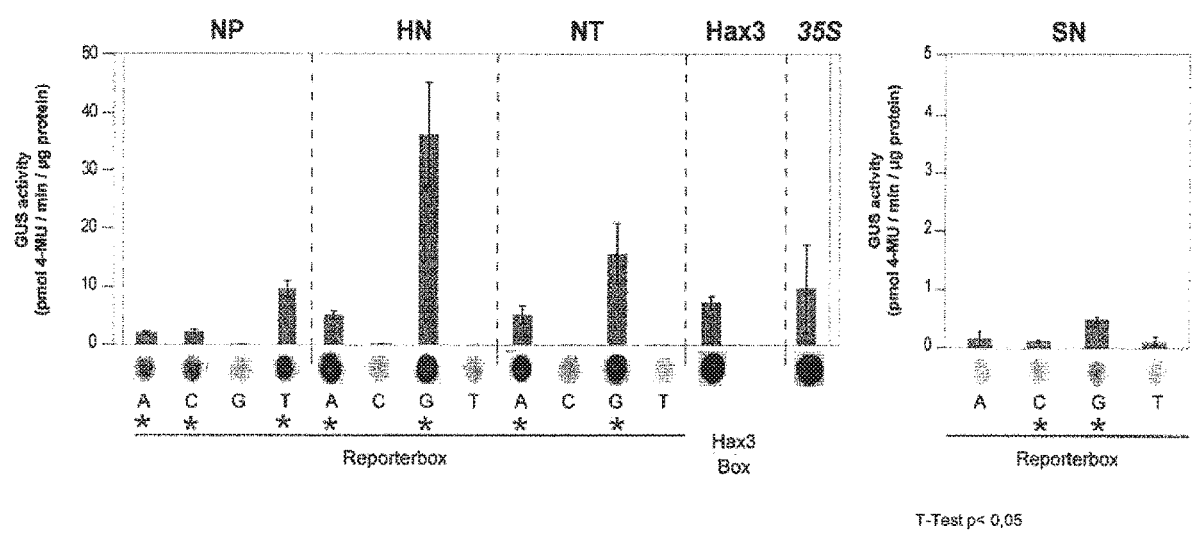

FIG. 23. Quantitative Analysis of Novel Repeats with Multiple Specificities

Quantitative analysis of novel repeats with multiple specificities. Artificial TALs were assembled with the first six repeats of the TAL Hax3. Repeat 7 to 11.5 were assembled using one repeat type. Four possible target DNA boxes were used containing six A, C, G, or T, respectively upstream of the Bs4 minimal promoter and a promoterless uidA reporter gene (see, FIG. 20).

Figure 24:
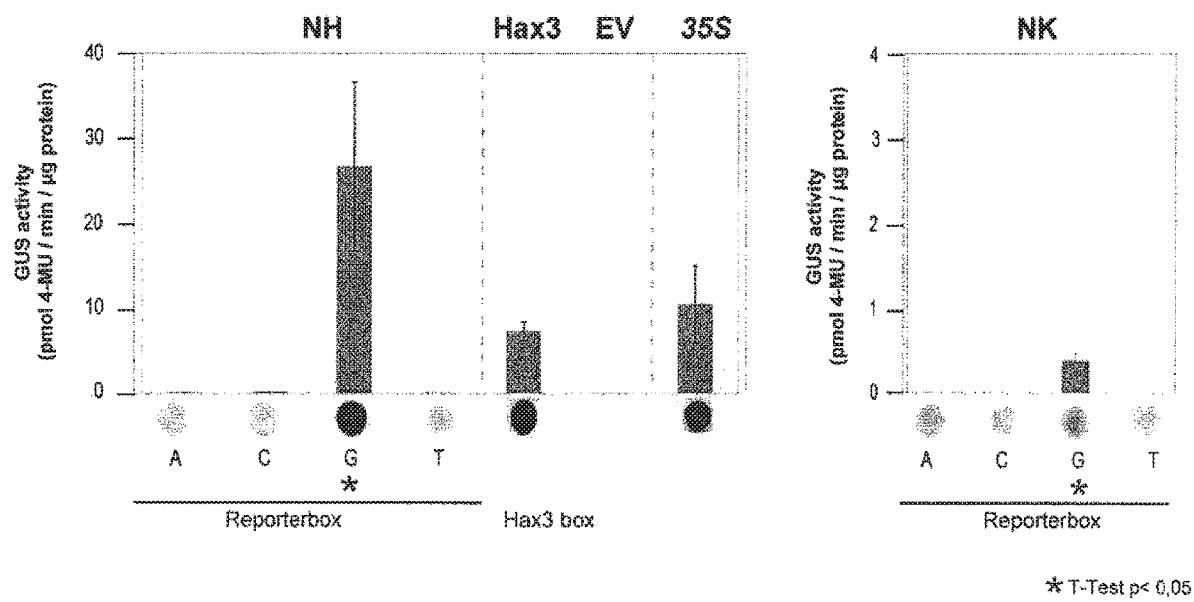

FIG. 24. Quantitative Analysis of Novel Repeats with only one Specificity

Artificial TALs were assembled with the first six repeats of the TAL Hax3. Repeat 7 to 11.5 were assembled using one repeat type. Four possible target DNA boxes were used containing six A, C, G, or T, respectively upstream of the Bs4 minimal promoter and a promoterless uidA reporter gene. The data show that repeat type NH is much stronger than repeat type NK, but also recognizes only one specific base (G).

Figure 25:
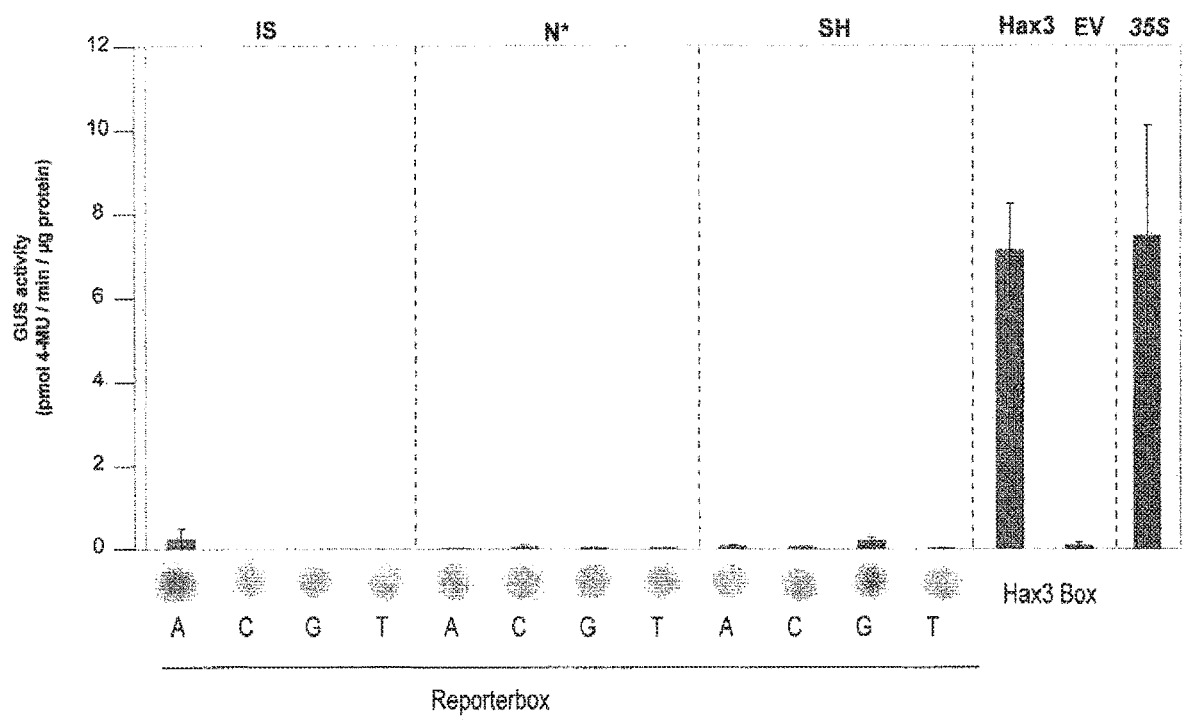

FIG. 25. Quantitative Analysis of Novel Repeats with Novel Specificities

Artificial TALs were assembled with the first six repeats of the TAL Hax3. Repeat 7 to 11.5 were assembled using one repeat type. Four possible target DNA boxes were used containing six A, C, G, or T, respectively upstream of the Bs4 minimal promoter and a promoterless uidA reporter gene. These repeat types show only very low activity in the reporter assay, likely due to their weak DNA interaction potential.

Figure 26:
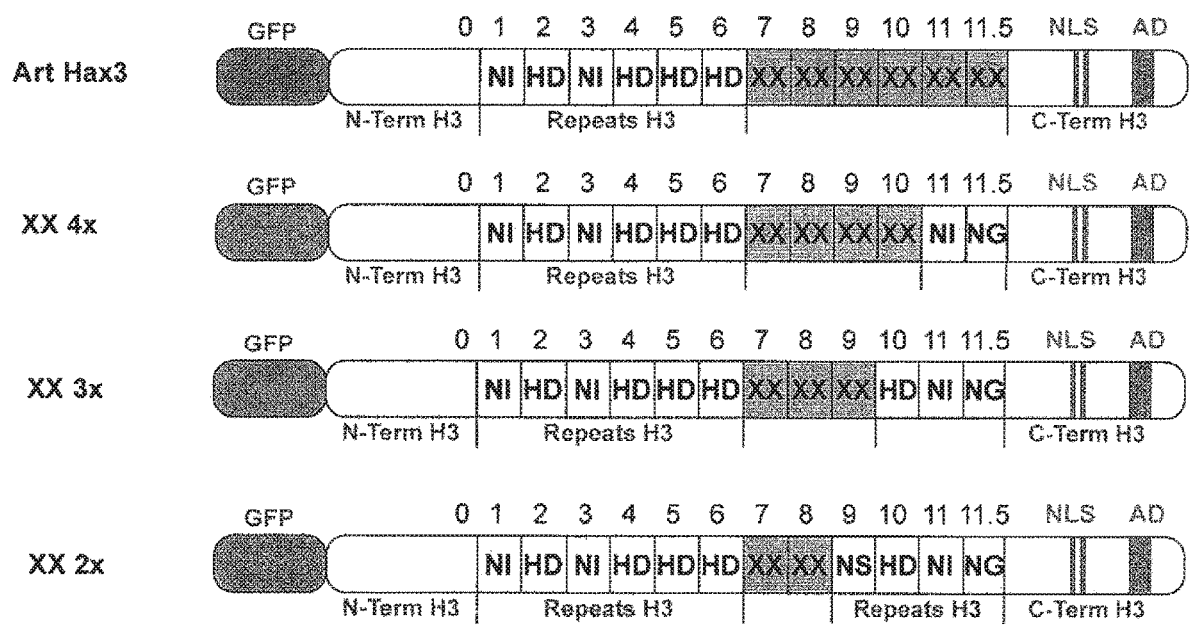

FIG. 26. Experimental Setup to Study Specificity of Repeat Types with Low DNA Recognition Potential The artificial effectors were assembled to contain 6, 4, 3, or 2 repeats, respectively, with unknown specificity (designated XX) in addition to Hax3 repeats. Target boxes in the reporter constructs contain A, C, G, or T, respectively, at positions corresponding to the "XX" repeats. The rest of the target DNA boxes is equivalent to the Hax3 box.

Figure 27A:
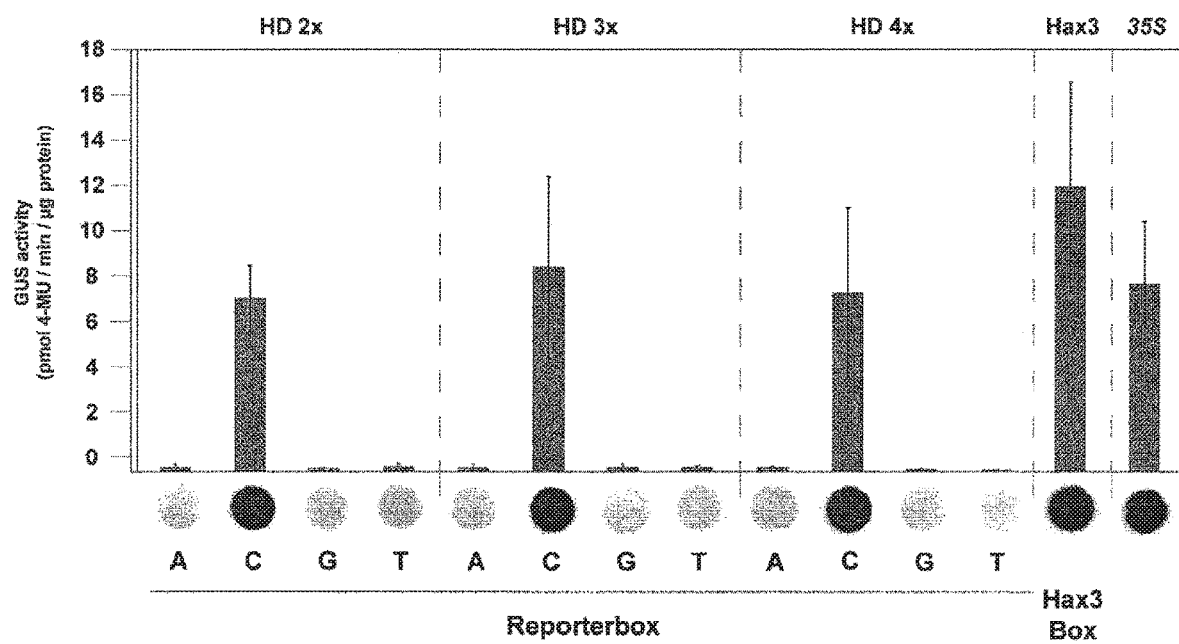
Figure 27B:
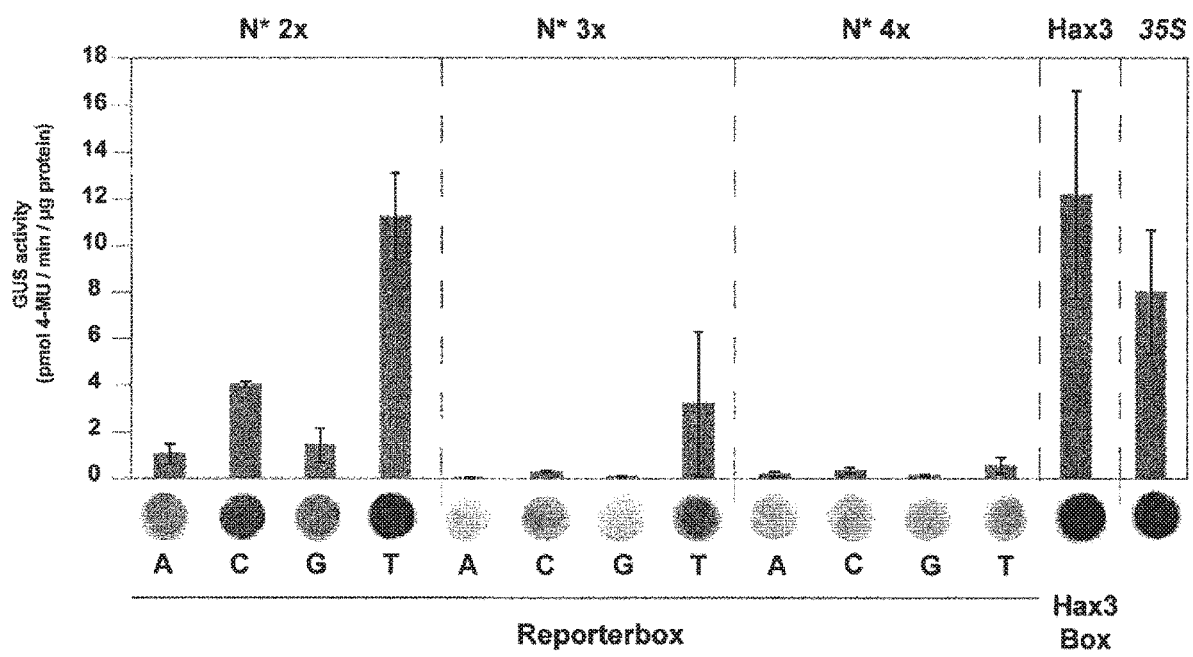
Figure 27C:
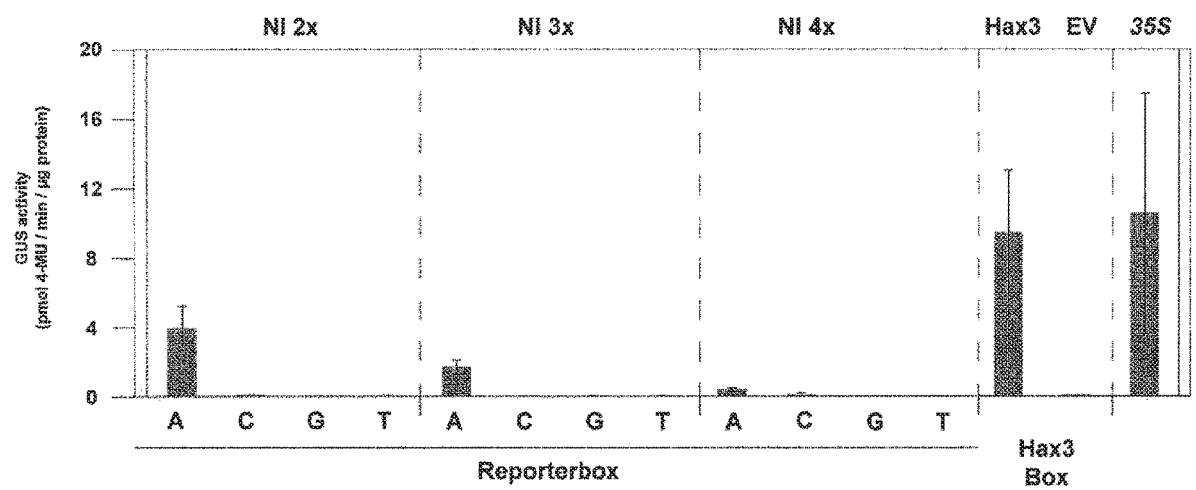

FIGS. 27A-27C. Experimental Setup to Study Specificity of Repeat Types with Low DNA Recognition Potential The artificial effectors were assembled to contain 4, 3, or 2 repeats, respectively, as "test repeats" with unknown specificity (designated X) in addition to Hax3 repeats (see, FIG. 26 for details). Target boxes in the reporter constructs contain A, C, G, or T, respectively, at positions corresponding to the test repeats. The rest of the target DNA boxes is equivalent to the Hax3 box. Although TALs with four or more combined N* repeats do not show a specificity, a combination of three or two N* repeats indicates a specificity for T, or T and C, respectively. N* and NI are obviously repeat types with weak DNA recognition properties. FIG. 27A: HD; FIG. 27B: N*; and FIG. 27C: NI.

SEQUENCE LISTING

The nucleotide and amino acid sequences listed in the accompanying figures and the sequence listing are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

A number of terms that are used throughout this disclosure are defined hereinbelow.

The term "repeat domain" is used to describe the DNA recognition domain from a TAL effector, or artificial version thereof that is made using the methods disclosed, consisting of modular repeat units that when present in a polypeptide confer target DNA specificity. A repeat domain comprised of repeat units can be added to any polypeptide in which DNA sequence targeting is desired and are not limited to use in TAL effectors.

The term "repeat unit" is used to describe the modular portion of a repeat domain from a TAL effector, or an artificial version thereof, that contains one amino acid or two adjacent amino acids that determine recognition of a base pair in a target DNA sequence. Repeat units taken together recognize a defined target DNA sequence and constitute a repeat domain. Repeat units can be added to any polypeptide in which DNA sequence targeting is desired and are not limited to use in TAL effectors.

The term "recognition code" is used to describe the relationship between the amino acids in positions 12 and 13 of a repeat unit and the corresponding DNA base pair in a target DNA sequence that such amino acids confer recognition of, as follows: HD for recognition of C/G; NI for recognition of A/T; NG for recognition of T/A; NS for recognition of C/G or A/T or T/A or G/C; NN for recognition of G/C or A/T; IG for recognition of T/A; N for recognition of C/G or T/A; HG for recognition of C/G or T/A; H for recognition of T/A; NK for recognition of G/C; NH for recognition of G/C; NP for recognition of A/T, C/G, or T/A; NT for recognition of A/T or G/C; NH for recognition of A/T or G/C; SH for recognition of G/C; SN for recognition of G/C; and IS for recognition of A/T. Additional specificities for the amino acids in positions in positions 12 and 13 of a repeat unit and the corresponding DNA base pair in a target DNA sequence have been reported: HA for recognition of C/G; ND for recognition of C/G; HI for recognition of C/G; HN for recognition of G/C; and NA for recognition of G/C (Moscou & Bogdanove (2009) *Science* 326:1501).

As used herein, "effector" (or "effector protein" or "effector polypeptide") refers to constructs or their encoded polypeptide products in which said polypeptide is able to recognize a target DNA sequence. The effector protein includes a repeat domain comprised of 1.5 or more repeat units and also may include one or more functional domains such as a regulatory domain. In preferred embodiments of the invention, the "effector" is additionally capable of exerting an effect, such as regulation of gene expression. Although the present invention is not dependent on a particularly biological mechanism, it is believe that the proteins or polypeptides of the invention that recognize a target DNA sequence bind to the target DNA sequence.

The term "naturally occurring" is used to describe an object that can be found in nature as distinct from being produced by man. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as-present in a wild-type individual, such as would be typical for the species.

The terms "modulating expression" "inhibiting expression" and "activating expression" of a gene refer to the ability of a polypeptide of the present invention to activate or inhibit transcription of a gene. Activation includes prevention of subsequent transcriptional inhibition (i.e., prevention of repression of gene expression) and inhibition includes prevention of subsequent transcriptional activation (i.e., prevention of gene activation). Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, beta-galactosidase, GFP (see, e.g., Mistili & Spector (1997) *Nature Biotechnology* 15:961-964); changes in signal transduction, phosphorylation and dephosphorylation, receptor-ligand interactions, second messenger concentrations (e.g., cGMP, cAMP, IP3, and Ca2+), cell growth, neovascularization, in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, calorimetric reactions, antibody binding, inducible markers, ligand binding assays; changes in intracellular second messengers such as cGMP and inositol triphosphate (IP3); changes in intracellular calcium levels; cytokine release, and the like.

A "regulatory domain" refers to a protein or a protein subsequence that has transcriptional modulation activity. Typically, a regulatory domain is covalently or non-covalently linked to a polypeptide of the present invention to modulate transcription. Alternatively, a polypeptide of the present invention can act alone, without a regulatory domain, or with multiple regulatory domains to modulate transcription. Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al. (1996) *Cell* 84:825 30 for a review of proteins and nucleic acid elements involved in transcription; transcription factors in general are reviewed in Barnes & Adcock (1995) *Clin. Exp. Allergy* 25 Suppl. 2:46 9 and Roeder (1996) *Methods Enzymol.* 273:165 71). Databases dedicated to transcription factors are known (see, e.g., *Science* (1995) 269:630). Nuclear hormone receptor transcription factors are described in, for example, Rosen et al. (1995) *J. Med. Chem.* 38:4855 74. The C/EBP family of transcription factors are reviewed in Wedel et al. (1995) *Immunobiology* 193:171 85. Coactivators and co-repressors that mediate transcription regulation by nuclear hormone receptors are reviewed in, for example, Meier (1996) *Eur. J Endocrinol.* 134(2):158 9; Kaiser et al. (1996) *Trends Biochem. Sci.* 21:342 5; and Utley et al. (1998) *Nature* 394:498 502). GATA transcription factors, which are involved in regulation of hematopoiesis, are described in, for example, Simon (1995) *Nat. Genet.* 11:9 11; Weiss et al. (1995) *Exp. Hematol.* 23:99-107. TATA box binding protein (TBP) and its associated TAF polypeptides (which include TAF30, TAF55, TAF80, TAF110, TAF150, and TAF250) are described in Goodrich & Tjian (1994) *Curr. Opin. Cell Biol.* 6:403 9 and Hurley (1996) Curr. Opin. Struct. Biol. 6:69 75. The STAT family of transcription factors are reviewed in, for example, Barahmand-Pour et al. (1996) *Curr. Top. Microbiol. Immunol.* 211:121 8. Transcription factors involved in disease are reviewed in Aso et al. (1996) *J. Clin. Invest.* 97:1561 9. Kinases, phosphatases, and other proteins that modify polypeptides involved in gene regulation are also useful as regulatory domains for polypeptides of the present invention. Such modifiers are often involved in switching on or off transcription mediated by, for example, hormones. Kinases involved in transcription regulation are reviewed in Davis (1995) *Mol. Reprod. Dev.* 42:459 67, Jackson et al. (1993) *Adv. Second Messenger Phosphoprotein Res.* 28:279 86, and Boulikas (1995) *Crit. Rev. Eukaryot. Gene Expr.* 5:1 77, while phosphatases are reviewed in, for example, Schonthal & Semin (1995) *Cancer Biol.* 6:239 48. Nuclear tyrosine kinases are described in Wang (1994) *Trends Biochem. Sci.* 19:373 6. Useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes,* 2nd ed., The Jones and Bartlett Series in Biology, Boston, Mass., Jones and Bartlett Publishers, 1995. The ets transcription factors are reviewed in Waslylk et al. (1993) *Eur. J. Biochem.* 211:7 18 and Crepieux et al. (1994) *Crit. Rev. Oncog.* 5:615 38. Myc oncogenes are reviewed in, for example, Ryan et al. (1996) *Biochem.* 1 314:713 21. The jun and fos transcription factors are described in, for example, The Fos and Jun Families of Transcription Factors, Angel & Herrlich, eds. (1994). The max oncogene is reviewed in Hurlin et al. *Cold Spring Harb. Symp. Quant. Biol.* 59:109 16. The myb gene family is reviewed in Kanei-Ishii et al. (1996) *Curr. Top. Microbiol. Immunol.* 211:89 98. The mos family is reviewed in Yew et al. (1993) *Curr. Opin. Genet. Dev.* 3:19 25. Polypeptides of the present invention can include regulatory domains obtained from DNA repair enzymes and their associated factors and modifiers. DNA repair systems are reviewed in, for example, Vos (1992) *Curr. Opin. Cell Biol.* 4:385 95;

Sancar (1995) *Ann. Rev. Genet.* 29:69 105; Lehmann (1995) *Genet. Eng.* 17:1 19; and Wood (1996) *Ann. Rev. Biochem.* 65:135 67. DNA rearrangement enzymes and their associated factors and modifiers can also be used as regulatory domains (see, e.g., Gangloff et al. (1994) *Experientia* 50:261 9; Sadowski (1993) *FASEB J.* 7:760 7).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al. (1994) Bioessays 16:13 22, and methyltransferases are described in Cheng (1995) *Curr. Opin. Struct. Biol.* 5:4 10. Chromatin associated proteins and their modifiers (e.g., kinases, acetylases and deacetylases), such as histone deacetylase (Wolffe Science 272:371 2 (1996)) are also useful as domains for addition to the effector of choice. In one preferred embodiment, the regulatory domain is a DNA methyl transferase that acts as a transcriptional repressor (see, e.g., Van den Wyngaert et al. FEBS Lett. 426:283 289 (1998); Flynn et al. J. Mol. Biol. 279:101 116 (1998); Okano et al. Nucleic Acids Res. 26:2536 2540 (1998); and Zardo & Caiafa, J. Biol. Chem. 273:16517 16520 (1998)). In another preferred embodiment, endonucleases such as FokI are used as transcriptional repressors, which act via gene cleavage (see, e.g., WO95/09233; and PCT/US94/01201). Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto (1998) *Mol. Cell. Biol.* 18:4377 4384; Wolffe (1996) *Science* 272:371 372; Taunton et al. *Science* 272:408 411 (1996); and Hassig et al. PNAS 95:3519 3524 (1998)). In another embodiment, histone deacetylase is used as a transcriptional repressor (see, e.g., Jin & Scotto (1998) *Mol. Cell. Biol.* 18:4377 4384; Syntichaki & Thireos (1998) *J. Biol. Chem.* 273:24414 24419; Sakaguchi et al. (1998) *Genes Dev.* 12:2831 2841; and Martinez et al. (1998) *J. Biol. Chem.* 273:23781 23785).

As used herein, "gene" refers to a nucleic acid molecule or portion thereof which comprises a coding sequence, optionally containing introns, and control regions which regulate the expression of the coding sequence and the transcription of untranslated portions of the transcript. Thus, the term "gene" includes, besides coding sequence, regulatory sequence such as the promoter, enhancer, 5' untranslated regions, 3' untranslated region, termination signals, poly adenylation region and the like. Regulatory sequence of a gene may be located proximal to, within, or distal to the coding region.

As used herein, "target gene" refers to a gene whose expression is to be modulated by a polypeptide of the present invention.

As used herein, "plant" refers to any of various photosynthetic, eucaryotic multi-cellular organisms of the kingdom Plantae, characteristically producing embryos, containing chloroplasts, having cellulose cell walls and lacking locomotion. As used herein, "plant" includes any plant or part of a plant at any stage of development, including seeds, suspension cultures, embryos, meristematic regions, callus tissue, leaves, roots, shoots, gametophytes, sporophytes, pollen, microspores, and progeny thereof. Also included are cuttings, and cell or tissue cultures. As used in conjunction with the present invention, the term "plant tissue" includes, but is not limited to, whole plants, plant cells, plant organs, e.g., leafs, stems, roots, meristems, plant seeds, protoplasts, callus, cell cultures, and any groups of plant cells organized into structural and/or functional units.

As used herein, "modulate the expression of a target gene in plant cells" refers to increasing (activation) or decreasing (repression) the expression of the target gene in plant cells with a polypeptide of the present invention, alone or in combination with other transcription and/or translational regulatory factors, or nucleic acids encoding such polypeptide, in plant cells.

As used herein, a "target DNA sequence" refers to a portion of double-stranded DNA to which recognition by a protein is desired. In one embodiment, a "target DNA sequence" is all or part of a transcriptional control element for a gene for which a desired phenotypic result can be attained by altering the degree of its expression. A transcriptional control element includes positive and negative control elements such as a promoter, an enhancer, other response elements, e.g., steroid response element, heat shock response element, metal response element, a repressor binding site, operator, and/or a silencer. The transcriptional control element can be viral, eukaryotic, or prokaryotic. A "target DNA sequence" also includes a downstream or an upstream sequence which can bind a protein and thereby modulate, typically prevent, transcription.

The use of the term "DNA" or "DNA sequence" herein is not intended to limit the present invention to polynucleotide molecules comprising DNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like.

Furthermore, it is understood by those of ordinary skill in the art that the DNA sequences disclosed herein also encompasses the complement of that exemplified nucleotide sequence.

As used herein, "specifically binds to a target DNA sequence" means that the binding affinity of a polypeptide of the present invention to a specified target DNA sequence is statistically higher than the binding affinity of the same polypeptide to a generally comparable, but non-target DNA sequence. It also refers to binding of a repeat domain of the present invention to a specified target DNA sequence to a detectably greater degree, e.g., at least 1.5-fold over background, than its binding to non-target DNA sequences and to the substantial exclusion of non-target DNA sequences. A polypeptide of the present invention's Kd to each DNA sequence can be compared to assess the binding specificity of the polypeptide to a particular target DNA sequence.

As used herein, a "target DNA sequence within a target gene" refers to a functional relationship between the target DNA sequence and the target gene in that recognition of a polypeptide of the present invention to the target DNA sequence will modulate the expression of the target gene. The target DNA sequence can be physically located anywhere inside the boundaries of the target gene, e.g., 5' ends, coding region, 3' ends, upstream and downstream regions outside of cDNA encoded region, or inside enhancer or other regulatory region, and can be proximal or distal to the target gene.

As used herein, "endogenous" refers to nucleic acid or protein sequence naturally associated with a target gene or a host cell into which it is introduced.

As used herein, "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

As used herein, "genetically modified plant (or transgenic plant)" refers to a plant which comprises within its genome an exogenous polynucleotide. Generally, and preferably, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "minimal promoter" or substantially similar term refers to a promoter element, particularly a TATA element, that is inactive or that has greatly reduced promoter activity in the absence of upstream activation. In the presence of a suitable transcription factor, the minimal promoter functions to permit transcription.

As used herein, "repressor protein" or "repressor" refers to a protein that binds to operator of DNA or to RNA to prevent transcription or translation, respectively.

As used herein, "repression" refers to inhibition of transcription or translation by binding of repressor protein to specific site on DNA or mRNA. Preferably, repression includes a significant change in transcription or translation level of at least 1.5 fold, more preferably at least two fold, and even more preferably at least five fold.

As used herein, "activator protein" or "activator" refers to a protein that binds to operator of DNA or to RNA to enhance transcription or translation, respectively.

As used herein, "activation" refers to enhancement of transcription or translation by binding of activator protein to specific site on DNA or mRNA. Preferably, activation includes a significant change in transcription or translation level of at least 1.5 fold, more preferably at least two fold, and even more preferably at least five fold.

As used herein, "derivative" or "analog" of a molecule refers to a portion derived from or a modified version of the molecule.

As used herein, a "repeat unit derived from a transcription activator-like (TAL) effector" refers to a repeat unit from a TAL effector or a modified or artificial version of one or more TAL effectors that is produced by any of the methods disclosed herein.

In the following, the invention is specifically described with respect to the transcription activator-like (TAL) effector family which are translocated via the type III secretion system into plant cells. The type member of this effector family is AvrBs3. Hence, the TAL effector family is also named AvrBs3-like family of proteins. Both expressions are used synonymously and can be interchanged. Non-limiting examples of the AvrBs3-like family are as follows: AvrBs4 and the members of the Hax sub-family Hax2, Hax3, and Hax4 as well as Brg11. AvrBs3 and the other members of its family are characterized by their binding capability to specific DNA sequences in promoter regions of target genes and induction of expression of these genes. They have conserved structural features that enable them to act as transcriptional activators of plant genes. AvrBs3-like family and homologous effectors typically have in their C-terminal region nuclear localisation sequences (NLS) and a transcriptional activation domain (AD). The central region contains repeat units of typically 34 or 35 amino acids. The repeat units are nearly identical, but variable at certain positions and it has now been found how these positions determine the nucleotide sequence binding specificity of the proteins.

It was shown for AvrBs3 that the repeat units are responsible for binding to DNA. The DNA-binding specificity of AvrBs3 and probably other members of the AvrBs3-family seems to be mediated by the central repeat domain of the proteins. This repeat domain consists in AvrBs3 of 17.5 repeat units and in homologous proteins is comprised of 1.5 to 33.5 repeat units which are typically 34 amino acids each. Other repeat unit lengths are also known (e.g. 30, 33, 35, 39, 40, 42 amino acids). The last repeat in the repeat domain is usually only a half repeat of 19 or 20 amino acids length. The individual repeat units are generally not identical. They vary at certain variable amino acid positions, among these positions 12 and 13 are hypervariable while positions 4, 11, 24, and 32 vary with high frequency but at a lower frequency than 12 and 13 (variations at other positions occur also, but at lower frequency). The comparison of different AvrBs3-like proteins from Xanthomonas reveals 80 to 97% overall sequence identity with most differences confined to the repeat domain. For example, AvrBs3 and the AvrBs3-like family member AvrBs4 differ exclusively in their repeat domain region, with the exception of a four amino acid deletion in the C-terminus of AvrBs4 with respect to AvrBs3.

In FIG. 16, the amino acid sequences of AvrBs3 as well as the amino acid sequences of the members of the Hax-sub family are shown. Of particular importance for the present invention is the repeat units, which are identical except for the hypervariable amino acids at positions 12 and 13 and the variable amino acids at positions 4 and 24. Hence, each repeat unit of these proteins is given separately.

As stated above, it has already been described that the repeat units within the repeat domains determine recognition or binding capability and specificity of type III effector proteins of AvrBs3-family. However, the principle underlying was not known until the present invention.

The inventors have discovered that one repeat unit within a repeat domain is responsible for the recognition of one specific DNA base pair in a target DNA sequence. This finding is, however, only one element of the invention. The inventors additionally discovered that a hypervariable region within each repeat unit of a repeat domain is responsible for recognition of one specific DNA base pair in a target DNA sequence. Within a repeat unit, the hypervariable region (corresponds to amino acid positions 12 and 13) are typically responsible for this recognition specificity. Hence each variation in these amino acids reflects a corresponding variation in target DNA recognition and preferably also recognition capacity.

As used herein, "hypervariable region" is intended to mean positions 12 and 13 or equivalent position in a repeat unit of the present invention. It is recognized that positions 12 and 13 of the invention correspond to positions 12 and 13 in the full-length repeat units of AvrBs3 and other TAL effectors as disclosed herein. It is further recognized that by "equivalent positions" is intended positions that corresponds to positions 12 and 13, respectively, in a repeat unit of the present. One can readily determine such equivalent positions by aligning any repeat unit with a full-length repeat unit of AvrBs3.

It has, therefore, been shown for the first time that one repeat unit in a repeat domain of a DNA-binding protein recognizes one base pair in the target DNA, and that one amino acid or two adjacent amino acid residues in a repeat unit, typically within the hypervariable regions of a repeat unit, determine which base pair in the target DNA is recognized. Based on this finding, a person skilled in the art would be able to specifically target base pairs in a target DNA sequence of interest by modifying a polypeptide within its repeat units of the repeat domain to specifically target base pairs in the desired target DNA sequence. Based on this finding, the inventors have identified a recognition code for DNA-target specificities of different repeat types and were able to predict target DNA sequences of several TAL effectors which could be confirmed experimentally. This will additionally facilitate the identification of host genes that are regulated by TAL effectors. The linear array of repeat units which recognizes a linear sequence of bases in the target DNA is a novel DNA-protein interaction. The modular architecture of the repeat domain and the recognition code identified by the inventors for targeting DNA with high specificity allows the efficient design of specific DNA-binding domains for use in a variety of technological fields.

In one embodiment of the present invention, the repeat domains are included in a transcription factor, for instance in transcription factors active in plants, particularly preferred in type III effector proteins, e.g. in effectors of the AvrBs3-like family. However, after having uncovered the correlation between the repeat units in a repeat domain on the one hand and the base sequence in the target DNA on the other hand, the modular architecture of the repeat domain can be used in any protein which shall be used for targeting specific target DNA sequences. By introducing repeat domains comprising repeat units into a polypeptide wherein the repeat units are modified in order to comprise one hypervariable region per repeat unit and wherein the hypervariable region determines recognition of a base pair in a target DNA sequence, the recognition of a large variety of proteins to pre-determined target DNA sequences will be available.

As one repeat unit within a repeat domain has been found to be responsible for the specific recognition of one base pair in a DNA, several repeat units can be combined with each other wherein each repeat unit includes a hypervariable region that is responsible for the recognition of each repeat unit to a particular base pair in a target DNA sequence.

Techniques to specifically modify DNA sequences in order to obtain a specified codon for a specific amino acid are known in the art.

Methods for mutagenesis and polynucleotide alterations have been widely described. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. All these publications are herein incorporated by reference.

The following examples provide methods for constructing new repeat units and testing the specific binding activities of artificially constructed repeat units specifically recognizing base pairs in a target DNA sequence.

The number of repeat units to be used in a repeat domain can be ascertained by one skilled in the art by routine experimentation. Generally, at least 1.5 repeat units are considered as a minimum, although typically at least about 8 repeat units will be used. The repeat units do not have to be complete repeat units, as repeat units of half the size can be used. Moreover, the methods and polypeptides disclosed herein do depend on repeat domains with a particular number of repeat units. Thus, a polypeptide of the invention can comprise, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13. 5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 46, 46.5, 47, 47.5, 48, 48.5, 49, 49.5, 50, 50.5 or more repeat units. Typically, AvrBs3 contains 17.5 repeat units and induces expression of UPA (up-regulated by AvrBs3) genes. The number and order of repeat units will determine the corresponding activity and DNA recognition specificity. As further examples, the AvrBs3 family members Hax2 includes 21.5 repeat units, Hax3 11.5 repeat units and Hax4 14.5 repeat units. Preferably, a polypeptide of the invention comprises about 8 and to about 39 repeat units. More preferably, a polypeptide of the invention comprises about 11.5 to about 33.5 repeat units.

A typical consensus sequence of a repeat with 34 amino acids (in one-letter code) is shown below:

(SEQ ID NO: 119)
LTPEQVVAIASNGGGKQALETVQRLLPVLCQAHG

A further consensus sequence for a repeat unit with 35 amino acids (in one-letter code) is as follows:

(SEQ ID NO: 120)
LTPEQVVAIASNGGGKQALETVQRLLPVLCQAPHD

The repeat units which can be used in one embodiment of the invention have an identity with the consensus sequences described above of at least 35%, 40%, 50%, 60%, 70%, 75%, 80%, 85%, 90% or 95%. In preferred embodiments, the repeat sequences of AvrBs3, Hax2, Hax3 and Hax4 and further members of the AvrBs3-family are used. The repeat unit sequences of these members are indicated in FIG. 16. These repeat unit sequences can be modified by exchanging one or more of the amino acids. The modified repeat unit sequences have an identity with the original repeat sequence of the original member of the AvrBs3-family sequence of at least 35%, 40%, 50%, 60%, 70%,75%, 80%, 85%, 90% or 95%. In preferred embodiments, the amino acids in positions 12 and 13 are altered. In still further embodiments, amino acids in positions 4, 11, 24, and 32 are altered. Preferably, the number of amino acids per repeat are in a range between 20-45 amino acids, furthermore 32-40 amino acids, still further 32-39 amino acid, and further optionally 32, 34, 35 or 39 amino acids per repeat unit.

Specifically, the hypervariable region in a repeat unit determines the specific recognition of one base pair in a target DNA sequence. More specifically, the inventors have found the following correlation of recognition specificity between amino acids found at positions 12 and 13 in a repeat unit and base pairs in the target DNA sequence:

HD for recognition of C/G
NI for recognition of A/T
NG for recognition of T/A
NS for recognition of C/G or A/T or T/A or G/C
NN for recognition of G/C or A/T
IG for recognition of T/A
N for recognition of C/G or T/A
HG for recognition of T/A
H for recognition of T/A
NK for recognition of G/C
NH for recognition of G/C
NP for recognition of A/T or C/G or T/A
NT for recognition of A/T or G/C
HN for recognition of A/T or G/C
SH for recognition of G/C
SN for recognition of G/C and
IS for recognition of A/T.

It has to be noted that the amino acids are represented in the single letter code. The nucleotides are given as base pairs, wherein the first base is located in the upper strand and the second base in the lower strand; for example C/G means that C is located in the upper strand, G in the lower strand.

The methods of the present invention can further comprise making a repeat unit in which one or more of the hypervariable regions is selected from the following group in order to determine recognition of one of the following base pairs: HA for recognition of C/G; ND for recognition of C/G; HI for recognition of C/G; HN for recognition of G/C; and NA for recognition of G/C.

With respect to the single amino acids N and H, respectively, amino acid 13 of AvrBs3 appears to be missing from the repeat unit when compared by multiple amino acid sequence alignments with the other repeat units.

In one embodiment of the invention, the N-terminal domain of AvrBs3-like proteins confers recognition specificity for a T, 5' of the recognition specificity of said repeat.

In a particularly preferred embodiment of the invention, repeat units of the protein family AvrBs3 are used. Examples for the members of this protein family have been specified above. Particularly, the members of the protein family have an amino acid homology of at least 95%, at least 90%, at least 80%, at least 85%, at least 70%, at least 75%, at least 60%, at least 50%, at least 40% or at least 35% to the amino acid sequence of AvrBs3, particularly to the amino acid sequence of the repeat unit of AvrBs3. Having this in mind, the hypervariable region in a repeat unit can be deduced by an amino acid comparison between the members of the AvrBs3 family. In particularly preferred embodiments, the amino acids are in positions 12 and 13 of a repeat unit of AvrBs3. However, variable regions may also be located in different amino acid positions. Examples for variable positions are amino acids numbers 4, 11, 24, and 32. In a further embodiment of the invention, the amino acids responsible for the specific recognition of a base pair in a DNA sequence are located in positions which typically do not vary between the members of the AvrBs3 family or in positions which are variable but not hypervariable.

To summarize, the inventors have found that repeat units determine the recognition of one base pair on a DNA sequence and that the hypervariable region within a repeat unit determines the recognition specificity of the corresponding repeat unit. Hence, the sequence of repeat units correlates with a specific linear order of base pairs in a target DNA sequence. The inventors have found this correlation with respect to AvrBs3 and verified it with respect to a representative number of members of the AvrBs3-like family of proteins. With respect to AvrBs3-like family members, amino acid residues in positions 12 and 13 in a repeat unit of 34 or other amino acids length correlate with defined binding specificities of AvrBs3-like proteins. The discovery of this core principle provides a powerful tool to customize a polypeptide with its cognate target DNA template for a variety of applications including, but not limited to, modulation of gene expression and targeted genome engineering.

In the present invention, polypeptides can be designed which comprise a repeat domain with repeat units wherein in the repeat units hypervariable regions are included which determine recognition of a base pair in a target DNA sequence. In one embodiment of the invention, each repeat unit includes a hypervariable region which determine recognition of one base pair in a target DNA sequence. In a further embodiment, 1 or 2 repeat units in a repeat domain are included which do not specifically recognize a base pair in a target DNA sequence. Considering the recognition code found by the inventors, a modular arrangement of repeat units is feasible wherein each repeat unit is responsible for the specific recognition of one base pair in a target DNA sequence. Consequently, a sequence of repeat units corresponds to a sequence of base pairs in a target DNA sequence so that 1 repeat unit matches to one base pair.

Provided that a target DNA sequence is known and to which recognition by a protein is desired, the person skilled in the art is able to specifically construct a modular series of repeat units, including specific recognition amino acid sequences, and assemble these repeat units into a polypeptide in the appropriate order to enable recognition of and binding to the desired target DNA sequence. Any polypeptide can be modified by being combined with a modular repeat unit DNA-binding domain of the present invention. Such examples include polypeptides that are transcription activator and repressor proteins, resistance-mediating proteins, nucleases, topoisomerases, ligases, integrases, recombinases, resolvases, methylases, acetylases, demethylases, deacetylases, and any other polypeptide capable of modifying DNA, RNA, or proteins.

The modular repeat unit DNA-binding domain of the present invention can be combined with cell compartment localisation signals such as nuclear localisation signals, to function at any other regulatory regions, including but not limited to, transcriptional regulatory regions and translational termination regions.

In a further embodiment of the invention, these modularly designed repeat units are combined with an endoneclease domain capable of cleaving DNA when brought into proximity with DNA as a result of binding by the repeat domain. Such endonucleolytic breaks are known to stimulate the rate of homologous recombination in eukaryotes, including fungi, plants, and animals. The ability to simulate homologous recombination at a specific site as a result of a site-specific endonucleolytic break allows the recovery of transformed cells that have integrated a DNA sequence of interest at the specific site, at a much higher frequency than is possible without having made the site-specific break. In addition, endonucleolytic breaks such as those caused by polypeptides formed from a repeat domain and an endonuclease domain are sometimes repaired by the cellular DNA metabolic machinery in a way that alters the sequence at the site of the break, for instance by causing a short insertion or deletion at the site of the break compared to the unaltered sequence. These sequence alterations can cause inactivation of the function of a gene or protein, for instance by altering a protein-coding sequence to make a non-functional protein, modifying a splice site so that a gene transcript is not properly cleaved, making a non-functional transcript, changing the promoter sequence of a gene so that it can no longer by appropriately transcribed, etc.

Breaking DNA using site specific endonucleases can increase the rate of homologous recombination in the region of the breakage. In some embodiments, the Fok I (Flavobacterium okeanokoites) endonuclease may be utilized in an effector to induce DNA breaks. The Fok I endonuclease domain functions independently of the DNA binding domain and cuts a double stranded DNA typically as a dimer (Li et al. (1992) *Proc. Natl. Acad. Sci. U.S.A* 89 (10):4275-4279, and Kim et al. (1996) *Proc. Natl. Acad. Sci. U.S.A* 93 (3):1156-1160; the disclosures of which are incorporated herein by reference in their entireties). A single-chain FokI dimer has also been developed and could also be utilized (Mino et al. (2009) *J. Biotechnol.* 140:156-161). An effector could be constructed that contains a repeat domain for recognition of a desired target DNA sequence as well as a FokI endonuclease domain to induce DNA breakage at or near the target DNA sequence similar to previous work done employing zinc finger nucleases (Townsend et al. (2009) Nature 459:442-445; Shukla et al. (2009) Nature 459, 437-441, all of which are herein incorporated by reference in their entireties). Utilization of such effectors could enable the generation of targeted changes in genomes which include additions, deletions and other modifications, analogous to those uses reported for zinc finger nucleases as per Bibikova et al. (2003) *Science* 300, 764; Urnov et al. (2005) *Nature* 435, 646; Wright et al. (2005) *The Plant Journal* 44:693-705; and U.S. Pat. Nos. 7,163,824 and 7,001,768, all of which are herein incorporated by reference in their entireties.

The FokI endonuclease domain can be cloned by PCR from the genomic DNA of the marine bacteria *Flavobacterium okeanokoites* (ATCC) prepared by standard methods. The sequence of the FokI endonuclease is available on Pubmed (Acc. No. M28828 and Acc. No J04623, the disclosures of which are incorporated herein by reference in their entireties). The I-Sce I endonuclease from the yeast Saccharomyces cerevisiae has been used to produce DNA breaks that increase the rate of homologous recombination. I-Sce I is an endonuclease encoded by a mitochondrial intron which has an 18 bp recognition sequence, and therefore a very low frequency of recognition sites within a given DNA, even within large genomes (Thierry et al. (1991) *Nucleic Acids Res.* 19 (1):189-190; the disclosure of which is incorporated herein by reference in its entirety). The infrequency of cleavage sites recognized by I-SceI makes it suitable to use for enhancing homologous recombination. Additional description regarding the use of I-Sce I to induce said DNA breaks can be found in U.S. Pat. Appl. 20090305402, which is incorporated herein by reference in its entirety.

The recognition site for I-Sce I has been introduced into a range of different systems. Subsequent cutting of this site with I-Sce I increases homologous recombination at the position where the site has been introduced. Enhanced frequencies of homologous recombination have been obtained with I-Sce I sites introduced into the extra-chromosomal DNA in *Xenopus* oocytes, the mouse genome, and the genomic DNA of the tobacco plant Nicotiana plumbaginifolia. See, for example, Segal et al. (1995) *Proc. Natl. Acad. Sci. U.S.A.* 92 (3):806-810; Choulika et al. (1995) *Mol. Cell Biol.* 15 (4):1968-1973; and Puchta et al. (1993) *Nucleic Acids Res.* 21 (22):5034-5040; the disclosures of which are incorporated herein by reference in their entireties. It will be appreciated that any other endonuclease domain that works with heterologous DNA binding domains can be utilized in an effector and that the I-Sce I endonuclease is one such non-limiting example. The limitation of the use of endonucleases that have a DNA recognition and binding domain such as I-Sce I is that the recognition site has to be introduced by standard methods of homologous recombination at the desired location prior to the use of said endonuclease to enhance homologous recombination at that site, if such site is not already present in the desired location. Methods have been reported that enable the design and synthesis of novel endonucleases, such as by modifying known endonucleases or making chimeric versions of one or more such endonucleases, that recognize novel target DNA sequences, thus paving the way for generation of such engineered endonuclease domains to cleave endogenous target DNA sequences of interest (Chevalier et al. (2002) *Molecular Cell* 10:895-905; WO2007/060495; WO2009/095793; Fajardo-Sanchez et al. (2008) *Nucleic Acids Res.* 36:2163-2173, both of which are incorporated by reference in their entireties). As such, it could be envisioned that such endonuclease domains could be similarly engineered so as to render the DNA-binding activity non-functional but leaving the DNA cleaving function active and to utilize said similarly engineered endonuclease cleavage domain in an effector to induce DNA breaks similar to the use of FokI above. In such applications, target DNA sequence recognition would preferably be provided by the repeat domain of the effector but DNA cleavage would be accomplished by the engineered endonuclease domain.

As mentioned above, an effector includes a repeat domain with specific recognition for a desired specific target sequence. In preferred embodiments, the effector specifically binds to an endogenous chromosomal DNA sequence. The specific nucleic acid sequence or more preferably specific endogenous chromosomal sequence can be any sequence in a nucleic acid region where it is desired to enhance homologous recombination. For example, the nucleic acid region may be a region which contains a gene in which it is desired to introduce a mutation, such as a point mutation or deletion, or a region into which it is desired to introduce a gene conferring a desired phenotype.

Further embodiments relate to methods of generating a modified plant in which a desired addition has been introduced. The methods can include obtaining a plant cell that includes an endogenous target DNA sequence into which it is desired to introduce a modification; generating a double-stranded cut within the endogenous target DNA sequence with an effector that includes a repeat domain that binds to an endogenous target DNA sequence and an endonuclease domain; introducing an exogenous nucleic acid that includes a sequence homologous to at least a portion of the endogenous target DNA into the plant cell under conditions which permit homologous recombination to occur between the exogenous nucleic acid and the endogenous target DNA sequence; and generating a plant from the plant cell in which homologous recombination has occurred. Other embodiments relate to genetically modified cells and plants made according to the method described above and herein. It should be noted that the target DNA sequence could be artificial or naturally occurring. It will be appreciated that such methods could be used in any organism (such non-limiting organisms to include animals, humans, fungi, oomycetes bacteria and viruses) using techniques and methods known in the art and utilized for such purposes in such organisms.

In a further embodiment of the invention, these modularly designed repeat domains are combined with one or more domains responsible for the modulation or control of the expression of a gene, for instance of plant genes, animal genes, fungal genes, oomycete genes, viral genes, or human genes. Methods for modulating gene expression by generating DNA-binding polypeptides containing zinc finger domains is known in the art (U.S. Pat. Nos. 7,285,416, 7,521,241, 7,361,635, 7,273,923, 7,262,054, 7,220,719, 7,070,934, 7,013,219, 6,979,539, 6,933,113, 6,824,978, each of which is hereby herein incorporated by reference in its entirety). For instance, these effectors of the AvrBs3-like family are modified in order to bind to specific target DNA sequences. Such polypeptides might for instance be transcription activators or repressor proteins of transcription which are modified by the method of the present invention to specifically bind to genetic control regions in a promoter of or other regulatory region for a gene of interest in order to activate, repress or otherwise modulate transcription of said gene.

In a still further embodiment of the invention, the target DNA sequences are modified in order to be specifically recognized by a naturally occurring repeat domain or by a modified repeat domain. As one example, the target DNA sequences for members of the AvrBs3-like family can be inserted into promoters to generate novel controllable promoters that can be induced by the corresponding AvrBs3 effector. Secondary inducible systems can be constructed using a trans-activator and a target gene, wherein the trans-activator is a polypeptide wherein said polypeptide comprises at least a repeat domain comprising repeat units of the present invention that bind to said target gene and induce expression. The trans-activator and the target gene can be introduced into one cell line but may also be present in different cell lines and later be introgressed. In a further embodiment, disease-resistant plants can be constructed by inserting the target DNA sequence of a repeat domain containing polypeptide of the present invention in front of a gene which after expression leads to a defence reaction of the plant by activating a resistance-mediating gene.

In a further embodiment, custom DNA-binding polypeptides can be constructed by rearranging repeat unit types thus allowing the generation of repeat domains with novel target DNA binding specificity. Individual repeat units are nearly identical at the DNA level which precludes classical cloning strategies. The present invention provides a quick and inexpensive strategy to assemble custom polypeptides with repeat domains of the present invention. To improve cloning versatility such polypeptides, a two-step assembly method was designed. This method was used to assemble polypeptides with novel repeat types to study their target DNA recognition and binding specificity.

Summarly, any DNA sequence can be modified to enable binding by a repeat domain containing polypeptide of the present invention by introducing base pairs into any DNA region or specific regions of a gene or a genetic control element to specifically target a polypeptide having a repeat domain comprised of repeat units that will bind said modified DNA sequence in order to facilitate specific recognition and binding to each other.

The inventors have demonstrated that a truly modular DNA recognizing and preferably binding polypeptide can be efficiently produced, wherein the binding motif of said polypeptide is a repeat domain comprised of repeat units which are selected on the basis of their recognition capability of a combination of particular base pairs. Accordingly, it should be well within the capability of one of normal skill in the art to design a polypeptide capable of binding to any desired target DNA sequence simply by considering the sequence of base pairs present in the target DNA and combining in the appropriate order repeat units as binding motifs having the necessary characteristics to bind thereto. The greater the length of known sequence of the target DNA, the greater the number of modular repeat units that can be included in the polypeptide. For example, if the known sequence is only 9 bases long, then nine repeat units as defined above can be included in the polypeptide. If the known sequence is 27 bases long, then up to 27 repeat units could be included in the polypeptide. The longer the target DNA sequence, the lower the probability of its occurrence in any other given portion of DNA elsewhere in the genome.

Moreover, those repeat units selected for inclusion in the polypeptide could be artificially modified in order to modify their binding characteristics. Alternatively (or additionally) the length and amino acid sequence of the repeat unit could be varied as long as its binding characteristic is not affected.

Generally, it will be preferred to select those repeat units having high affinity and high specificity for the target DNA sequence.

As described herein, effectors can be designed to recognize any suitable target site, for regulation of expression of any endogenous gene of choice. Examples of endogenous genes suitable for regulation include VEGF, CCR5, ER.alpha., Her2/Neu, Tat, Rev, HBV C, S, X, and P, LDL-R, PEPCK, CYP7, Fibrinogen, ApoB, Apo E, Apo(a), renin, NF-.kappa.B, I-.kappa.B, TNF-.alpha., FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, disease resistance genes, and other disease-related genes.

In another aspect, a method of modulating expression of a target gene in a cell is provided. The cell may be preferably a plant cell, a human cell, animal cell, fungal cell or any other living cell. The cells contain a polypeptide wherein said polypeptide comprises at least a repeat domain comprising repeat units, and these repeat units contain a hypervariable region and each repeat unit is responsible for the recognition of 1 base pair in said target DNA sequence. Said polypeptide is introduced either as DNA encoding for the polypeptide or the polypeptide is introduced per se into the cell by methods known in the art. Regardless of how introduced, the polypeptide should include at least one repeat domain that specifically recognizes and preferably binds to a target DNA sequence of base pairs and modulates the expression of a target gene. In a preferred embodiment, all repeat units contain a hypervariable region which determines recognition of base pairs in a target DNA sequence.

Examples of peptide sequences which can be linked to an effector of the present invention, for facilitating uptake of effectors into cells, include, but are not limited to: an 11 animo acid peptide of the tat protein of HIV; a 20 residue peptide sequence which corresponds to amino acids 84 103 of the p16 protein (see Fahraeus et al. (1996) *Current Biology* 6:84); the third helix of the 60-amino acid long homeodomain of Antennapedia (Derossi et al. (1994) *J. Biol. Chem.* 269:10444); the h region of a signal peptide such as the Kaposi fibroblast growth factor (K-FGF) h region; or the VP22 translocation domain from HSV (Elliot & O'Hare (1997) *Cell* 88:223 233). Other suitable chemical moieties that provide enhanced cellular uptake may also be chemically linked to effectors.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including Clostridium perfringens iota toxin, diphtheria toxin (DT), Pseudomonas exotoxin A (PE), pertussis toxin (PT), Bacillus anthracis toxin, and pertussis adenylate cyclase (CYA), have been used in attempts to deliver peptides to the cell cytosol as internal or amino-terminal fusions (Arora et al. (1993) *J. Biol. Chem.* 268:3334 3341; Perelle et al. (1993) *Infect. Immun.* 61:5147 5156 (1993); Stenmark et al. (1991) *J. Cell Biol.* 113:1025 1032 (1991); Donnelly et al. (1993) *Proc. Natl. Acad. Sci. USA* 90:3530 3534; Carbonetti et al. (1995) *Abstr. Annu. Meet. Am. Soc. Microbiol.* 95:295; Sebo et al. (1995) *Infect. Immun.* 63:3851 3857; Klimpel et al. (1992) *Proc. Natl. Acad. Sci. USA* 89:10277 10281; and Novak et al. (1992) *J. Biol. Chem.* 267:17186 17193).

Effectors can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, in this case an effector. The liposome fuses with the plasma membrane, thereby releasing the effector into the cytosol. Alternatively, the liposome is phagocytosed or taken up by the cell in a transport vesicle. Once in the endosome or phagosome, the liposome either degrades or fuses with the membrane of the transport vesicle and releases its contents.

The invention particularly relates to the field of plant and agricultural technology. In one aspect, the present invention is directed to a method to modulate the expression of a target gene in plant cells, which method comprises providing plant cells with a polypeptide modified according to the invention, said polypeptide being capable of specifically recognizing a target nucleotide sequence, or a complementary strand thereof, within a target gene, and allowing said polypeptide to recognize and particularly bind to said target nucleotide sequence, whereby the expression of said target gene in said plant cells is modulated.

The polypeptide can be provided to the plant cells via any suitable methods known in the art. For example, the protein can be exogenously added to the plant cells and the plant cells are maintained under conditions such that the polypeptide is introduced into the plant cell, binds to the target nucleotide sequence and regulates the expression of the target gene in the plant cells. Alternatively, a nucleotide sequence, e.g., DNA or RNA, encoding the polypeptide can be expressed in the plant cells and the plant cells are maintained under conditions such that the expressed polypeptide binds to the target nucleotide sequence and regulates the expression of the target gene in the plant cells.

A preferred method to modulate the expression of a target gene in plant cells comprises the following steps: a) providing plant cells with an expression system for a polypeptide modified according to the invention, said polypeptide being capable of specifically recognizing, and preferably binding, to a target nucleotide sequence, or a complementary strand thereof, within an expression control element of a target gene, preferably a promoter; and b) culturing said plant cells under conditions wherein said polypeptide is produced and binds to said target nucleotide sequence, whereby expression of said target gene in said plant cells is modulated.

Any target nucleotide sequence can be modulated by the present method. For example, the target nucleotide sequence can be endogenous or exogenous to the target gene. In an embodiment of the invention the target nucleotide sequence can be present in a living cell or present in vitro. In a specific embodiment, the target nucleotide sequence is endogenous to the plant. The target nucleotide sequence can be located in any suitable place in relation to the target gene. For example, the target nucleotide sequence can be upstream or downstream of the coding region of the target gene. Alternatively, the target nucleotide sequence is within the coding region of the target gene. Preferably, the target nucleotide sequence is a promoter of a gene.

Any target gene can be modulated by the present method. For example, the target gene can encode a product that affects biosynthesis, modification, cellular trafficking, metabolism and degradation of a peptide, a protein, an oligonucleotide, a nucleic acid, a vitamin, an oligosaccharide, a carbohydrate, a lipid, or a small molecule. Furthermore, effectors can be used to engineer plants for traits such as increased disease resistance, modification of structural and storage polysaccharides, flavors, proteins, and fatty acids, fruit ripening, yield, color, nutritional characteristics, improved storage capability, and the like.

Therefore, the invention provides a method of altering the expression of a gene of interest in a target cell, comprising : determining (if necessary) at least part of the DNA sequence of the structural region and/or a regulatory region of the gene of interest; designing a polypeptide including the repeat units modified in accordance with the invention to recognize specific base pairs on the DNA of known sequence, and causing said modified polypeptide to be present in the target cell, (preferably in the nucleus thereof). (It will be apparent that the DNA sequence need not be determined if it is already known.)

The regulatory region could be quite remote from the structural region of the gene of interest (e.g. a distant enhancer sequence or similar).

In addition, the polypeptide may advantageously comprise functional domains from other proteins (e.g. catalytic domains from restriction endonucleases, recombinases, replicases, integrases and the like) or even "synthetic" effector domains. The polypeptide may also comprise activation or processing signals, such as nuclear localisation signals. These are of particular usefulness in targeting the polypeptide to the nucleus of the cell in order to enhance the binding of the polypeptide to an intranuclear target (such as genomic DNA).

The modified polypeptide may be synthesised in situ in the cell as a result of delivery to the cell of DNA directing expression of the polypeptide. Methods of facilitating delivery of DNA are well-known to those skilled in the art and include, for example, recombinant viral vectors (e.g. retroviruses, adenoviruses), liposomes and the like. Alternatively, the modified polypeptide could be made outside the cell and then delivered thereto. Delivery could be facilitated by incorporating the polypeptide into liposomes etc. or by attaching the polypeptide to a targeting moiety (such as the binding portion of an antibody or hormone molecule, or a membrane transition domain, or the translocation domain of a fungal or oomycete effector, or the cell-binding B-domain of the classical A-B family of bacterial toxins). Indeed, one significant advantage of the modified proteins of the invention in controlling gene expression would be the vector-free delivery of protein to target cells.

To the best knowledge of the inventors, design of a polypeptide containing modified repeat units capable of specifically recognizing base pairs in a target DNA sequence and its successful use in modulation of gene expression (as described herein) has never previously been demonstrated. Thus, the breakthrough of the present invention as disclosed herein presents numerous possibilities that extend beyond uses in plants. In one embodiment of the invention, effector polypeptides are designed for therapeutic and/or prophylactic use in regulating the expression of disease-associated genes. For example, said polypeptides could be used to inhibit the expression of foreign genes (e.g., the genes of bacterial or viral pathogens) in humans, other animals, or plants, or to modify the expression of mutated host genes (such as oncogenes).

The invention therefore also provides an effector polypeptide capable of inhibiting the expression of a disease-associated gene. Typically the polypeptide will not be a naturally occurring polypeptide but will be specifically designed to inhibit the expression of the disease-associated gene. Conveniently the effector polypeptide will be designed by any of the methods of the invention.

The invention also relates to the field of genome engineering. An effector polypeptide can be generated according to the invention to target a specific DNA sequence in a genome. Said polypeptide can be modified to contain an activity that directs modification of the target DNA sequence (e.g. site specific recombination or integration of target sequences). This method enables targeted DNA modifications in complex genomes.

In a still further embodiment of the invention, a polypeptide is provided which is modified to include at least a repeat domain comprising repeat units, the repeat units having hypervariable region for determining selective recognition of a base pair in a DNA sequence.

In a preferred embodiment, the polypeptide comprises within said repeat unit a hypervariable region which is selected from the following group in order to determine recognition of one of the following base pairs:

HD for recognition of C/G
NI for recognition of A/T
NG for recognition of T/A
NS for recognition of C/G or A/T or T/A or G/C
NN for recognition of G/C or A/T
IG for recognition of T/A
N for recognition of C/G or T/A
HG for recognition of T/A
H for recognition of T/A
NK for recognition of G/C
NH for recognition of G/C
NP for recognition of A/T or C/G or T/A
NT for recognition of A/T or G/C
HN for recognition of A/T or G/C
SH for recognition of G/C
SN for recognition of G/C and
IS for recognition of A/T.

The polypeptides of the present invention can further comprise within a repeat unit a hypervariable region which is selected from the following group in order to determine recognition of one of the following base pairs: HA for recognition of C/G; ND for recognition of C/G; HI for recognition of C/G; HN for recognition of G/C; and NA for recognition of G/C.

The invention also comprises DNA which encodes for any one of the polypeptides described before.

In a still further embodiment, DNA is provided which is modified to include a base pair located in a target DNA sequence so that said base pair can be specifically recognized by a polypeptide which includes at least a repeat domain comprising repeat units, the repeat units having a hypervariable region which determine recognition of said base pair in said DNA. In one optional embodiment, said base pair is located in a gene expression control sequence. Due to the modular assembly of the repeat domain, a sequence of base pairs can be specifically targeted by said repeat domain.

In an alternative embodiment of the invention, said DNA is modified by a base pair selected from the following group in order to receive a selective and determined recognition by one of the following hypervariable regions:

C/G for recognition by HD
A/T for recognition by NI
T/A for recognition by NG
CT or A/T or T/A or G/C for recognition by NS
G/C or A/T for recognition by NN
T/A for recognition by IG.
C/G or T/A for recognition by N
T/A for recognition by HG
T/A for recognition by H
G/C for recognition by NK
G/C for recognition of NH
A/T or C/G or T/A for recognition of NP
A/T or G/C for recognition of NT
A/T or G/C for recognition of HN
G/C for recognition of SH
G/C for recognition of SN and
A/T for recognition of IS.

The DNA of the present invention can be modified to modified by a base pair selected from the following group in order to receive a selective and determined recognition by one of the following hypervariable regions: HA for recognition of C/G; ND for recognition of C/G; HI for recognition of C/G; HN for recognition of G/C; and NA for recognition of G/C.

In yet another aspect the invention provides a method of modifying a nucleic acid sequence of interest present in a sample mixture by binding thereto a polypeptide according to the invention, comprising contacting the sample mixture with said polypeptide having affinity for at least a portion of the sequence of interest, so as to allow the polypeptide to recognize and preferably bind specifically to the sequence of interest.

The term "modifying" as used herein is intended to mean that the sequence is considered modified simply by the binding of the polypeptide. It is not intended to suggest that the sequence of nucleotides is changed, although such changes (and others) could ensue following binding of the polypeptide to the nucleic acid of interest. Conveniently the nucleic acid sequence is DNA.

Modification of the nucleic acid of interest (in the sense of binding thereto by a polypeptide modified to contain modular repeat units) could be detected in any of a number of methods (e.g. gel mobility shift assays, use of labelled polypeptides - labels could include radioactive, fluorescent, enzyme or biotin/streptavidin labels).

Modification of the nucleic acid sequence of interest (and detection thereof) may be all that is required (e.g. in diagnosis of disease). Desirably, however, further processing of the sample is performed. Conveniently the polypeptide (and nucleic acid sequences specifically bound thereto) is separated from the rest of the sample. Advantageously the polypeptide-DNA complex is bound to a solid phase support, to facilitate such separation. For example, the polypeptide may be present in an acrylamide or agarose gel matrix or, more preferably, is immobilised on the surface of a membrane or in the wells of a microtitre plate.

In one embodiment of the invention, said repeat domain comprising repeat units is inserted in a bacterial, viral, fungal, oomycete, human, animal or plant polypeptide to achieve a targeted recognition and preferably binding of one or more specified base pairs in a DNA sequence, and optionally wherein said repeat units are taken from the repeat domains of AvrBs3-like family of proteins which are further optionally modified in order to obtain a pre-selected specific binding activity to one or more base pairs in a DNA sequence.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed DNA sequences and proteins encoded thereby are also encompassed by the present invention. By "fragment" is intended a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the invention.

"Variants" is intended to mean substantially similar sequences. For DNA sequences, a variant comprises a DNA sequence having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" DNA sequence or polypeptide comprises a naturally occurring DNA sequence or amino acid sequence, respectively. For DNA sequences, conservative variants include those sequences that, because of the degeneracy of the genetic code, encode the amino acid sequence of one of the polypeptides of the invention. Variant DNA sequences also include synthetically derived DNA sequences, such as those generated, for example, by using site-directed mutagenesis but which still encode a protein of the invention. Generally, variants of a particular DNA sequence of the invention will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular DNA sequence of the invention (i.e., the reference DNA sequence) can also be evaluated by comparison of the percent sequence identity between the polypeptide encoded by a variant DNA sequence and the polypeptide encoded by the reference DNA sequence. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein as described herein. Such variants may result from, for example, genetic polymorphism or from human manipulation. Biologically active variants of a protein of the invention will have at least about 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays as described elsewhere herein or known in the art.

Variant DNA sequences and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

In a PCR approaches, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the DNA sequences and proteins of the invention encompass polynucleotide molecules and proteins comprising a nucleotide or an amino acid sequence that is sufficiently identical to the DNA sequences or to the amino acid sequence disclosed herein. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 70% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website: http://www.ebj.ac.uk/Tools/clustalw/index.html).

The DNA sequences of the invention can be provided in expression cassettes for expression in any prokaryotic or eukaryotic cell and/or organism of interest including, but not limited to, bacteria, fungi, algae, plants, and animals. The cassette will include 5' and 3' regulatory sequences operably linked to a DNA sequence of the invention. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the DNA sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a DNA sequence of the invention, and a transcriptional and translational termination region (i.e., termination region) functional in plants or other organism or non-human host cell. The regulatory regions (i.e., promoters, transcriptional regulatory regions, and translational termination regions) and/or the DNA sequence of the invention may be native/analogous to the host cell or to each other. Alternatively, the regulatory regions and/or DNA sequence of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked DNA sequence of interest, may be native with the host, or may be derived from another source (i.e., foreign or heterologous) to the promoter, the DNA sequence of interest, the plant host, or any combination thereof. Convenient termination regions for use in plants are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in a transformed organism. That is, the polynucleotides can be synthesized using codons preferred by the host for improved expression. See, for example, Campbell and Gowri (1990) *Plant Physiol.* 92:1-11 for a discussion of host-preferred codon usage. Methods are available in the art for synthesizing host-preferred gene, particularly plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the host of interest and the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 1 3:2723-2730); ALS promoter (U.S. Pat. No. 5,659,026), and the like.

Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular host tissue. Such tissue-preferred promoters for use in plants include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 1 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol. 78* (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.*76:767-774; Hinchee, et al. (1990) *Stadler. Genet. Symp.*203212.203-212; Cousins, et al. (1991) *Aust. J. Plant Physiol.* 18:481-494; Chee, P. P. and Slightom, J. L. (1992) *Gene.*118:255-260; Christou, et al. (1992) *Trends. Biotechnol.* 10:239-246; D'Halluin, et al. (1992) Bio/Technol. 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct comprising a DNA sequence into a host cell. By "introducing" is intended presenting to the plant the polynucleotide construct in such a manner that the construct gains access to the interior of the host cell. The methods of the invention do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

By "stable transformation" is intended that the polynucleotide construct introduced into a plant integrates into the genome of the host and is capable of being inherited by progeny thereof. By "transient transformation" is intended that a polynucleotide construct introduced into the host does not integrate into the genome of the host.

For the transformation of plants and plant cells, the DNA sequences of the invention are inserted using standard techniques into any vector known in the art that is suitable for expression of the DNA sequences in a host cell or organism of interest. The selection of the vector depends on the preferred transformation technique and the target host species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant*

Science 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

The DNA sequences of the invention may be introduced into plants by contacting plants with a virus or viral nucleic acids. Generally, such methods involve incorporating a polynucleotide construct of the invention within a viral DNA or RNA molecule. It is recognized that the a protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In specific embodiments, the DNA sequences of the invention can be provided to a plant using a variety of transient transformation methods. Such transient transformation methods include, but are not limited to, the introduction of the protein or variants and fragments thereof directly into the plant or the introduction of a transcript encoding the protein into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the polynucleotide can be transiently transformed into the plant using techniques known in the art. Such techniques include *Agrobacterium tumefaciens*-mediated transient expression as described below.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Plants of particular interest include, but are not limited to, and grain plants that provide seeds of interest, oil-seed plants, leguminous plants, and *Arabidopsis thaliana*. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides.

The present invention further encompasses the introduction of the DNA sequences of the invention into non-plant host cells, including, but not limited to, bacterial cells, yeast cells other fungal cells, human cells, and other animal cells. In addition, the invention encompasses the introduction of the DNA sequences into animals and other organisms by both stable and transient transformation methods.

As discussed herein, a DNA sequence of the present invention can be expressed in these eukaryotic systems. Synthesis of heterologous polynucleotides in yeast is well known (Sherman et al. (1982) Methods in Yeast Genetics, Cold Spring Harbor Laboratory). Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The sequences of the present invention can also be ligated to various expression vectors for use in transfecting cell cultures of mammalian or insect origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) Immunol. Rev. 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider (1987) J. Embyol. Exp. Morphol. 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP 1 intron from SV40 (Sprague et al. (1983) *J. Virol.* 45:773-781).

Additionally, gene sequences to control replication in the host cell may be incorporated into the vector such as those found in bovine papilloma virus type-vectors (Saveria-Campo (1985) DNA Cloning Vol. II a Practical Approach, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) Biochemical Methods in Cell Culture and Virology, Dowden, Hutchinson and Ross, Inc.).

Prokaryotes most frequently are represented by various strains of *E. coli*; however, other microbial strains may also be used in the method of the invention. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) Nature 292: 128). The inclusion of selection markers in DNA vectors transfected in E coli. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235); Mosbach et al. (1983) *Nature* 302:543-545).

With respect to fusion proteins, "operably linked" is intended to mean a functional linkage between two or more elements or domains. If it recognized that a linker of one or more amino acids may be inserted in between each of the two or more elements to maintain the desired function of the two or more elements.

In one embodiment of the invention, fusion proteins comprise a repeat domain of the invention operably linked to at least one protein or part or domain thereof. In certain embodiments of the invention, the protein or part or domain thereof comprises a protein or functional part or domain thereof, that is capable of modifying DNA or RNA. In other embodiments, protein or functional part or domain thereof is capable of functioning as a transcriptional activator or a transcriptional repressor. Preferred proteins include, but are not limited to, transcription activators, a transcription repressors, a resistance-mediating proteins, nucleases, topoisomerases, ligases, integrases, recombinases, resolvases, methylases, acetylases, demethylases, and deacetylases.

The following examples are offered by way of illustration and not by way of limitation.

EXAMPLES

Example 1

Identification of the Basis for DNA Specificity of TAL Effectors

The fact that AvrBs3 directly binds the UPA-box, a promoter element in induced target genes (Kay et al. (2007) *Science* 318, 648-651; Omer et al. (2007) Science 318:645-648), prompted us to investigate the basis for DNA-sequence specificity. Each repeat region generally consists of 34 amino acid, and the repeat units are nearly identical; however, amino acids 12 and 13 are hypervariable (Schornack et al. (2006) *J. Plant Physiol.* 163:256-272; FIG. 1A). The most C-terminal repeat of AvrBs3 shows sequence similarity to other repeat units only in its first 20 amino acids and is therefore referred to as half repeat. The repeat units can be classified into different repeat types based on their hypervariable 12th and 13th amino acids (FIG. 1B). Because the size of the UPA-box (18 (20)/19 (21) bp) almost corresponds to the number of repeat units (17.5) in AvrBs3, we considered the possibility that one repeat unit of AvrBs3 contacts one specific DNA base pair. When the repeat types of AvrBs3 (amino acid 12 and 13 of each repeat) are projected onto the UPA box, it becomes evident that certain repeat types correlate with specific base pairs in the target DNA. For example, HD and NI repeat units have a strong preference for C and A, respectively (FIG. 1B). For simplicity, we designate only bases in the upper (sense) DNA strand. Our model of recognition specificity is supported by the fact that the AvrBs3 repeat deletion derivative AvrBs3Δrep16 which lacks four repeat units (Δ11-14; FIG. 5A, B) recognizes a shorter and different target DNA sequence (FIGS. 5 to 8). Based on sequence comparisons of UPA-boxes of AvrBs3-induced pepper genes and mutational analysis, the target DNA box of AvrBs3 appears to be 1 bp longer than the number of repeat units in AvrBs3. In addition, a T is conserved at the 5' end of the UPA box immediately preceding the predicted recognition specificity of the first repeat (FIG. 1). Intriguingly, secondary structure predictions of the protein region preceding the first repeat and the repeat region show similarities, despite lack of amino acid-sequence conservation. This suggests an additional repeat, termed repeat 0 (FIG. 1B).

To further substantiate and extend our model (FIG. 1B), we predicted the yet unknown target DNA sequences of *Xanthomonas* TAL effectors based on the sequence of their repeat units, and inspected the promoters of known TAL target genes and their alleles for the presence of putative binding sites. We identified sequences matching the predicted specificity in promoters of alleles that are induced in response to the corresponding TAL effector, but not in non-induced alleles (FIG. 5C-F). The presence of these boxes suggests that the induced genes are direct targets of the corresponding TAL effectors. Based on the DNA base frequency for different repeat types in the target DNA sequences using eight TAL effectors we deduced a code for the DNA target specificity of certain repeat types (FIG. 1C, D; FIG. 5).

Figure 3A:
FIGS. 3A-3E. DNA Base Pair Recognition Specificities of Repeat Types.
Figure 3B:
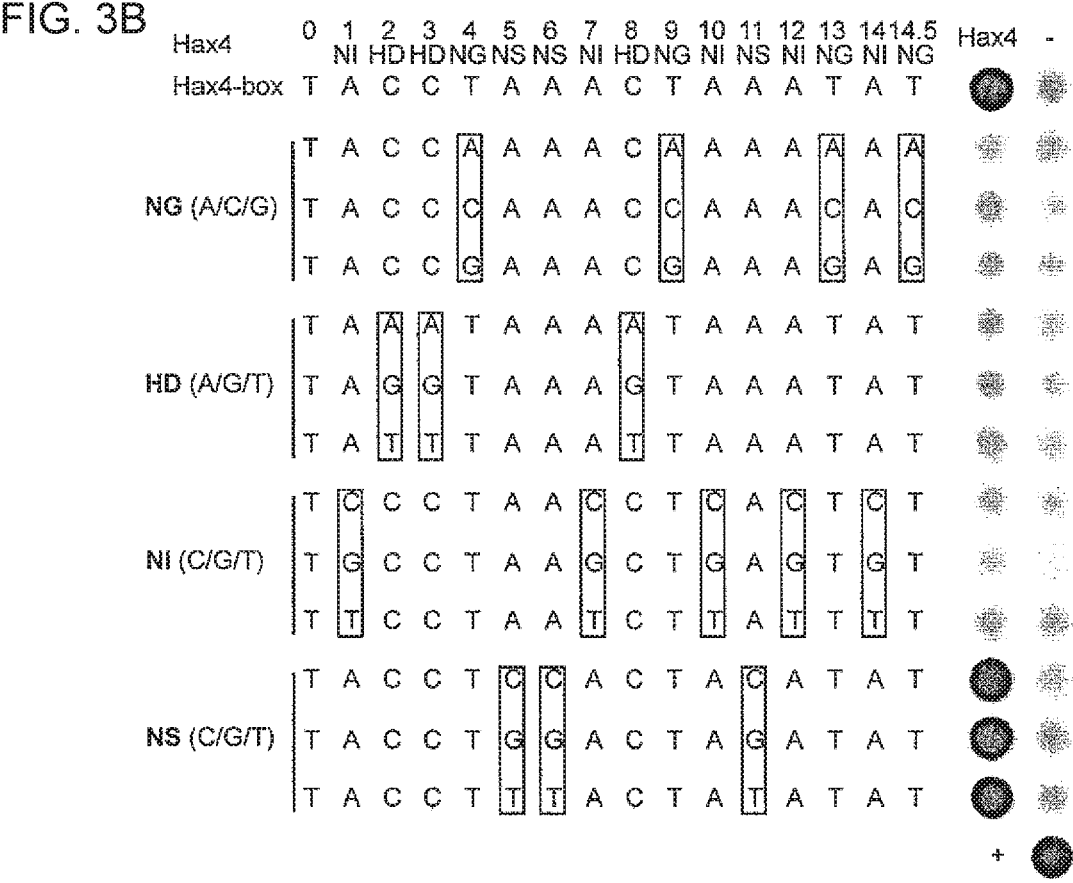
Figure 3C:
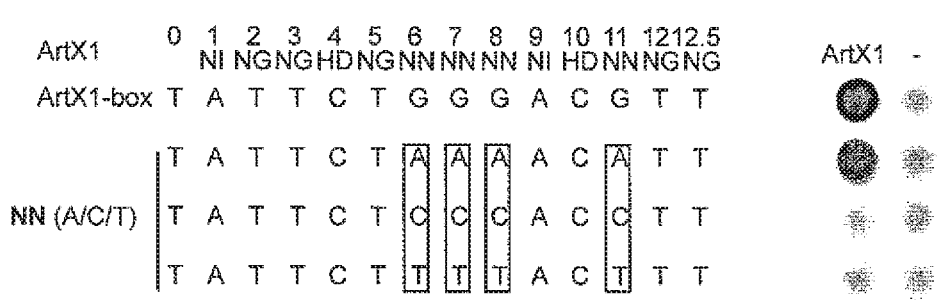
Figure 3D:
Figure 3E:
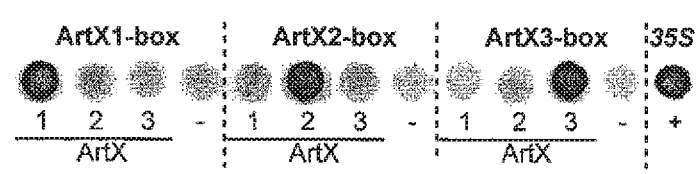

To experimentally validate our model we predicted target DNA sequences for the TAL effectors Hax2 (21.5 repeat units), Hax3 (11.5 repeat units), and Hax4 (14.5 repeat units) from the *Brassicaceae*-pathogen *X. campestris* pv. *armoraciae* (22). First, we derived target DNA boxes for Hax3 and Hax4, because they exclusively contain repeat-types present in AvrBs3 (amino acid 12/13: NI, HD, NG, NS; FIG. 1A, FIG. 2A) for which DNA binding and gene activation have been shown experimentally. The Hax3 and Hax4 target boxes were placed in front of the minimal (−55 to +25) tomato Bs4 promoter, which has very weak basal activity (Schornack et al. (2005) *Mol. Plant-Microbe Interact.* 18:1215-1225; FIG. 2B; FIG. 9), driving a promoterless uidA (β-glucuronidase, GUS) reporter gene. For transient expression studies, we transfected the reporter constructs together with cauliflower mosaic virus 35S-promoter driven effector genes hax3 and hax4 into *Nicotiana benthamiana* leaves using *Agrobacterium*-mediated T-DNA delivery. Qualitative and quantitative GUS assays demonstrated that promoters containing the Hax3- or Hax4-box were strongly and specifically induced in the presence of the corresponding effector (FIG. 2C). Likewise, we addressed the importance of the first nucleotide (T) in the predicted target DNA sequence of Hax3 and generated four different Hax3-boxes with either A, C, G or T at the 5' end (FIG. 10A, B). Coexpression of hax3 and the reporter constructs in *N. benthamiana* demonstrated that only a promoter containing a Hax3-box with a 5' T was strongly induced in the presence of Hax3 whereas the others led to weaker activation (FIG. 10C). This indicates that position 0 contributes to promoter activation specificity of Hax3 and likely other TAL effectors. To address the possibility that some repeat types confer broader specificity, i.e., recognize more than one base, we permutated the Hax4-box (FIG. 3A, B). Transient GUS assays showed that NI-, HD-, and NG-repeat units in Hax4 strongly favour recognition of the bases A, C, and T, respectively, whereas NS-repeat units recognize all four bases (FIG. 3B; FIG. 11). As several TAL effectors contain NN-repeat units (FIG. 5 and FIG. 15, Table 1), we generated ArtX1, an artificial TAL effector with NN-repeat units and deduced a corresponding DNA recognition sequence using our code (FIG. 3C). Analysis of ArtX1-box derivatives demonstrated that NN-repeat units recognize both A and G, with preference for G (FIG. 3C). This result confirms our prediction of the natural AvrXa27-box in rice which contains either an A or a G at positions corresponding to NN-repeat units (FIG. 5C). In addition, we derived two possible AvrXa10-boxes with either A or G at positions corresponding to NN-repeat units in AvrXa10. Both reporter constructs were induced efficiently by AvrXa10 (FIG. 12). Together, these data strongly suggest that some repeat types recognize specific base pairs whereas others are more flexible.

An exceptional TAL effector is Hax2 because it contains 35 amino acids per repeat instead of the typical 34 amino acid-repeat units (Kay et al. (2005) *Mol. Plant-Microbe Interact.* 18:838-848). In addition, Hax2 contains a rare amino acid combination in its second repeat (amino acids 12/13: IG; FIG. 2A). We permutated the corresponding third base of the Hax2-box and analyzed reporter gene activation with the effector Hax2 using the transient assay. This showed that an IG repeat confers specificity for T (FIG. 13). The Hax2-box only leads to promoter activation by Hax2, but not by Hax3 or Hax4 (FIG. 2C). This demonstrates that 35 amino acid-repeat units function like 34 amino acid-repeat units. This is supported by the fact that the TAL effector AvrHah1 which contains 35 amino acid repeat units, induces Bs3-mediated resistance (Schornack et al. (2008) *New Phytol.* 179:546-556). The repeat types of AvrHah1 match to the UPA-box in the Bs3 promoter (FIG. 5A, B).

Interestingly, the expression of hax2 in *Arabidopsis thaliana* leads to purple coloured leaves, indicating an accumulation of anthocyanin (FIG. 14A, B). To identify Hax2 target genes we analyzed promoter regions of the A. thaliana genome using pattern search (Patmatch, TAIR; www.arabidopsis.org) with degenerated Hax2-box sequences. One of the putative Hax2 target genes encodes the MYB transcription factor PAP1 (At1G56650) which controls anthocyanin biosynthesis (Borevitz et al. (2000) *Plant Cell* 12:2383-2394). Semiquantitative analysis of the PAP1 transcript level demonstrated that expression of PAP1 is strongly induced by Hax2 (FIG. 14C). Visual inspection of the PAP1 promoter region revealed the presence of a suboptimal Hax2-box (FIG. 14D, E). Based on the code for TAL effector repeat types (FIG. 1D) and the data described above we predicted putative target DNA sequences for additional TAL effectors some of which are important virulence factors (FIG. 15, Table 1).

Because the repeat number in TAL effectors ranges from 1.5 to 28.5, a key question is whether effectors with few repeat units can activate gene expression. Therefore, we tested how the number of repeat units influences target gene expression. For this, we constructed artificial effectors containing the N- and C-terminal regions of Hax3 and a repeat domain with 0.5 to 15.5 HD-repeat units (specificity for C). For technical reasons, the first repeat in all cases was NI (specificity for A). The corresponding target DNA box consists of 17 C-residues preceded by TA (FIG. 4A, B). Promoter activation by the artificial effectors was measured using the transient Bs4-promoter GUS-assay in *N. benthamiana*. While at least 6.5 repeat units were needed for gene induction, 10.5 or more repeat units led to strong reporter gene activation (FIG. 4C). These data demonstrate that a minimal number of repeat units is required to recognize the artificial target DNA-box and activate gene expression. The results also suggest that effectors with fewer repeat numbers are largely inactive. We have shown that the repeat region of TAL effectors has a sequential nature that corresponds to a consecutive target DNA sequence. Hence, it should be feasible to generate effectors with novel DNA-binding specificities. Three artificial effectors were generated (ArtX1, ArtX2, ArtX3), each with randomly assembled 12.5 repeat units (FIG. 3C, D), and tested for induction of Bs4 promoter-reporter fusions containing predicted target DNA-sequences. All three artificial effectors strongly and specifically induced the GUS reporter only in presence of the corresponding target DNA-box (FIG. 3E; FIG. 11). Our model for recognition specificity of TAL effectors in which one repeat unit contacts one base pair in the DNA via amino acids 12 and 13 of each repeat enables to predict the binding specificity of TAL effectors and identification of plant target genes. As many TAL effectors are major virulence factors the knowledge of plant target genes will greatly enhance our understanding of plant disease development caused by xanthomonads. In addition, we successfully designed artificial effectors that act as transcription factors with specific DNA-binding domains. Previously, zinc finger transcription factors containing a tandem arrangement of zinc finger units have been engineered to bind specific target DNA sequences.

Similarly, TAL effectors have a linear DNA-binding specificity that can easily be rearranged. It has not escaped our notice that the postulated right-handed superhelical structure of the repeat regions in TAL effectors immediately suggests a possible mechanism for interaction with the right-handed helix of the genetic material. It will be important to determine the structure of the novel DNA-binding domain of TAL effectors complexed with target DNA.

The following paragraphs describe further embodiments of the invention:

1) Prediction of DNA-Binding Specificities of Naturally Occuring AvrBs3-homologous Proteins and Generation of Resistant Plants.

The repeat units of the repeat domain of naturally occurring effectors of the AvrBs3-family encode a corresponding DNA-binding specificity. These recognition sequences can be predicted with the recognition code.

The artificial insertion of the predicted recognition sequences in front of a gene in transgenic plants leads to expression of the gene if the corresponding AvrBs3-like effector is translocated into the plant cell (e.g. during a bacterial infection).

If the recognition sequence is inserted in front of a gene whose expression leads to a defence reaction (resistance-mediating gene) of the plant, such constructed transgenic plants are resistant against an infection of plant pathogenic bacteria which translocate the corresponding effector.

2) The Identification of Plant Genes whose Expression is Induced by a Specific Effector of the AvrBs3-Family The prediction of DNA target sequences of a corresponding effector of the AvrBs3-family in the promoter region of plant genes is an indication for the inducible expression of these genes by the effector. Using the method according to the invention it is possible to predict inducible plant genes. Predictions are particularly straightforward in sequenced genomes.

3) Use of Other Effectors as Transcriptional Activators in Expression Systems

Analogous to the use of Hax3 and Hax4, the predicted DNA binding sequences of other members of the AvrBs3-family can be inserted into promoters to generate new controllable promoters which can be induced by the corresponding effector.

4) Construction of a Secondarily Inducible System

Two constructs are introduced into plants. First, a hax3 gene whose expression is under control of an inducible promoter. Secondly, a target gene that contains the Hax3-box in the promoter. Induction of the expression of hax3 leads to production of the Hax3 protein that then induces the expression of the target gene. The described two-component construction leads to a twofold expression switch which allows a variable expression of the target gene. The transactivator and the target gene can also be present first in different plant lines and can be introgressed at will. Analogous to this, Hax4 and the corresponding Hax4-box can be used. This system can also be used with other members of the AvrBs3-family or artificial derivatives and predicted DNA-target sequences. The functionality of the system could already be verified. Transgenic *Arabidopsis thaliana* plants were constructed, which contain an inducible avrBs3 gene as well as a Bs3 gene under control of its native promoter, whose expression can be induced by AvrBs3. The induction of expression of avrBs3 leads to expression of Bs3 and therefore to cell death. See, WO 2009/042753, herein incorporated by reference.

5) Construction of Disease-resistant Plants

If the DNA target sequence of an AvrBs3-similar effector is inserted in front of a gene whose expression leads to a defence reaction (resistance-mediating gene) of the plant, correspondingly constructed transgenic plants will be resistant against infection of plant pathogenic organisms, which make this effector available. Such a resistance-mediating gene can for example lead to a local cell death which prevents spreading of the organisms/pathogens, or induce the basal or systemic resistance of the plant cell.

6) Generation of Repeat Domains for the Detection of a Specific DNA Sequence and Induction of Transcription of the Following Genes The modular architecture of the central repeat domain enables the targeted construction of definite DNA binding specificities and with this the induction of transcription of selected plant genes. The DNA binding specificities can either be artificially inserted in front of target genes so that novel effector-DNA-box variants are generated for the inducible expression of target genes. Moreover, repeat domains can be constructed that recognize a naturally occurring DNA sequence in organisms. The advantage of this approach is that the expression of any gene in non-transgenic organisms can be induced if a corresponding effector of the invention is present in the cells of this organism.

Introduction of the effector can be done in different ways:

(1) transfer via bacteria with a protein transport system (e.g. type-III secretion system);

(2) cell-bombardment with an artificial AvrBs3-protein;

(3) transfer of a DNA-segment that leads to production of the effector, via introgression, *Agrobacterium*, viral vectors or cell-bombardment; or (4) other methods that result in uptake of the effector protein by the target cell The central repeat domain of effectors of the AvrBs3-family is a new type of DNA binding domain (Kay et al., 2007). The decryption of the specificity of the single repeat units now allows the targeted adaptation of the DNA-binding specificity of this region. The DNA binding region can be translationally fused to other functional domains to generate sequence-specific effects. Below, four examples of such protein fusions are given.

7) Construction of Transcriptional Activators for the Inducible Expression of Genes in Cells of Living Organisms The effectors of the AvrBs3-like family induce the expression of genes in plant cells. For this, the C-terminus of the protein is essential, which contains a transcriptional activation domain and nuclear localization sequences that mediate the import of the protein into the plant nucleus. The C-terminus of the AvrBs3-homologous protein can be modified in such a way that it mediates the expression of genes in fungal, animal, or human systems. Thereby, effectors can constructed that function as transcriptional activators in humans, other animals, or fungi. Thus, the methods according to the invention can be applied not only to plants, but also to other living organisms.

8) Use of Effectors as Transcriptional Repressors

The DNA binding specificity of the repeat domain can be used together with other domains in protein fusions to construct effectors that act as specific repressors. These effectors exhibit a DNA binding specificity that has been generated in such a way that they bind to promoters of target genes. In contrast to the TAL effectors which are transcription activators, these effectors are constructed to block the expression of target genes. Like classical repressors, these effectors are expected to cover promoter sequences by their recognition of, or binding to, a target DNA sequence and make them inaccessible for factors that otherwise control the expression of the target genes. Alternatively, or in addition, the repeat domains can be fused to a transcription-repressing domain, such as an EAR motif (Ohta et al. *Plant Cell* 13:1959-1968 (2001)).

9) Use of Repeat Domains for Labelling and Isolation of Specific Sequences

The capability of a repeat domain to recognize a specific target DNA sequence can be used together with other domains to label specific DNA sequences. C-terminally a GFP ("green-fluorescent-protein") can for example be fused to an artificial repeat domain that detects a desired DNA sequence. This fusion protein binds in vivo and in vitro to a corresponding DNA sequence. The position of this sequence on the chromosome can be localized using the fused GFP-protein. In an analogous way, other protein domains that enable a cellular localization of the protein (e.g. by FISH) can be fused to a specific artificial repeat domain which targets the protein to a corresponding DNA sequence in the genome of the cell. In addition, the DNA recognition specificity of repeat domains of the invention can be used to isolate specific DNA sequences. For this, the AvrBs3-like protein can be immobilized to a matrix and interacts with corresponding DNA molecules that contain a matching sequence. Therefore, specific DNA sequences can be isolated from a mixture of DNA molecules.

10) Use of Repeat Domains for the Endonucleolytic Cleavage of DNA

The DNA recognition specificity of the repeat domain can be fused to a suitable restriction endonuclease to specifically cleave DNA. Therefore, the sequence-specific binding of the repeat domain leads to localization of the fusion protein to few specific sequences, so that the endonuclease specifically cleaves the DNA at the desired location. By means of the recognition of target DNA sequences, unspecific nucleases such as FokI can be changed into specific endonucleases analogous to work done with zinc finger nucleases. For example, the optimal distance between the two effector DNA target sites would be determined to that would be required to support dimerization of two FokI domains. This would be accomplished by analysis of a collection of constructs in which the two DNA binding sites are separated by differently sized spacer sequences. Using this approach enables one to determine the distances that allow nuclease-mediated DNA cleavage to occur and the functional analysis of additional effector nucleases that target different DNA sequences. In an alternative approach, a newly developed single-chain FokI dimer (Mino et al. (2009) *J. Biotechnol* 140:156-161) is employed. In this approach two FokI catalytic domains are transcriptionally fused to a single repeat domain of the invention. Thus, functionality of a corresponding nuclease no longer relies on intermolecular dimerization of two FokI domains that are located on two different proteins. This type of construct has been used successfully in the context of zinc finger-based DNA binding motifs. Moreover, these methods enable very specific cuts at only a few positions in complex DNA-molecules. These methods can amongst other things be used to introduce double-strand breaks in vivo and selectively incorporate donor DNA at these positions. These methods can also be used to specifically insert transgenes.

11) Construction of Repeat Domains with Custom-designed Repeat Order

Due to the high similarity between the individual repeat units of a repeat domain, construction of a custom DNA-binding polypeptide as described above might not be feasible through methods involving traditional cloning methods. As detailed in this example, a repeat domain with a repeat unit order that matches a desired DNA-sequence in a promoter of interest, such as the Bs4 promoter (FIG. 17B, C), is determined based on the recognition code of the present invention. Generation of a specific 11.5 repeat unit order was accomplished using "Golden gate" cloning (Engler et al. (2008) *PLoS ONE* 3:e3647). As building blocks, we subcloned the N- and C-terminus of Hax3 as well as the 12 individual repeat units resembling the 11.5 repeat units. Each building block contained individual flanking BsaI sites (FIG. 18) that allowed an ordered assembly of the fragments into a custom effector polypeptide. The effector (ARTBs4) was correctly assembled from the total of 14 fragments into a BsaI-compatible binary vector that allows *Agrobacterium*-mediated expression of the custom effector polypeptide as an N-terminally tagged GFP fusion in plant cells (FIG. 18).

12) Use of Effectors as Viral Repressors

The nucleotide binding specificity of the repeat domain can be used to design effectors that disrupt viral replication in cells. These effectors will exhibit a nucleotide binding specificity targeted to nucleotide sequence in viral origins of replication and other sequences critical to viral function. No additional protein domains need to be fused to these repeat domain proteins in order to block viral function. They act like classical repressors by covering origins of replication or other key sequences, including promoters, enhancers, long terminal repeat units, and internal ribosome entry sites, by binding and making them inaccessible for host or viral factors, including viral encoded RNA-dependent RNA polymerase, nucleocapsid proteins and integrases, which participate in viral replication and function. This type of strategy has been used successfully with zinc-finger proteins (Sera (2005) *J. Vir.* 79:2614-2619; Takenaka et al. (2007) *Nucl Acids Symposium Series* 51:429-430).

Summarizing, the present invention additionally covers isolated nucleic acid molecules to be used in any of the methods of the present invention, transformed plants comprising a heterologous polynucleotide stably incorporated in their genome and comprising the nucleotide molecule described above, preferably operably linked to a promoter element and/or operably linked to a gene of interest. The transformed plant is preferably a monocot or a dicot. The invention covers also seeds of the transformed plants. The invention covers human and non-human host cells transformed with any of the polynucleotides of the invention or the polypeptides of the invention. The promoters used in combination with any of the nucleotides and polypeptides of the invention are preferably tissue specific promoters, chemical-inducible promoters and promoters inducible by pathogens.

While the present invention can be used in animal and plant systems, one preferred optional embodiment refers to the use in plant systems. The term plant includes plant cells, plant protoplasts, plant cell tissue cultures from which plants can be regenerated, plant calli, plant clumps and plant cells that are intact in plants or parts of plants such as embryos, pollen, ovules, seed, leaves, flowers, branches, fruits, roots, root tips, anthers and the like. Progeny, variants, and mutants of the regenerated plants are also included within the scope of the invention, provided that these parts comprise the introduced polynucleotides.

Materials and Methods

Bacterial strains and growth conditions. *Escherichia coli* were cultivated at 37° C. in lysogeny broth (LB) and *Agrobacterium tumefaciens* GV3101 at 30° C. in yeast extract broth (YEB) supplemented with appropriate antibiotics.

Plant material and inoculations. *Nicotiana benthamiana* plants were grown in the greenhouse (day and night temperatures of 23° C. and 19° C., respectively) with 16 h light and 40 to 60% humidity. Mature leaves of five- to seven-week-old plants were inoculated with *Agrobacterium* using a needleless syringe as described previously (S1). Inoculated plants were transferred to a Percival growth chamber (Percival Scientific) with 16 h light, 22° C. and 18° C. night temperature.

Construction of artificial effectors. The construction of effectors with modified repeat region was based on ligation of Esp3I (Fermentas) restriction fragments. Esp3I cuts outside of its recognition sequence and typically once per repeat. To construct a GATEWAY (Invitrogen)-compatible ENTRY-vector for generation of effectors of the invention, the N- and C-termini of hax3 were amplified by PCR using a proof reading polymerase (HotStar HiFidelity Polymerase Kit; Qiagen), combined by SOE (splicing by overlap extension)-PCR and inserted into pCR8/GW/TOPO resulting in a hax3-derivative with 1.5 repeat units (pC3SE26; first repeat=NI; last half repeat=NG). A 1 bp frame-shift preceding the start codon was inserted by site-directed mutagenesis to allow in frame N-terminal fusions using GATEWAY recombination (Invitrogen) resulting in pC3SEIF. Single repeat units were amplified from TAL effectors using a forward primer binding to most repeat units and repeat-specific reverse primers. Both primers included the naturally present Esp3I sites. To avoid amplification of more than one repeat, template DNA was digested with Esp3I prior to the PCR reaction. PCR-products were digested with Esp3I and cloned into Esp3I-digested pC3SE26 yielding Hax3-derivatives with 2.5 repeat units where a single repeat can be excised with Esp3I (HD-repeat=repeat 5 of Hax3; NI-repeat=repeat 11 of Hax3; NG-repeat=repeat 4 of Hax4; NN-repeat=$G_{13}N$ mutant of repeat 4 of Hax4). The ArtHD effector backbone construct consists of the N- and C-terminus of Hax3 with the last half repeat mutated into a HD-repeat. The resulting construct was restricted by Esp3I and dephosphorylated. DNA fragments encoding repeat units were excised with Esp3I from pC3SE26-derivatives containing a single HD-repeat and purified via agarose gels. Ligation was performed using a molar excess of insert to vector to facilitate concatemer ligation and transformed into E. coli. The number of repeat units was determined in recombinant plasmids using StuI and HincII. ArtX1-3 effectors with a random combination of repeat types were generated by isolating DNA fragments encoding repeat units as described above from cloned single NI-, HD-, NN-, and NG-repeat units (specificities for A, C, G/A, and T, respectively). The fragments were added in equal molar amounts each to the concatemer ligation reaction with vector pC3SEIF. Plasmids containing effectors of the invention with 12.5 repeat units were chosen for subsequent analysis. Effectors were cloned by GATEWAY-recombination (Invitrogen) into pGWB6 (S2) for expression of N-terminal GFP-effector fusions. Oligonucleotide sequences are available upon request. All constructs were sequenced.

GUS reporter constructs. The minimal Bs4 promoter was amplified by PCR and inserted into pENTR/D-TOPO (Invitrogen) with target DNA boxes at the 5' end (S3; FIG. S5). Promoter derivatives were cloned into pGWB3 (S2) containing a promoterless uidA gene.

Construction of hax2-transgenic A. thaliana. hax2 was cloned under control of the inducible alcA promoter from Aspergillus nidulans into a GATEWAY-compatible derivative of the binary T-DNA vector binSRNACatN (Zeneca Agrochemicals) containing the 35S-driven alcR ethanol-dependent regulator gene and a nptII selection marker. AlcR drives ethanol-dependent induction of the alcA promoter (S4). T-DNA containing these genes was transformed into A. thaliana Col-0 via A. tumefaciens using floral dip inoculation (S5). Transformants were selected as kanamycin-resistant plants on sterile medium.

Construction of ARTBs4, an artificial effector. "Golden gate" cloning (Engler et al. (2008) PLoS ONE 3:e3647) was used to assemble effectors with 11.5 specifically ordered repeat units. The N- and C-terminus of Hax3 and 12 individual repeat units resembling the 11.5 repeat units were subcloned. Each building block contained individual flanking BsaI sites that allowed an ordered assembly of the fragments into an artificial effector. For the targeted assembly of effectors with any desired repeat composition, the building block repertoire of repeat units was expanded. To allow for target specificity to any of the four natural bases (A, C, G, and T) in DNA, four different repeat types were chosen, based on the amino acids 12 and 13 per repeat unit. The four repeat types and their specificities are: NI=A; HD=C; NG=T, NN=G or A. To generate a universally applicable assembly kit, four units corresponding to each of the four repeat unit types were cloned with flanking BsaI sites for each of the 12 repeat positions. The sum of 48 building blocks resembles a library that can be used to assemble effectors with 11.5 repeat units with any composition of the four repeat unit types.

β-Glucuronidase (GUS) assays. For transient GUS assays Agrobacterium strains delivering effector constructs and GUS reporter constructs were mixed 1:1, and inoculated into Nicotiana benthamiana leaves with an $OD_{600}$ of 0.8. Two leaf discs (0.9 cm diameter) were sampled two days post infiltration (dpi) and quantitative GUS activity was determined using 4-methyl-umbelliferyl-β-D-glucuronide (MUG), as described previously (S1). Proteins were quantified using Bradford assays (BioRad). Data correspond to triplicate samples from different plants. For qualitative GUS assays, leaf discs were sampled 2 dpi, incubated in X-Gluc (5-bromo-4-chloro-3-indolyl-β-D-glucuronide) staining solution (S3), destained in ethanol, and dried. Experiments were performed at least twice with similar results.

Expression of hax2, hax3, and hax4. hax2, hax3, and hax4 were expressed in planta under control of the constitutive cauliflower mosaic virus 35S promoter using pAGH2, pAGH3, and pAGH4 (S6).

DNaseI footprinting. DNaseI footprinting was performed as described (S7) with the following modifications: Fluorescently labeled PCR products of Bs3 and Bs3-E promoter DNA were generated using plasmids pCRBluntII-TOPO::FPBs3 (Bs3 promoter fragment from −211 to +108) and pCRBluntII-TOPO::FPBs3-E (Bs3-E promoter fragment from −224 to +108), respectively, as template and Phusion DNA polymerase (Finnzymes). Fluorescently labeled PCR product of UPA20-ubm-r16 promoter DNA was generated using plasmid pCRBluntII-TOPO::FPU20-ubm-r16 (UPA20 promoter fragment from -213 to +86 containing the ubm-r16 mutation (S7) as template and Phusion DNA polymerase (Finnzymes). Plasmids pCRBluntII-TOPO::FPBs3, pCRBluntII-TOPO::FPBs3-E and pCRBluntII-TOPO::FPU20-ubm-r16 were sequenced, using the Thermo Sequenase Dye Primer Manual Cycle Sequencing Kit (USB) according to the manufacturer's instructions. An internal Gene Scan-500LIZ Size Standard (Applied Biosystems) was used to determine the DNA fragment size.

Example 2

Identification of a TAL Repeat Unit That Binds to G Nucleotides

The DNA binding domain of TAL effectors is composed of tandem-arranged 34-amino acid repeat units. The amino acid sequences of the repeat units are mostly conserved, except for two adjacent highly variable residues (HVRs) at positions 12 and 13 that define DNA target specificity (Boch et al. (2009) Science 326:1509-1512; Moscou & Bogdanove (2009) *Science* 326:1501). Functional analysis identified HVR motifs that bind preferentially to A (NI), C (HD), T (NG, IG) or equally well to G and A (NN) (Boch et al. (2009) *Science* 326:1509-1512). Bioinformatic analysis revealed HVRs that in the given promoter-TAL effector interactions match specifically to G (Moscou & Bogdanove (2009) *Science* 326:1501). However this, analysis was based on a single (HN & NA) or two (NK) interaction sites. In our view the number of interaction sites is too low to make reliable conclusions on the HVR specificity. Yet, these HVRs can be considered as suitable candidates that may mediate specific binding to G.

In order to clarify the target specificity of HVRs with unknown specificity we made use of the well-characterized interaction between AvrBs3 and the UPA box in the Bs3 promoter. Using site directed mutagenesis we replaced the HVR NI in the $5^{th}$ and the $6^{th}$ repeat unit by NK resulting in AvrBs3-NK$_{5/6}$. In the wildtype Bs3 promoter the NI residues of the $5^{th}$ and the $6^{th}$ repeat both match to A nucleotides. Using site-directed mutagenesis we replaced the two A nucleotides in the Bs3 promoter by two C, G and T nucleotides. The wildtype Bs3 promoter and the three promoter mutants were fused to an uidA reporter gene and tested via *Agrobacterium tumefaciens* transient expression in combination with either wildtype AvrBs3 or AvrBs3-NK$_{5/6}$ in *Nicotiana benthamiana* leaves. GUS assays revealed that AvrBs3-NK$_{5/6}$ activated the GUS reporter only in combination with the "GG" Bs3 promoter mutant while AvrBs3 activated only the Bs3 wildtype promoter construct.

Our analysis suggests that NK pairs specifically to G and thus provides an option to generate more specific repeat arrays and also to specifically target G-rich target sequences.

Example 3

Method for Generation of Designer Effectors via Golden Gate Cloning

The DNA binding domain of TAL effectors is composed of tandem-arranged 34-amino acid repeat units. The amino acid sequences of the repeat units are mostly conserved, except for two adjacent highly variable residues (HVRs) at positions 12 and 13 that define DNA target specificity (Boch et al. (2009) *Science* 326:1509-1512; Moscou & Bogdanove (2009) *Science* 326:1501). Different HVR motifs bind with different levels of specificity to individual A, C, G or T nucleotides. Importantly, statistical analysis suggests that tandem arranged repeat units do not to interfere with the specificity of adjacent units (Moscou & Bogdanove (2009) *Science* 326:1501). Thus modular assembly of repeat units with pre-characterized specificities is likely to provide an efficient way for generation of DNA-recognition modules with desired DNA specificity.

However, the generation of DNA constructs that encode desired repeat domains is challenging due to the fact that the repeat units are almost identical. In the past we have used chemical synthesis to generate effectors genes that encode 17.5 repeat units with the desired HVR composition. To maximize the differences between repeat units at the DNA level we exploited the degeneracy of the genetic code. The codon-optimized sequence of the 17.5 repeat unit encoding DNA sequence was, in contrast to the corresponding TAL effector wildtype gene, PCR-amplifiable and amenable to PCR-based mutagenesis. Our findings also demonstrate that chemical synthesis of effector repeat domains is generally feasible. However, chemical synthesis does not allow rapid and cost-efficient generation of multiple effectors with desired HVR composition. Furthermore this approach will most likely not allow generation of repeat domains with 20 or more repeat units.

The recently developed "Golden-Gate cloning" provides an alternative approach for generation of repeat unit arrays of desired composition. The strategy is based on the use of type IIS restriction enzymes, which cut outside of their recognition sequence. We will work with the type IIS enzyme BsaI, which creates a 4-bp sticky end. Due to the fact, that recognition and cleavage site are separated in type IIS enzymes we can generate by BsaI restriction in principle 256 ($4^4$) different sticky ends which provides the basis for multi fragment ligations. With proper design of the cleavage sites, two or more fragments cut by type IIS restriction enzymes can be ligated into a product lacking the original restriction site (Engler et al. (2008) *PLoS ONE* 3:e3647; Engler et al. (2009) *PLoS ONE* 4:e5553).

However in practice there are two limitations to this method. Due to exonuclease activity in some reactions, single stranded overhanging DNA sticky ends are reduced from four to three bases, effectively making the number of compatible sticky ends only 16 ($2^4$). Secondly, the efficiency of the ligation reactions decreases precipitously with large numbers of inserts, such as would be needed to create an effector with 17.5 repeat units as typically found in naturally occurring functional TAL effectors. To circumvent these limitations, we have designed a two-stage ligation process that allows the effective production of effectors of 20, 30, 40 or more repeat units.

The basis for our "repeat-array building kit" is a set of "insert plasmids" that contain individual repeat units (one repeat unit per plasmid), "intermediate vectors" that contain repeat domains consisting of sets of 10 repeat units, and one "acceptor vector" that contains the N- and C-terminal non-repeat region of a TAL effector. All repeat units are designed in such a way that the BsaI recognition sites flank the insert in the insert plasmids.

To simplify the explanation of the multi-fragment ligation we define herein the different ends of the repeat unit genes with upper case letters (instead of the sequence overhang of the sticky end) and indicate their orientation (N- or C-terminus of the repeat unit) with N or C in square brackets (e.g. A[C]). The insert plasmid containing the $1^{st}$ repeat unit gene is designed in such a way that BsaI treatment creates A[N] and B[C] termini. The $2^{nd}$ repeat unit gene has B[N] and C[C] termini upon BsaI cleavage, while BsaI cleavage of the insert plasmid with the $3^{rd}$ repeat unit gene results in C[N] and D[C] termini, and so on. Since only compatible ends can be fused, the B[C] terminus of the $1^{st}$ repeat unit gene will fuse specifically to the B[N] terminus of the $2^{nd}$ repeat unit gene. Similarly the C[C] terminus of the $2^{nd}$ repeat unit gene will ligate specifically to the C[N] terminus of the $3^{rd}$ repeat unit gene and so on.

BsaI digestion releases the repeat units with 4-bp sticky overhangs that are compatible only with the designed adjacent repeat units. The BsaI recognition site itself remains in the cleaved insert plasmid vector and the released insert has no BsaI recognition site. The repeat units are joined together in the order specified by the overhanging ends in a cut-ligation reaction (cleavage and ligation running simultaneously). Due to the simultaneous action of BsaI and ligase the religation of repeat units into the insert donor vector is avoided since this restores the BsaI recognition site. By contrast the desired ligation products lack the BsaI recognition sites. This experimental design makes this cloning procedure highly efficient.

To generate effectors that are designed to recognize specific base sequences, four variants are made for each repeat unit position. These variants are individual repeat units with specific nucleotide recognition specificity, (e.g. HD residues at position 12 and 13 for recognition of a C base, NI for A, and so on). The variant for each position is made with the appropriate sticky ends for each repeat unit, for example A[N] and B[C] termini for repeat unit 1, such that there are four possible insert plasmids for repeat unit one, chosen based on the desired DNA recognition. There are four variants for repeat unit 2, with different nucleotide recognition specificity and B[N] and C[C] termini, and so on for each repeat position Ligations are carried out in two stages. In the first stage, 10 repeat units are combined into an intermediate vector. Different sets of 10 repeat units can be combined in intermediate vectors. Intermediate vector 1 contains repeat units 1-10, intermediate vector 2 contains repeat units 11-20 and so on. In the second stage, separately assembled 10 repeat units are combined into acceptor vectors. The acceptor vector also contains the N- and C-terminal non-repeat areas of the effector, such that a complete effector comprised of 10, 20, 30 40 or other multiples of 10 repeat units is assembled in the final construct. The intermediate vector has BsaI sites in the insert for introducing the 10 repeat unit fragments and also has flanking BpiI sites in the flanking vector sequence. BpiI is another type IIS enzyme with a recognition site distinct from BsaI. Using BsaI, the 10 repeat units are first assembled into the "intermediate vector" and using BpiI the assembled 10 mers are released as one fragment. This fragment is ligated in a BpiI cut-ligase reaction with the acceptor vector, which contains BpiI sites between the N- and C-terminal non-repeat areas of the TAL effector. In this case only 2-4 inserts are ligated into the acceptor vector. This allows to make each ligation highly specific and to assemble easily 40 and more repeat units.

The acceptor vector in which the repeat unit array is finally cloned, represents a GATEWAY Entry clone and thus allows recombination-based transfer of the effector into any desired expression construct. Currently the acceptor vector is designed to generate a TAL-type transcription factor. However, with few modifications the acceptor vector allows also fusions of the repeat array to the FokI endonuclease or other desired functional domains.

A schematic of this method is provided in FIG. 19A-D.

Example 4

Production and Testing of Target DNA-Specific Nucleases

Fusion proteins comprising a repeat domain of the invention that recognizes a target DNA sequence and a FokI nuclease ("TAL-type-nucleases") are produced as described by any of the method disclosed herein or known in the art. The fusion proteins are tested for nuclease activity by incubation with corresponding target DNA. The repeat domain DNA target site is cloned into the multiple cloning site of a plasmid vector (e.g., bluescript). As negative controls, either an "empty vector" that contains no TAL-nuclease target site or cloned target sites with mutations are used. Before treatment of the DNA substrate with the TAL-type nuclease, the vector is linearized by treatment with a suitable standard endonuclease that cleaves in the vector backbone. This linearized vector is incubated with in vitro generated repeat domain-FokI nuclease fusion proteins and the products analyzed by agarose gel electrophoresis. The detection of two DNA fragments in gel electrophoresis is indicative for specific nuclease mediated cleavage. By contrast, the negative controls that do not contain a target site that is recognized by repeat domain are unaffected by treatment with the repeat domain-FokI nuclease fusion protein. DNA-driven, cell-free systems for in vitro gene expression and protein synthesis are used to generate repeat domain-FokI nuclease fusion proteins (e.g. T7 High-Yield Protein Expression System; Promega). To use such systems, repeat domain-FokI nuclease fusion protein nucleotide sequences are cloned in front of a T7 RNA polymerase. Such fusion proteins that are produced via in vitro transcription and translation are used in DNA cleavage assays without further purification.

Example 5

Determination of Additional Recognition Specificites

Further experiments were conducted essentially as described hereinabove to determine the recognition specificities of additional amino acid pairs in the hypervariable region. DNA binding domains were constructed using Golden Gate Cloning as described in Example 3. The experiments conducted and the experimental results obtained are provided in FIGS. 20-27 and their respective figure legends.

From these experiments, the recognition specificity for the amino acids found at positions 12 and 13 in a repeat unit and the base pair in the target DNA sequence were determined for the following amino acid pairs:

NH for recognition of G/C
NP for recognition of A/T or C/G or T/A
NT for recognition of A/T or G/C
HN for recognition of A/T or G/C
SH for recognition of G/C
SN for recognition of G/C and
IS for recognition of A/T.

It is recognized that the recognition specificities set forth in this Example can be used in the methods of the present invention. It is further recognized that the recognition specificities set forth in this Example can be used to produce compositions of the present invention, such as, for example, polypeptides and DNA. Preferably, the recognition specificities set forth in this Example are used in such methods or to produce such compositions in combination with any of the other recognition specificities disclosed herein.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Additionally, each of the following patent applications is hereby herein incorporated referenced in its entirety: DE 10 2009 004 659.3 filed Jan. 12, 2009, EP 09165328 filed Jul. 13, 2009, and US 61/225,043 filed Jul. 13, 2009.

Although the foregoing invention has been described in some detail by way of illustration and example for purposes of clarity of understanding, it will be obvious that certain changes and modifications may be practiced within the scope of the appended claims.

That which is claimed:

1. An RNA encoding a fusion protein, the fusion protein comprising a transcription activator-like (TAL) effector repeat domain that is capable of selectively recognizing a target nucleotide sequence and a catalytic domain comprising an activity that is capable of modifying DNA, wherein the repeat domain comprises contiguous repeat units and wherein the order of the contiguous repeat units in the repeat domain correlates with the linear sequence of bases in the target nucleotide sequence.

2. The RNA of claim 1, wherein the catalytic domain is capable of introducing double-strand breaks into DNA in the cell.

3. A cell comprising the RNA and/or the fusion protein of claim 1.

4. The cell of claim 3, further comprising a donor DNA.

5. The cell of claim 4, wherein the donor DNA comprises a transgene.

6. The RNA of claim 1, wherein the repeat domain comprises up to 50 repeat units.

7. The RNA of claim 1, wherein the repeat domain comprises 1.5 to 50 repeat units.

8. The RNA of claim 1, wherein the repeat domain comprises 1.5 to 40.5 repeat units.

9. The RNA of claim 1, wherein the catalytic domain comprises an endonuclease domain.

* * * * *

SEQUENCE LISTING

<160> NUMBER OF SEQ ID NOS: 120

<210> SEQ ID NO 1
<211> LENGTH: 34
<212> TYPE: PRT
<213> ORGANISM: Xanthomonas campestris pv. vesicatoria

<400> SEQUENCE: 1

```
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly
```

<210> SEQ ID NO 2
<211> LENGTH: 19
<212> TYPE: DNA
<213> ORGANISM: Artificial Sequence
<220> FEATURE:
<223> OTHER INFORMATION: predicted
<220> FEATURE:
<221> NAME/KEY: misc_feature
<222> LOCATION: (12)..(13)
<223> OTHER INFORMATION: n is a, c, g, or t

<400> SEQUENCE: 2
tatataaacc tnnccctct 19

<210> SEQ ID NO 3
<211> LENGTH: 23
<212> TYPE: DNA
<213> ORGANISM: Artificial Sequence
<220> FEATURE:
<223> OTHER INFORMATION: predicted binding domain sequence

<400> SEQUENCE: 3
tgttattctc acactctcct tat 23

<210> SEQ ID NO 4
<211> LENGTH: 13
<212> TYPE: DNA
<213> ORGANISM: Artificial Sequence
<220> FEATURE:
<223> OTHER INFORMATION: predicted binding domain sequence

<400> SEQUENCE: 4
tacacccaaa cat 13

<210> SEQ ID NO 5
<211> LENGTH: 16
<212> TYPE: DNA
<213> ORGANISM: Artificial Sequence
<220> FEATURE:
<223> OTHER INFORMATION: predicted binding domain sequence

<400> SEQUENCE: 5
tacctaaact aaatat 16

<210> SEQ ID NO 6
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 6
taccaaaaca aaaaaa                                               16

<210> SEQ ID NO 7
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 7
tacccaaacc aaacac                                               16

<210> SEQ ID NO 8
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 8
taccgaaacg aaagag                                               16

<210> SEQ ID NO 9
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 9
taaataaaat aaatat                                               16

<210> SEQ ID NO 10
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 10
taggtaaagt aaatat                                               16

<210> SEQ ID NO 11
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 11
tatttaaatt aaatat                                               16

<210> SEQ ID NO 12
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 12
tccctaacct cactct                                               16

<210> SEQ ID NO 13
<211> LENGTH: 16
<212> TYPE: DNA

```
<213> ORGANISM: Artificial Sequence
<220> FEATURE:
<223> OTHER INFORMATION: constructed binding domain sequence

<400> SEQUENCE: 13
tgcctaagct gagtgt                                                     16

<210> SEQ ID NO 14
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 14
ttcctaatct tatttt                                                     16

<210> SEQ ID NO 15
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 15
tacctccact acatat                                                     16

<210> SEQ ID NO 16
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 16
tacctggact agatat                                                     16

<210> SEQ ID NO 17
<211> LENGTH: 16
<212> TYPE: DNA
<213> ORGANISM: Artificial Sequence
<220> FEATURE:
<223> OTHER INFORMATION: constructed binding domain sequence

<400> SEQUENCE: 17
tacctttact atatat                                                     16

<210> SEQ ID NO 18
<211> LENGTH: 14
<212> TYPE: DNA
<213> ORGANISM: Artificial Sequence
<220> FEATURE:
<223> OTHER INFORMATION: predicted binding domain sequence

<400> SEQUENCE: 18
tattctggga cgtt                                                       14

<210> SEQ ID NO 19
<211> LENGTH: 14
<212> TYPE: DNA
<213> ORGANISM: Artificial Sequence
<220> FEATURE:
<223> OTHER INFORMATION: constructed binding domain sequence

<400> SEQUENCE: 19
tattctaaaa catt                                                       14
```

<210> SEQ ID NO 20
<211> LENGTH: 14
<212> TYPE: DNA
<213> ORGANISM: Artificial Sequence
<220> FEATURE:
<223> OTHER INFORMATION: constructed binding domain sequence

<400> SEQUENCE: 20
tattctccca cctt                                                         14

<210> SEQ ID NO 21
<211> LENGTH: 14
<212> TYPE: DNA
<213> ORGANISM: Artificial Sequence
<220> FEATURE:
<223> OTHER INFORMATION: constructed binding domain sequence

<400> SEQUENCE: 21 tattcttta cttt                                                          14

<210> SEQ ID NO 22
<211> LENGTH: 14
<212> TYPE: DNA
<213> ORGANISM: Artificial Sequence
<220> FEATURE:
<223> OTHER INFORMATION: predicted binding domain sequence

<400> SEQUENCE: 22
tatgcggtcc ctct                                                         14

<210> SEQ ID NO 23
<211> LENGTH: 14
<212> TYPE: DNA
<213> ORGANISM: Artificial Sequence
<220> FEATURE:
<223> OTHER INFORMATION: predicted binding domain sequence

<400> SEQUENCE: 23
tatgggtgcc ctat                                                         14

<210> SEQ ID NO 24
<211> LENGTH: 19
<212> TYPE: DNA
<213> ORGANISM: Artificial Sequence
<220> FEATURE:
<223> OTHER INFORMATION: predicted binding domain sequence

<400> SEQUENCE: 24
tacccccccc cccccccc                                                     19

<210> SEQ ID NO 25
<211> LENGTH: 19
<212> TYPE: DNA
<213> ORGANISM: Capsicum annuum

<400> SEQUENCE: 25
tatataaacc taaccatcc                                                    19

<210> SEQ ID NO 26
<211> LENGTH: 19
<212> TYPE: DNA
<213> ORGANISM: Capsicum annuum

<400> SEQUENCE: 26
tatataaacc tctctattc                                            19

<210> SEQ ID NO 27
<211> LENGTH: 18
<212> TYPE: DNA
<213> ORGANISM: Oryza sativa

<400> SEQUENCE: 27
tagaagaaga gacccata                                             18

<210> SEQ ID NO 28
<211> LENGTH: 18
<212> TYPE: DNA
<213> ORGANISM: Oryza sativa

<400> SEQUENCE: 28
tagaagagac caatagag                                             18

<210> SEQ ID NO 29
<211> LENGTH: 25
<212> TYPE: DNA
<213> ORGANISM: Oryza sativa

<400> SEQUENCE: 29
tgcatctccc cctactgtac accac                                     25

<210> SEQ ID NO 30
<211> LENGTH: 25
<212> TYPE: DNA
<213> ORGANISM: Oryza sativa

<400> SEQUENCE: 30
gatatgtccc cctccaacta tataa                                     25

<210> SEQ ID NO 31
<211> LENGTH: 24
<212> TYPE: DNA
<213> ORGANISM: Oryza sativa

<400> SEQUENCE: 31
tataaaaggc cctcaccaac ccat                                      24

<210> SEQ ID NO 32
<211> LENGTH: 23
<212> TYPE: DNA
<213> ORGANISM: Oryza sativa

<400> SEQUENCE: 32
tataatcccc aaatccctc ctc                                        23

<210> SEQ ID NO 33
<211> LENGTH: 37
<212> TYPE: DNA
<213> ORGANISM: Capsicum annuum

<400> SEQUENCE: 33
ttttattata taaacctaac catcctcaca acttcaa                        37

<210> SEQ ID NO 34
<211> LENGTH: 36
<212> TYPE: DNA
<213> ORGANISM: Capsicum annuum

<400> SEQUENCE: 34

```
gttgtgagga tggttaggtt tatataataa aattgg                                    36

<210> SEQ ID NO 35
<211> LENGTH: 30
<212> TYPE: DNA
<213> ORGANISM: Capsicum annuum

<400> SEQUENCE: 35
tttattatat aaacctctct attccactaa                                           30

<210> SEQ ID NO 36
<211> LENGTH: 32
<212> TYPE: DNA
<213> ORGANISM: Capsicum annuum

<400> SEQUENCE: 36
gtggaataga gaggtttata taataaaatt gg                                        32

<210> SEQ ID NO 37
<211> LENGTH: 35
<212> TYPE: DNA
<213> ORGANISM: Artificial Sequence
<220> FEATURE:
<223> OTHER INFORMATION: constructed binding domain sequence

<400> SEQUENCE: 37
catctttata taaacctctc cctttgtgac attct                                     35

<210> SEQ ID NO 38
<211> LENGTH: 34
<212> TYPE: DNA
<213> ORGANISM: Artificial Sequence
<220> FEATURE:
<223> OTHER INFORMATION: constructed binding domain sequence

<400> SEQUENCE: 38
gtcacaaagg gagaggttta tataaagatg aaga                                      34

<210> SEQ ID NO 39
<211> LENGTH: 31
<212> TYPE: DNA
<213> ORGANISM: Artificial Sequence
<220> FEATURE:
<223> OTHER INFORMATION: constructed binding domain sequence

<400> SEQUENCE: 39
catctttata taaacctctc cctttgtgac a                                         31

<210> SEQ ID NO 40
<211> LENGTH: 32
<212> TYPE: DNA
<213> ORGANISM: Artificial Sequence
<220> FEATURE:
<223> OTHER INFORMATION: constructed binding domain sequence

<400> SEQUENCE: 40
cacaaaggga gaggtttata taaagatgaa ga                                        32

<210> SEQ ID NO 41
<211> LENGTH: 19
<212> TYPE: DNA
<213> ORGANISM: Artificial Sequence
<220> FEATURE:
<223> OTHER INFORMATION: constructed binding domain sequence
```

```
<400> SEQUENCE: 41
tatataaacc tctcccttt                                               19

<210> SEQ ID NO 42
<211> LENGTH: 44
<212> TYPE: DNA
<213> ORGANISM: Capsicum annuum

<400> SEQUENCE: 42
caattttatt atataaacct aaccatcctc acaacttcaa gtta                   44

<210> SEQ ID NO 43
<211> LENGTH: 44
<212> TYPE: DNA
<213> ORGANISM: Capsicum annuum

<400> SEQUENCE: 43
ttgaagttgt gaggatggtt aggtttatat aataaaattg gtca                   44

<210> SEQ ID NO 44
<211> LENGTH: 44
<212> TYPE: DNA
<213> ORGANISM: Capsicum annuum

<400> SEQUENCE: 44
ccaattttat tatataaacc tctctattcc actaaaccat cctc                   44

<210> SEQ ID NO 45
<211> LENGTH: 46
<212> TYPE: DNA
<213> ORGANISM: Capsicum annuum

<400> SEQUENCE: 45
gatggtttag tggaatagag aggtttatat aataaaattg gtcagg                 46

<210> SEQ ID NO 46
<211> LENGTH: 43
<212> TYPE: DNA
<213> ORGANISM: Artificial Sequence
<220> FEATURE:
<223> OTHER INFORMATION: constructed binding domain sequence

<400> SEQUENCE: 46
tcttcatctt tatataaacc tctcccttg tgacattctg aga                     43

<210> SEQ ID NO 47
<211> LENGTH: 44
<212> TYPE: DNA
<213> ORGANISM: Artificial Sequence
<220> FEATURE:
<223> OTHER INFORMATION: constructed binding domain sequence

<400> SEQUENCE: 47
cagaatgtca caaagggaga ggtttatata aagatgaaga gaga                   44

<210> SEQ ID NO 48
<211> LENGTH: 20
<212> TYPE: DNA
<213> ORGANISM: Artificial Sequence
<220> FEATURE:
<223> OTHER INFORMATION: constructed binding domain sequence

<400> SEQUENCE: 48
ccgcggccgc ccccttcacc                                              20
```

-continued

```
<210> SEQ ID NO 49
<211> LENGTH: 75
<212> TYPE: DNA
<213> ORGANISM: Solanum lycopersicum

<400> SEQUENCE: 49
ttctttcttg tatataactt tgtccaaaat atcatcaatt gatctcatcc atacaattta      60
tttttaatcg aatct                                                      75

<210> SEQ ID NO 50
<211> LENGTH: 25
<212> TYPE: DNA
<213> ORGANISM: Artificial Sequence
<220> FEATURE:
<223> OTHER INFORMATION: sequence generated during cloning

<400> SEQUENCE: 50
tctagaccca agggtgggcg cgccg                                           25

<210> SEQ ID NO 51
<211> LENGTH: 13
<212> TYPE: DNA
<213> ORGANISM: Artificial Sequence
<220> FEATURE:
<223> OTHER INFORMATION: constructed binding domain sequence

<400> SEQUENCE: 51
aacacccaaa cat                                                        13

<210> SEQ ID NO 52
<211> LENGTH: 13
<212> TYPE: DNA
<213> ORGANISM: Artificial Sequence
<220> FEATURE:
<223> OTHER INFORMATION: constructed binding domain sequence

<400> SEQUENCE: 52
cacacccaaa cat                                                        13

<210> SEQ ID NO 53
<211> LENGTH: 13
<212> TYPE: DNA
<213> ORGANISM: Artificial Sequence
<220> FEATURE:
<223> OTHER INFORMATION: constructed binding domain sequence

<400> SEQUENCE: 53
gacacccaaa cat                                                        13

<210> SEQ ID NO 54
<211> LENGTH: 17
<212> TYPE: DNA
<213> ORGANISM: Artificial Sequence
<220> FEATURE:
<223> OTHER INFORMATION: predicted binding domain sequence

<400> SEQUENCE: 54
tatataaaca catatct                                                    17

<210> SEQ ID NO 55
<211> LENGTH: 17
<212> TYPE: DNA
<213> ORGANISM: Artificial Sequence
<220> FEATURE:
```

<223> OTHER INFORMATION: predicted binding domain sequence

<400> SEQUENCE: 55
tatataagca cgtatct                                                    17

<210> SEQ ID NO 56
<211> LENGTH: 23
<212> TYPE: DNA
<213> ORGANISM: Artificial Sequence
<220> FEATURE:
<223> OTHER INFORMATION: constructed binding domain sequence

<400> SEQUENCE: 56
tgatattctc acactctcct tat                                             23

<210> SEQ ID NO 57
<211> LENGTH: 23
<212> TYPE: DNA
<213> ORGANISM: Artificial Sequence
<220> FEATURE:
<223> OTHER INFORMATION: constructed binding domain sequence

<400> SEQUENCE: 57
tgctattctc acactctcct tat                                             23

<210> SEQ ID NO 58
<211> LENGTH: 23
<212> TYPE: DNA
<213> ORGANISM: Artificial Sequence
<220> FEATURE:
<223> OTHER INFORMATION: constructed binding domain sequence

<400> SEQUENCE: 58
tggtattctc acactctcct tat                                             23

<210> SEQ ID NO 59
<211> LENGTH: 150
<212> TYPE: DNA
<213> ORGANISM: Arabidopsis thaliana

<400> SEQUENCE: 59 tgttttata aatttctca catactcaca ctctctataa gacctccaat catttgtgaa       60
accatactat atatccctc ttccttgacc aatttactta taccttttac aatttgttta    120
tatattttac gtatctatct ttgttccatg                                    150

<210> SEQ ID NO 60
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 60 tctntaaaacc tnncctct                                                  19

<210> SEQ ID NO 61
<211> LENGTH: 15

```
<212> TYPE: DNA
<213> ORGANISM: Artificial Sequence
<220> FEATURE:
<223> OTHER INFORMATION: predicted binding domain sequence

<400> SEQUENCE: 61
trtaaacctr accct                                                      15

<210> SEQ ID NO 62
<211> LENGTH: 23
<212> TYPE: DNA
<213> ORGANISM: Artificial Sequence
<220> FEATURE:
<223> OTHER INFORMATION: predicted binding domain sequence

<400> SEQUENCE: 62
tgttattctc acactctcct tat                                             23

<210> SEQ ID NO 63
<211> LENGTH: 13
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (8)..(10)
<223> OTHER INFORMATION: n is a, c, g, or t

<400> SEQUENCE: 63
tacacccnnn cat                                                        13

<210> SEQ ID NO 64
<211> LENGTH: 16
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 64
tacctnnact anatat                                                     16

<210> SEQ ID NO 65
<211> LENGTH: 17
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 65
```
tananaarca crnntct                                                                                            17

<210> SEQ ID NO 66
<211> LENGTH: 18
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 66
tarntnrrra ranccatt                                                                                           18

<210> SEQ ID NO 67
<211> LENGTH: 25
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t

<400> SEQUENCE: 67
trcanctncc attactrtaa aannn                                                                                   25

<210> SEQ ID NO 68
<211> LENGTH: 24
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 68
tanarrrrrc acncannaan cnnt                                          24

<210> SEQ ID NO 69
<211> LENGTH: 23
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 69
tataanrccn aaatcnrnrc ctn                                           23

<210> SEQ ID NO 70
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 70
tataattant antccnctt                                                19

<210> SEQ ID NO 71
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (15)..(15)
<223> OTHER INFORMATION: n is a, c, g, or t

<400> SEQUENCE: 71
tataaacctc ttttncctt                                                19

<210> SEQ ID NO 72
<211> LENGTH: 17
<212> TYPE: DNA

```
<213> ORGANISM: Artificial Sequence
<220> FEATURE:
<223> OTHER INFORMATION: predicted binding domain sequence

<400> SEQUENCE: 72
tatacacctc ttttact                                                    17

<210> SEQ ID NO 73
<211> LENGTH: 25
<212> TYPE: DNA
<213> ORGANISM: Artificial Sequence
<220> FEATURE:
<223> OTHER INFORMATION: predicted binding domain sequence

<400> SEQUENCE: 73
tacacacctc ctaccacctc tactt                                           25

<210> SEQ ID NO 74
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (15)..(15)
<223> OTHER INFORMATION: n is a, c, g, or t

<400> SEQUENCE: 74
tataaatctc ttttncctt                                                  19

<210> SEQ ID NO 75
<211> LENGTH: 19
<212> TYPE: DNA
<213> ORGANISM: Artificial Sequence
<220> FEATURE:
<223> OTHER INFORMATION: predicted binding domain sequence

<400> SEQUENCE: 75
tctctatctc aaccccttt                                                  19

<210> SEQ ID NO 76
<211> LENGTH: 19
<212> TYPE: DNA
<213> ORGANISM: Artificial Sequence
<220> FEATURE:
<223> OTHER INFORMATION: predicted binding domain sequence

<400> SEQUENCE: 76
tctccatata actcccttt                                                  19

<210> SEQ ID NO 77
<211> LENGTH: 16
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 77
tacacatnan accact                                                     16
```

<210> SEQ ID NO 78
<211> LENGTH: 15
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (10)..(10)
<223> OTHER INFORMATION: n is a, c, g, or t

<400> SEQUENCE: 78
tcatccacan cccrt                                                        15

<210> SEQ ID NO 79
<211> LENGTH: 15
<212> TYPE: DNA
<213> ORGANISM: Artificial Sequence
<220> FEATURE:
<223> OTHER INFORMATION: predicted binding domain sequence

<400> SEQUENCE: 79
taccacatar cattr                                                        15

<210> SEQ ID NO 80
<211> LENGTH: 14
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (7)..(8)
<223> OTHER INFORMATION: n is a, c, g, or t

<400> SEQUENCE: 80
taaracnnrt crat                                                         14

<210> SEQ ID NO 81
<211> LENGTH: 10
<212> TYPE: DNA
<213> ORGANISM: Artificial Sequence
<220> FEATURE:
<223> OTHER INFORMATION: predicted binding domain sequence

<400> SEQUENCE: 81 tcccttrcct                                                              10

<210> SEQ ID NO 82
<211> LENGTH: 27
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (17)..(18)

<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t

<400> SEQUENCE: 82
tanaancrcc cnnnccnnrr atrannn                                               27

<210> SEQ ID NO 83
<211> LENGTH: 25
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 83
trcntcrtac ncrcrcrrrr rrrct                                                 25

<210> SEQ ID NO 84
<211> LENGTH: 18
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 84
tananaccna cacnacct                                                         18

<210> SEQ ID NO 85
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature

```
<222> LOCATION: (20)..(20)
<223> OTHER INFORMATION: n is a, c, g, or t

<400> SEQUENCE: 85
tatrtntara rarntnratn t                                      21

<210> SEQ ID NO 86
<211> LENGTH: 17
<212> TYPE: DNA
<213> ORGANISM: Artificial Sequence
<220> FEATURE:
<223> OTHER INFORMATION: predicted binding domain sequence

<400> SEQUENCE: 86
tacacacctc ttttaat                                           17

<210> SEQ ID NO 87
<211> LENGTH: 20
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 87
tanaancrcc cntnccnnrt                                        20

<210> SEQ ID NO 88
<211> LENGTH: 17
<212> TYPE: DNA
<213> ORGANISM: Artificial Sequence
<220> FEATURE:
<223> OTHER INFORMATION: predicted binding domain sequence

<400> SEQUENCE: 88
tacacatctt taaaact                                           17

<210> SEQ ID NO 89
<211> LENGTH: 28
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
```

```
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 89
tananrtrnn nrnncnccn ncncccct                                     28

<210> SEQ ID NO 90
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 90
tanaaacctc ttttncctt                                              19

<210> SEQ ID NO 91
<211> LENGTH: 23
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 91
tanarrarca cnnncrctcc ctt                                         23

<210> SEQ ID NO 92
<211> LENGTH: 30
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
```

```
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 92
tananaaacr ccctctaccr narrtrcnnn                              30

<210> SEQ ID NO 93
<211> LENGTH: 16
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t

<400> SEQUENCE: 93
tatrtntara racnnt                                             16

<210> SEQ ID NO 94
<211> LENGTH: 17
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 94
tarraaacnn rrraanc                                            17

<210> SEQ ID NO 95
<211> LENGTH: 17
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 95
tancnnrcnt rrcctct                                            17

<210> SEQ ID NO 96
```

-continued

```
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 96
tananrtrnn nrnnancacc t                                              21

<210> SEQ ID NO 97
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 97
tanaaarcnr nrcracrnt                                                 19

<210> SEQ ID NO 98
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
```

```
<222> LOCATION: (16)..(16)
<223> OTHER INFORMATION: n is a, c, g, or t

<400> SEQUENCE: 98
tannnncntc rtntcnccar t                                              21

<210> SEQ ID NO 99
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 99
tanaaarcnr nrcracrnt                                                 19

<210> SEQ ID NO 100
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 100
tannnncntc rtntcnccar t                                              21

<210> SEQ ID NO 101
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
```

```
<221> NAME/KEY: misc_feature
<222> LOCATION: (15)..(16)
<223> OTHER INFORMATION: n is a, c, g, or t

<400> SEQUENCE: 101
tccctnrccn aarcnncact t                                              21

<210> SEQ ID NO 102
<211> LENGTH: 28
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 102
tccrrttcnn ctncccnrar cnncnrnt                                       28

<210> SEQ ID NO 103
<211> LENGTH: 14
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 103
tarannrncn ccct                                                      14

<210> SEQ ID NO 104
<211> LENGTH: 25
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (4)..(4)
<223> OTHER INFORMATION: n is a, c, g, or t
```

```
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 104
trcntcrnac ncrcrcrrrr rrrct                                              25

<210> SEQ ID NO 105
<211> LENGTH: 22
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t

<400> SEQUENCE: 105
trcccaarac ccnrrcnrcn nn                                                 22

<210> SEQ ID NO 106
<211> LENGTH: 19
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 106
tanaaarcnr nrcracrnt                                                     19

<210> SEQ ID NO 107
<211> LENGTH: 18
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (15)..(15)
```

<223> OTHER INFORMATION: n is a, c, g, or t

<400> SEQUENCE: 107
tncatattcr atcrnrtr                                                       18

<210> SEQ ID NO 108
<211> LENGTH: 21
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 108
tncatataat tcratcrnrt r                                                   21

<210> SEQ ID NO 109
<211> LENGTH: 20
<212> TYPE: DNA
<213> ORGANISM: Artificial Sequence
<220> FEATURE:
<223> OTHER INFORMATION: predicted binding domain sequence
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 109
tataacaccc tcnacatant                                                     20

<210> SEQ ID NO 110
<211> LENGTH: 1164
<212> TYPE: PRT
<213> ORGANISM: Xanthomonas campestris pv. vesicatoria
<220> FEATURE:
<221> NAME/KEY: N-terminus
<222> LOCATION: (1)..(288)
<220> FEATURE:
<221> NAME/KEY: Repeat 1
<222> LOCATION: (289)..(322)
<220> FEATURE:
<221> NAME/KEY: Repeat 2
<222> LOCATION: (323)..(356)
<220> FEATURE:
<221> NAME/KEY: Repeat 3
<222> LOCATION: (357)..(390)
<220> FEATURE:
<221> NAME/KEY: Repeat 4
<222> LOCATION: (391)..(424)
<220> FEATURE:
<221> NAME/KEY: Repeat 5
<222> LOCATION: (425)..(458)
<220> FEATURE:
<221> NAME/KEY: Repeat 6
<222> LOCATION: (459)..(492)
<220> FEATURE:
<221> NAME/KEY: Repeat 7
<222> LOCATION: (493)..(526)
<220> FEATURE:
<221> NAME/KEY: Repeat 8
<222> LOCATION: (527)..(560)
<220> FEATURE:

```
<221> NAME/KEY: Repeat 9
<222> LOCATION: (561)..(594)
<220> FEATURE:
<221> NAME/KEY: Repeat 10
<222> LOCATION: (595)..(628)
<220> FEATURE:
<221> NAME/KEY: Repeat 11
<222> LOCATION: (629)..(662)
<220> FEATURE:
<221> NAME/KEY: Repeat 12
<222> LOCATION: (663)..(696)
<220> FEATURE:
<221> NAME/KEY: Repeat 13
<222> LOCATION: (697)..(730)
<220> FEATURE:
<221> NAME/KEY: Repeat 14
<222> LOCATION: (731)..(764)
<220> FEATURE:
<221> NAME/KEY: Repeat 15
<222> LOCATION: (765)..(798)
<220> FEATURE:
<221> NAME/KEY: Repeat 16
<222> LOCATION: (799)..(832)
<220> FEATURE:
<221> NAME/KEY: Repeat 17
<222> LOCATION: (833)..(866)
<220> FEATURE:
<221> NAME/KEY: Repeat 17.5
<222> LOCATION: (867)..(886)
<220> FEATURE:
<221> NAME/KEY: C-terminus
<222> LOCATION: (887)..(1164)

<400> SEQUENCE: 110
```

Met Asp Pro Ile Arg Ser Arg Thr Pro Ser Pro Ala Arg Glu Leu Leu
1               5                   10                  15

Pro Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
50                  55                  60

Ser Ala Gly Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

-continued

```
Leu Leu Thr Val Ala Gly Glu Leu Arg Gly Pro Pro Leu Gln Leu Asp
                245                 250                 255
Thr Gly Gln Leu Leu Lys Ile Ala Lys Arg Gly Gly Val Thr Ala Val
            260                 265                 270
Glu Ala Val His Ala Trp Arg Asn Ala Leu Thr Gly Ala Pro Leu Asn
        275                 280                 285
Leu Thr Pro Glu Gln Val Val Ala Ile Ala Ser His Asp Gly Gly Lys
    290                 295                 300
Gln Ala Leu Glu Thr Val Gln Arg Leu Leu Pro Val Leu Cys Gln Ala
305                 310                 315                 320
His Gly Leu Thr Pro Gln Gln Val Val Ala Ile Ala Ser Asn Gly Gly
                325                 330                 335
Gly Lys Gln Ala Leu Glu Thr Val Gln Arg Leu Leu Pro Val Leu Cys
            340                 345                 350
Gln Ala His Gly Leu Thr Pro Gln Gln Val Val Ala Ile Ala Ser Asn
        355                 360                 365
Ser Gly Gly Lys Gln Ala Leu Glu Thr Val Gln Arg Leu Leu Pro Val
    370                 375                 380
Leu Cys Gln Ala His Gly Leu Thr Pro Glu Gln Val Val Ala Ile Ala
385                 390                 395                 400
Ser Asn Gly Gly Gly Lys Gln Ala Leu Glu Thr Val Gln Arg Leu Leu
                405                 410                 415
Pro Val Leu Cys Gln Ala His Gly Leu Thr Pro Glu Gln Val Val Ala
            420                 425                 430
Ile Ala Ser Asn Ile Gly Gly Lys Gln Ala Leu Glu Thr Val Gln Ala
        435                 440                 445
Leu Leu Pro Val Leu Cys Gln Ala His Gly Leu Thr Pro Glu Gln Val
    450                 455                 460
Val Ala Ile Ala Ser Asn Ile Gly Gly Lys Gln Ala Leu Glu Thr Val
465                 470                 475                 480
Gln Ala Leu Leu Pro Val Leu Cys Gln Ala His Gly Leu Thr Pro Glu
                485                 490                 495
Gln Val Val Ala Ile Ala Ser Asn Ile Gly Gly Lys Gln Ala Leu Glu
            500                 505                 510
Thr Val Gln Ala Leu Leu Pro Val Leu Cys Gln Ala His Gly Leu Thr
        515                 520                 525
Pro Glu Gln Val Val Ala Ile Ala Ser His Asp Gly Gly Lys Gln Ala
    530                 535                 540
Leu Glu Thr Val Gln Arg Leu Leu Pro Val Leu Cys Gln Ala His Gly
545                 550                 555                 560
Leu Thr Pro Glu Gln Val Val Ala Ile Ala Ser His Asp Gly Gly Lys
                565                 570                 575
Gln Ala Leu Glu Thr Val Gln Arg Leu Leu Pro Val Leu Cys Gln Ala
            580                 585                 590
His Gly Leu Thr Pro Gln Gln Val Val Ala Ile Ala Ser Asn Gly Gly
        595                 600                 605
Gly Lys Gln Ala Leu Glu Thr Val Gln Arg Leu Leu Pro Val Leu Cys
    610                 615                 620
Gln Ala His Gly Leu Thr Pro Glu Gln Val Val Ala Ile Ala Ser Asn
625                 630                 635                 640
Ser Gly Gly Lys Gln Ala Leu Glu Thr Val Gln Ala Leu Leu Pro Val
                645                 650                 655
```

```
Leu Cys Gln Ala His Gly Leu Thr Pro Glu Gln Val Val Ala Ile Ala
            660                 665                 670

Ser Asn Ser Gly Gly Lys Gln Ala Leu Glu Thr Val Gln Arg Leu Leu
            675                 680                 685

Pro Val Leu Cys Gln Ala His Gly Leu Thr Pro Glu Gln Val Val Ala
        690                 695                 700

Ile Ala Ser His Asp Gly Gly Lys Gln Ala Leu Glu Thr Val Gln Arg
705                 710                 715                 720

Leu Leu Pro Val Leu Cys Gln Ala His Gly Leu Thr Pro Glu Gln Val
                725                 730                 735

Val Ala Ile Ala Ser His Asp Gly Gly Lys Gln Ala Leu Glu Thr Val
            740                 745                 750

Gln Arg Leu Leu Pro Val Leu Cys Gln Ala His Gly Leu Thr Pro Glu
        755                 760                 765

Gln Val Val Ala Ile Ala Ser His Asp Gly Gly Lys Gln Ala Leu Glu
    770                 775                 780

Thr Val Gln Arg Leu Leu Pro Val Leu Cys Gln Ala His Gly Leu Thr
785                 790                 795                 800

Pro Gln Gln Val Val Ala Ile Ala Ser Asn Gly Gly Gly Arg Pro Ala
                805                 810                 815

Leu Glu Thr Val Gln Arg Leu Leu Pro Val Leu Cys Gln Ala His Gly
            820                 825                 830

Leu Thr Pro Glu Gln Val Val Ala Ile Ala Ser His Asp Gly Gly Lys
        835                 840                 845

Gln Ala Leu Glu Thr Val Gln Arg Leu Leu Pro Val Leu Cys Gln Ala
    850                 855                 860

His Gly Leu Thr Pro Gln Gln Val Val Ala Ile Ala Ser Asn Gly Gly
865                 870                 875                 880

Gly Arg Pro Ala Leu Glu Ser Ile Val Ala Gln Leu Ser Arg Pro Asp
                885                 890                 895

Pro Ala Leu Ala Ala Leu Thr Asn Asp His Leu Val Ala Leu Ala Cys
            900                 905                 910

Leu Gly Gly Arg Pro Ala Leu Asp Ala Val Lys Lys Gly Leu Pro His
        915                 920                 925

Ala Pro Ala Leu Ile Lys Arg Thr Asn Arg Arg Ile Pro Glu Arg Thr
    930                 935                 940

Ser His Arg Val Ala Asp His Ala Gln Val Val Arg Val Leu Gly Phe
945                 950                 955                 960

Phe Gln Cys His Ser His Pro Ala Gln Ala Phe Asp Asp Ala Met Thr
                965                 970                 975

Gln Phe Gly Met Ser Arg His Gly Leu Leu Gln Leu Phe Arg Arg Val
            980                 985                 990

Gly Val Thr Glu Leu Glu Ala Arg  Ser Gly Thr Leu Pro  Pro Ala Ser
        995                 1000                1005

Gln Arg  Trp Asp Arg Ile Leu  Gln Ala Ser Gly Met  Lys Arg Ala
    1010                1015                1020

Lys Pro  Ser Pro Thr Ser Thr  Gln Thr Pro Asp Gln  Ala Ser Leu
    1025                1030                1035

His Ala  Phe Ala Asp Ser Leu  Glu Arg Asp Leu Asp  Ala Pro Ser
    1040                1045                1050

Pro Met  His Glu Gly Asp Gln  Thr Arg Ala Ser Ser  Arg Lys Arg
    1055                1060                1065

Ser Arg  Ser Asp Arg Ala Val  Thr Gly Pro Ser Ala  Gln Gln Ser
```

```
    1070                1075                1080

Phe Glu  Val Arg Val Pro Glu  Gln Arg Asp Ala Leu  His Leu Pro
    1085                1090                1095

Leu Ser  Trp Arg Val Lys Arg  Pro Arg Thr Ser Ile  Gly Gly Gly
    1100                1105                1110

Leu Pro  Asp Pro Gly Thr Pro  Thr Ala Ala Asp Leu  Ala Ala Ser
    1115                1120                1125

Ser Thr  Val Met Arg Glu Gln  Asp Glu Asp Pro Phe  Ala Gly Ala
    1130                1135                1140

Ala Asp  Asp Phe Pro Ala Phe  Asn Glu Glu Glu Leu  Ala Trp Leu
    1145                1150                1155

Met Glu  Leu Leu Pro Gln
    1160
```

<210> SEQ ID NO 111
<211> LENGTH: 1321
<212> TYPE: PRT
<213> ORGANISM: Xanthomonas campestris pv. armoraciae
<220> FEATURE:
<221> NAME/KEY: N-terminus
<222> LOCATION: (1)..(288)
<220> FEATURE:
<221> NAME/KEY: Repeat 1
<222> LOCATION: (289)..(323)
<220> FEATURE:
<221> NAME/KEY: Repeat 2
<222> LOCATION: (324)..(358)
<220> FEATURE:
<221> NAME/KEY: Repeat 3
<222> LOCATION: (359)..(393)
<220> FEATURE:
<221> NAME/KEY: Repeat 4
<222> LOCATION: (394)..(428)
<220> FEATURE:
<221> NAME/KEY: Repeat 5
<222> LOCATION: (429)..(463)
<220> FEATURE:
<221> NAME/KEY: Repeat 6
<222> LOCATION: (464)..(498)
<220> FEATURE:
<221> NAME/KEY: Repeat 7
<222> LOCATION: (499)..(533)
<220> FEATURE:
<221> NAME/KEY: Repeat 8
<222> LOCATION: (534)..(568)
<220> FEATURE:
<221> NAME/KEY: Repeat 9
<222> LOCATION: (569)..(603)
<220> FEATURE:
<221> NAME/KEY: Repeat 10
<222> LOCATION: (604)..(638)
<220> FEATURE:
<221> NAME/KEY: Repeat 11
<222> LOCATION: (639)..(673)
<220> FEATURE:
<221> NAME/KEY: Repeat 12
<222> LOCATION: (674)..(708)
<220> FEATURE:
<221> NAME/KEY: Repeat 13
<222> LOCATION: (709)..(743)
<220> FEATURE:
<221> NAME/KEY: Repeat 14
<222> LOCATION: (744)..(778)
<220> FEATURE:
<221> NAME/KEY: Repeat 15
<222> LOCATION: (779)..(813)
<220> FEATURE:
<221> NAME/KEY: Repeat 16
<222> LOCATION: (814)..(848)
<220> FEATURE:
<221> NAME/KEY: Repeat 17
<222> LOCATION: (849)..(883)

```
<220> FEATURE:
<221> NAME/KEY: Repeat 18
<222> LOCATION: (884)..(918)
<220> FEATURE:
<221> NAME/KEY: Repeat 19
<222> LOCATION: (919)..(953)
<220> FEATURE:
<221> NAME/KEY: Repeat 20
<222> LOCATION: (954)..(988)
<220> FEATURE:
<221> NAME/KEY: Repeat 21
<222> LOCATION: (989)..(1023)
<220> FEATURE:
<221> NAME/KEY: Repeat 21.5
<222> LOCATION: (1024)..(1043)
<220> FEATURE:
<221> NAME/KEY: C-terminus
<222> LOCATION: (1044)..(1321)

<400> SEQUENCE: 111

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
            130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
        260                 265                 270

Glu Ala Val His Ala Trp Arg Asn Ala Leu Thr Gly Ala Pro Leu Asn
    275                 280                 285

Leu Thr Pro Glu Gln Val Val Ala Ile Ala Ser Asn Asn Gly Gly Lys
290                 295                 300

Gln Ala Leu Glu Thr Val Gln Arg Leu Leu Pro Val Leu Cys Gln Ala
```

-continued

```
305                 310                 315                 320
Pro His Asp Leu Thr Pro Glu Gln Val Val Ala Ile Ala Ser Ile Gly
                325                 330                 335

Gly Gly Lys Gln Ala Leu Glu Thr Val Gln Arg Leu Leu Pro Val Leu
                340                 345                 350

Cys Gln Ala Pro His Asp Leu Thr Pro Glu Gln Val Val Ala Ile Ala
                355                 360                 365

Ser Asn Gly Gly Gly Lys Gln Ala Leu Glu Thr Val Gln Arg Leu Leu
370                 375                 380

Pro Val Leu Cys Gln Ala Pro His Cys Leu Thr Pro Glu Gln Val Val
385                 390                 395                 400

Ala Ile Ala Ser Asn Ile Gly Gly Lys Gln Ala Leu Glu Thr Val Gln
                405                 410                 415

Ala Leu Leu Pro Val Leu Cys Gln Ala Pro His Cys Leu Thr Pro Glu
                420                 425                 430

Gln Val Val Ala Ile Ala Ser Asn Gly Gly Gly Lys Gln Ala Leu Glu
                435                 440                 445

Thr Val Gln Arg Leu Leu Pro Val Leu Cys Gln Ala Pro His Asp Leu
        450                 455                 460

Thr Pro Glu Gln Val Val Ala Ile Ala Ser Asn Gly Gly Gly Lys Gln
465                 470                 475                 480

Ala Leu Glu Thr Val Gln Arg Leu Leu Pro Val Leu Cys Gln Ala Pro
                485                 490                 495

His Asp Leu Thr Pro Glu Gln Val Val Ala Ile Ala Ser His Asp Gly
                500                 505                 510

Gly Lys Gln Ala Leu Glu Thr Val Gln Arg Leu Leu Pro Val Leu Cys
        515                 520                 525

Gln Ala Pro His Asp Leu Thr Pro Gln Gln Val Val Ala Ile Ala Ser
        530                 535                 540

Asn Gly Gly Gly Lys Gln Ala Leu Glu Thr Val Gln Arg Leu Leu Pro
545                 550                 555                 560

Val Leu Cys Gln Ala Pro His Asp Leu Thr Pro Glu Gln Val Val Ala
                565                 570                 575

Ile Ala Ser His Asp Gly Gly Lys Gln Ala Leu Glu Thr Val Gln Arg
                580                 585                 590

Leu Leu Pro Val Leu Cys Gln Ala Pro His Asp Leu Thr Pro Glu Gln
                595                 600                 605

Val Val Ala Ile Ala Ser Asn Ile Gly Gly Lys Gln Ala Leu Glu Thr
        610                 615                 620

Val Gln Ala Leu Leu Pro Val Leu Cys Gln Ala Pro His Cys Leu Thr
625                 630                 635                 640

Pro Glu Gln Val Val Ala Ile Ala Ser His Asp Gly Gly Lys Gln Ala
                645                 650                 655

Leu Glu Thr Val Gln Ala Leu Leu Pro Val Leu Cys Gln Ala Pro His
                660                 665                 670

Asp Leu Thr Pro Glu Gln Val Val Ala Ile Ala Ser Asn Ile Gly Gly
        675                 680                 685

Lys Gln Ala Leu Glu Thr Val Gln Arg Leu Leu Pro Val Leu Cys Gln
        690                 695                 700

Ala Pro His Asp Leu Thr Arg Glu Gln Val Val Ala Ile Ala Ser His
705                 710                 715                 720

Asp Gly Gly Lys Gln Ala Leu Glu Thr Val Gln Arg Leu Leu Pro Val
                725                 730                 735
```

```
Leu Cys Gln Ala Pro His Asp Leu Thr Pro Glu Gln Val Val Ala Ile
              740                 745                 750

Ala Ser Asn Gly Gly Gly Lys Gln Ala Leu Glu Thr Val Gln Arg Leu
              755                 760                 765

Leu Pro Val Leu Cys Gln Ala Pro His Asp Leu Thr Pro Glu Gln Val
              770                 775                 780

Val Ala Ile Ala Ser His Asp Gly Gly Lys Gln Ala Leu Glu Thr Val
785                 790                 795                 800

Gln Arg Leu Leu Pro Val Leu Cys Gln Ala Pro His Asp Leu Thr Pro
              805                 810                 815

Glu Gln Val Val Ala Ile Ala Ser Asn Gly Gly Gly Lys Gln Ala Leu
              820                 825                 830

Glu Thr Val Gln Arg Leu Leu Pro Val Leu Cys Gln Ala Pro His Asp
              835                 840                 845

Leu Thr Pro Glu Gln Val Val Ala Ile Ala Ser His Asp Gly Gly Lys
              850                 855                 860

Gln Ala Leu Glu Thr Val Gln Arg Leu Leu Pro Val Leu Cys Gln Ala
865                 870                 875                 880

Pro His Asp Leu Thr Pro Glu Gln Val Val Ala Ile Ala Ser His Asp
              885                 890                 895

Gly Gly Lys Gln Ala Leu Glu Thr Val Gln Arg Leu Leu Pro Val Leu
              900                 905                 910

Cys Gln Ala Pro His Asp Leu Thr Pro Glu Gln Val Val Ala Ile Ala
              915                 920                 925

Ser Asn Gly Gly Gly Lys Gln Ala Leu Glu Thr Val Gln Arg Leu Leu
              930                 935                 940

Pro Val Leu Cys Gln Ala Pro His Asp Leu Thr Pro Glu Gln Val Val
945                 950                 955                 960

Ala Ile Ala Ser Asn Gly Gly Gly Lys Gln Ala Leu Glu Thr Val Gln
              965                 970                 975

Ala Leu Leu Pro Val Leu Cys Gln Ala Pro His Asp Leu Thr Pro Glu
              980                 985                 990

Gln Val Val Ala Ile Ala Ser Asn Ile Gly Gly Lys Gln Ala Leu Glu
              995                1000                1005

Thr Val Gln Arg Leu Leu Pro Val Leu Cys Gln Ala Pro His Asp
              1010                1015                1020

Leu Thr Pro Glu Gln Val Val Ala Ile Ala Ser Asn Gly Gly Gly
              1025                1030                1035

Lys Gln Ala Leu Glu Ser Ile Phe Ala Gln Leu Ser Arg Pro Asp
              1040                1045                1050

Pro Ala Leu Ala Ala Leu Thr Asn Asp Arg Leu Val Ala Leu Ala
              1055                1060                1065

Cys Ile Gly Gly Arg Ser Ala Leu Asn Ala Val Lys Asp Gly Leu
              1070                1075                1080

Pro Asn Ala Leu Thr Leu Ile Arg Arg Ala Asn Ser Arg Ile Pro
              1085                1090                1095

Glu Arg Thr Ser His Leu Val Ala Asp His Thr Gln Val Val Arg
              1100                1105                1110

Val Leu Gly Phe Phe Gln Cys His Ser His Pro Ala Gln Ala Phe
              1115                1120                1125

Asp Glu Ala Met Thr Gln Phe Gly Met Ser Arg His Gly Leu Leu
              1130                1135                1140
```

```
Gln Leu  Phe Arg Arg Val Gly  Val Thr Glu Leu Glu  Ala Arg Ser
    1145                 1150                 1155

Gly Thr  Leu Pro Pro Ala Ser  Gln Arg Trp Asp Arg  Ile Leu Gln
    1160                 1165                 1170

Ala Ser  Gly Met Lys Arg Ala  Lys Pro Ser Pro Thr  Ser Thr Gln
    1175                 1180                 1185

Thr Pro  Asp Gln Ala Ser Leu  His Ala Phe Ala Asp  Ser Leu Glu
    1190                 1195                 1200

Arg Asp  Leu Asp Ala Pro Ser  Pro Met His Glu Gly  Asp Gln Thr
    1205                 1210                 1215

Arg Ala  Ser Ser Arg Lys Arg  Ser Arg Ser Asp Arg  Ala Val Thr
    1220                 1225                 1230

Gly Pro  Ser Ala Gln Gln Ser  Phe Glu Val Arg Val  Pro Glu Gln
    1235                 1240                 1245

Arg Asp  Ala Leu His Leu Pro  Leu Leu Ser Trp Gly  Val Lys Arg
    1250                 1255                 1260

Pro Arg  Thr Arg Ile Gly Gly  Leu Leu Asp Pro Gly  Thr Pro Met
    1265                 1270                 1275

Asp Ala  Asp Leu Val Ala Ser  Ser Thr Val Val Trp  Glu Gln Asp
    1280                 1285                 1290

Ala Asp  Pro Phe Ala Gly Thr  Ala Asp Asp Phe Pro  Ala Phe Asn
    1295                 1300                 1305

Glu Glu  Glu Leu Ala Trp Leu  Met Glu Leu Leu Pro  His
    1310                 1315                 1320
```

<210> SEQ ID NO 112
<211> LENGTH: 960
<212> TYPE: PRT
<213> ORGANISM: Xanthomonas campestris pv. armoraciae
<220> FEATURE:
<221> NAME/KEY: N-terminus
<222> LOCATION: (1)..(288)
<220> FEATURE:
<221> NAME/KEY: Repeat 1
<222> LOCATION: (289)..(322)
<220> FEATURE:
<221> NAME/KEY: Repeat 2
<222> LOCATION: (323)..(356)
<220> FEATURE:
<221> NAME/KEY: Repeat 3
<222> LOCATION: (357)..(390)
<220> FEATURE:
<221> NAME/KEY: Repeat 4
<222> LOCATION: (391)..(424)
<220> FEATURE:
<221> NAME/KEY: Repeat 5
<222> LOCATION: (425)..(458)
<220> FEATURE:
<221> NAME/KEY: Repeat 6
<222> LOCATION: (459)..(492)
<220> FEATURE:
<221> NAME/KEY: Repeat 7
<222> LOCATION: (493)..(526)
<220> FEATURE:
<221> NAME/KEY: Repeat 8
<222> LOCATION: (527)..(560)
<220> FEATURE:
<221> NAME/KEY: Repeat 9
<222> LOCATION: (561)..(594)
<220> FEATURE:
<221> NAME/KEY: Repeat 10
<222> LOCATION: (595)..(628)
<220> FEATURE:
<221> NAME/KEY: Repeat 11
<222> LOCATION: (629)..(662)
<220> FEATURE:
<221> NAME/KEY: Repeat 11.5

```
<222> LOCATION: (663)..(682)
<220> FEATURE:
<221> NAME/KEY: C-terminus
<222> LOCATION: (683)..(960)

<400> SEQUENCE: 112
```

| | | | | | | | | | | | | | | |
|---|---|---|---|---|---|---|---|---|---|---|---|---|---|---|
| Met | Asp | Pro | Ile | Arg | Ser | Arg | Thr | Pro | Ser | Pro | Ala | Arg | Glu | Leu | Leu |
| 1 | | | | 5 | | | | | 10 | | | | | 15 | |

| Ser | Gly | Pro | Gln | Pro | Asp | Gly | Val | Gln | Pro | Thr | Ala | Asp | Arg | Gly | Val |
|---|---|---|---|---|---|---|---|---|---|---|---|---|---|---|---|
| | | | 20 | | | | | 25 | | | | | 30 | | |

| Ser | Pro | Pro | Ala | Gly | Gly | Pro | Leu | Asp | Gly | Leu | Pro | Ala | Arg | Arg | Thr |
|---|---|---|---|---|---|---|---|---|---|---|---|---|---|---|---|
| | | | 35 | | | | | 40 | | | | | 45 | | |

| Met | Ser | Arg | Thr | Arg | Leu | Pro | Ser | Pro | Ala | Pro | Ser | Pro | Ala | Phe |
|---|---|---|---|---|---|---|---|---|---|---|---|---|---|---|
| 50 | | | | | 55 | | | | | 60 | | | | |

| Ser | Ala | Asp | Ser | Phe | Ser | Asp | Leu | Leu | Arg | Gln | Phe | Asp | Pro | Ser | Leu |
|---|---|---|---|---|---|---|---|---|---|---|---|---|---|---|---|
| 65 | | | | | 70 | | | | | 75 | | | | | 80 |

| Phe | Asn | Thr | Ser | Leu | Phe | Asp | Ser | Leu | Pro | Pro | Phe | Gly | Ala | His | His |
|---|---|---|---|---|---|---|---|---|---|---|---|---|---|---|---|
| | | | | 85 | | | | | 90 | | | | | 95 | |

| Thr | Glu | Ala | Ala | Thr | Gly | Glu | Trp | Asp | Glu | Val | Gln | Ser | Gly | Leu | Arg |
|---|---|---|---|---|---|---|---|---|---|---|---|---|---|---|---|
| | | | 100 | | | | | 105 | | | | | 110 | | |

| Ala | Ala | Asp | Ala | Pro | Pro | Thr | Met | Arg | Val | Ala | Val | Thr | Ala | Ala |
|---|---|---|---|---|---|---|---|---|---|---|---|---|---|---|
| | | | 115 | | | | | 120 | | | | | 125 | | |

| Arg | Pro | Pro | Arg | Ala | Lys | Pro | Ala | Pro | Arg | Arg | Ala | Ala | Gln | Pro |
|---|---|---|---|---|---|---|---|---|---|---|---|---|---|---|
| 130 | | | | | 135 | | | | | 140 | | | | |

| Ser | Asp | Ala | Ser | Pro | Ala | Ala | Gln | Val | Asp | Leu | Arg | Thr | Leu | Gly | Tyr |
|---|---|---|---|---|---|---|---|---|---|---|---|---|---|---|---|
| 145 | | | | | 150 | | | | | 155 | | | | | 160 |

| Ser | Gln | Gln | Gln | Gln | Glu | Lys | Ile | Lys | Pro | Lys | Val | Arg | Ser | Thr | Val |
|---|---|---|---|---|---|---|---|---|---|---|---|---|---|---|---|
| | | | | 165 | | | | | 170 | | | | | 175 | |

| Ala | Gln | His | His | Glu | Ala | Leu | Val | Gly | His | Gly | Phe | Thr | His | Ala | His |
|---|---|---|---|---|---|---|---|---|---|---|---|---|---|---|---|
| | | | 180 | | | | | 185 | | | | | 190 | | |

| Ile | Val | Ala | Leu | Ser | Gln | His | Pro | Ala | Ala | Leu | Gly | Thr | Val | Ala | Val |
|---|---|---|---|---|---|---|---|---|---|---|---|---|---|---|---|
| | | | 195 | | | | | 200 | | | | | 205 | | |

| Lys | Tyr | Gln | Asp | Met | Ile | Ala | Ala | Leu | Pro | Glu | Ala | Thr | His | Glu | Ala |
|---|---|---|---|---|---|---|---|---|---|---|---|---|---|---|---|
| | | | 210 | | | | | 215 | | | | | 220 | | |

| Ile | Val | Gly | Val | Gly | Lys | Gln | Trp | Ser | Gly | Ala | Arg | Ala | Leu | Glu | Ala |
|---|---|---|---|---|---|---|---|---|---|---|---|---|---|---|---|
| 225 | | | | | 230 | | | | | 235 | | | | | 240 |

| Leu | Leu | Thr | Val | Ala | Gly | Glu | Leu | Arg | Gly | Pro | Pro | Leu | Gln | Leu | Asp |
|---|---|---|---|---|---|---|---|---|---|---|---|---|---|---|---|
| | | | 245 | | | | | 250 | | | | | 255 | | |

| Thr | Gly | Gln | Leu | Leu | Lys | Ile | Ala | Lys | Arg | Gly | Gly | Val | Thr | Ala | Val |
|---|---|---|---|---|---|---|---|---|---|---|---|---|---|---|---|
| | | | 260 | | | | | 265 | | | | | 270 | | |

| Glu | Ala | Val | His | Ala | Trp | Arg | Asn | Ala | Leu | Thr | Gly | Ala | Pro | Leu | Asn |
|---|---|---|---|---|---|---|---|---|---|---|---|---|---|---|---|
| | | | 275 | | | | | 280 | | | | | 285 | | |

| Leu | Thr | Pro | Glu | Gln | Val | Val | Ala | Ile | Ala | Ser | Asn | Ile | Gly | Gly | Lys |
|---|---|---|---|---|---|---|---|---|---|---|---|---|---|---|---|
| | | | 290 | | | | | 295 | | | | | 300 | | |

| Gln | Ala | Leu | Glu | Thr | Val | Gln | Arg | Leu | Leu | Pro | Val | Leu | Cys | Gln | Ala |
|---|---|---|---|---|---|---|---|---|---|---|---|---|---|---|---|
| 305 | | | | | 310 | | | | | 315 | | | | | 320 |

| His | Gly | Leu | Thr | Pro | Gln | Gln | Val | Val | Ala | Ile | Ala | Ser | His | Asp | Gly |
|---|---|---|---|---|---|---|---|---|---|---|---|---|---|---|---|
| | | | 325 | | | | | 330 | | | | | 335 | | |

| Gly | Lys | Gln | Ala | Leu | Glu | Thr | Val | Gln | Arg | Leu | Leu | Pro | Val | Leu | Cys |
|---|---|---|---|---|---|---|---|---|---|---|---|---|---|---|---|
| | | | 340 | | | | | 345 | | | | | 350 | | |

| Gln | Ala | His | Gly | Leu | Thr | Pro | Glu | Gln | Val | Val | Ala | Ile | Ala | Ser | Asn |
|---|---|---|---|---|---|---|---|---|---|---|---|---|---|---|---|
| | | | 355 | | | | | 360 | | | | | 365 | | |

| Ile | Gly | Gly | Lys | Gln | Ala | Leu | Glu | Thr | Val | Gln | Ala | Leu | Leu | Pro | Val |
|---|---|---|---|---|---|---|---|---|---|---|---|---|---|---|---|
| | | | 370 | | | | | 375 | | | | | 380 | | |

-continued

```
Leu Cys Gln Ala His Gly Leu Thr Pro Glu Gln Val Val Ala Ile Ala
385                 390                 395                 400

Ser His Asp Gly Gly Lys Gln Ala Leu Glu Thr Val Gln Arg Leu Leu
            405                 410                 415

Pro Val Leu Cys Gln Ala His Gly Leu Thr Pro Gln Gln Val Val Ala
                420                 425                 430

Ile Ala Ser His Asp Gly Gly Lys Gln Ala Leu Glu Thr Val Gln Arg
            435                 440                 445

Leu Leu Pro Val Leu Cys Gln Ala His Gly Leu Thr Pro Gln Gln Val
    450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Ala His Gly Leu Thr Pro Gln
                485                 490                 495

Gln Val Val Ala Ile Ala Ser Asn Ser Gly Gly Lys Gln Ala Leu Glu
            500                 505                 510

Thr Val Gln Arg Leu Leu Pro Val Leu Cys Gln Ala His Gly Leu Thr
        515                 520                 525

Pro Gln Gln Val Val Ala Ile Ala Ser Asn Ser Gly Gly Lys Gln Ala
    530                 535                 540

Leu Glu Thr Val Gln Arg Leu Leu Pro Val Leu Cys Gln Ala His Gly
545                 550                 555                 560

Leu Thr Pro Gln Gln Val Val Ala Ile Ala Ser Asn Ser Gly Gly Lys
                565                 570                 575

Gln Ala Leu Glu Thr Val Gln Arg Leu Leu Pro Val Leu Cys Gln Ala
            580                 585                 590

His Gly Leu Thr Pro Glu Gln Val Val Ala Ile Ala Ser His Asp Gly
        595                 600                 605

Gly Lys Gln Ala Leu Glu Thr Val Gln Arg Leu Leu Pro Val Leu Cys
    610                 615                 620

Gln Ala His Gly Leu Thr Pro Glu Gln Val Val Ala Ile Ala Ser Asn
625                 630                 635                 640

Ile Gly Gly Lys Gln Ala Leu Glu Thr Val Gln Arg Leu Leu Pro Val
                645                 650                 655

Leu Cys Gln Ala His Gly Leu Thr Pro Gln Gln Val Val Ala Ile Ala
            660                 665                 670

Ser Asn Gly Gly Gly Arg Pro Ala Leu Glu Ser Ile Val Ala Gln Leu
        675                 680                 685

Ser Arg Pro Asp Pro Ala Leu Ala Ala Leu Thr Asn Asp His Leu Val
    690                 695                 700

Ala Leu Ala Cys Leu Gly Gly Arg Pro Ala Leu Asp Ala Val Lys Lys
705                 710                 715                 720

Gly Leu Pro His Ala Pro Ala Leu Ile Lys Arg Thr Asn Arg Arg Ile
                725                 730                 735

Pro Glu Arg Thr Ser His Arg Val Ala Asp His Ala Gln Val Val Arg
            740                 745                 750

Val Leu Gly Phe Phe Gln Cys His Ser His Pro Ala Gln Ala Phe Asp
        755                 760                 765

Asp Ala Met Thr Gln Phe Gly Met Ser Arg His Gly Leu Leu Gln Leu
    770                 775                 780

Phe Arg Arg Val Gly Val Thr Glu Leu Glu Ala Arg Ser Gly Thr Leu
785                 790                 795                 800

Pro Pro Ala Ser Gln Arg Trp Asp Arg Ile Leu Gln Ala Ser Gly Met
```

-continued

```
                805                 810                 815

Lys Arg Ala Lys Pro Ser Pro Thr Ser Thr Gln Thr Pro Asp Gln Ala
            820                 825                 830

Ser Leu His Ala Phe Ala Asp Ser Leu Glu Arg Asp Leu Asp Ala Pro
        835                 840                 845

Ser Pro Met His Glu Gly Asp Gln Thr Arg Ala Ser Ser Arg Lys Arg
    850                 855                 860

Ser Arg Ser Asp Arg Ala Val Thr Gly Pro Ser Ala Gln Gln Ser Phe
865                 870                 875                 880

Glu Val Arg Val Pro Glu Gln Arg Asp Ala Leu His Leu Pro Leu Leu
                885                 890                 895

Ser Trp Gly Val Lys Arg Pro Arg Thr Arg Ile Gly Gly Leu Leu Asp
            900                 905                 910

Pro Gly Thr Pro Met Asp Ala Asp Leu Val Ala Ser Ser Thr Val Val
        915                 920                 925

Trp Glu Gln Asp Ala Asp Pro Phe Ala Gly Thr Ala Asp Asp Phe Pro
    930                 935                 940

Ala Phe Asn Glu Glu Glu Leu Ala Trp Leu Met Glu Leu Leu Pro Gln
945                 950                 955                 960
```

<210> SEQ ID NO 113
<211> LENGTH: 1062
<212> TYPE: PRT
<213> ORGANISM: Xanthomonas campestris pv. armoraciae
<220> FEATURE:
<221> NAME/KEY: N-terminus
<222> LOCATION: (1)..(288)
<220> FEATURE:
<221> NAME/KEY: Repeat 1
<222> LOCATION: (289)..(322)
<220> FEATURE:
<221> NAME/KEY: Repeat 2
<222> LOCATION: (323)..(356)
<220> FEATURE:
<221> NAME/KEY: Repeat 3
<222> LOCATION: (357)..(390)
<220> FEATURE:
<221> NAME/KEY: Repeat 4
<222> LOCATION: (391)..(424)
<220> FEATURE:
<221> NAME/KEY: Repeat 5
<222> LOCATION: (425)..(458)
<220> FEATURE:
<221> NAME/KEY: Repeat 6
<222> LOCATION: (459)..(492)
<220> FEATURE:
<221> NAME/KEY: Repeat 7
<222> LOCATION: (493)..(526)
<220> FEATURE:
<221> NAME/KEY: Repeat 8
<222> LOCATION: (527)..(560)
<220> FEATURE:
<221> NAME/KEY: Repeat 9
<222> LOCATION: (561)..(594)
<220> FEATURE:
<221> NAME/KEY: Repeat 10
<222> LOCATION: (595)..(628)
<220> FEATURE:
<221> NAME/KEY: Repeat 11
<222> LOCATION: (629)..(662)
<220> FEATURE:
<221> NAME/KEY: Repeat 12
<222> LOCATION: (663)..(696)
<220> FEATURE:
<221> NAME/KEY: Repeat 13
<222> LOCATION: (697)..(730)
<220> FEATURE:
<221> NAME/KEY: Repeat 14
<222> LOCATION: (731)..(764)

```
<220> FEATURE:
<221> NAME/KEY: Repeat 14.5
<222> LOCATION: (765)..(784)
<220> FEATURE:
<221> NAME/KEY: C-terminus
<222> LOCATION: (785)..(1062)

<400> SEQUENCE: 113
```

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

Leu Thr Pro Glu Gln Val Val Ala Ile Ala Ser Asn Ile Gly Gly Lys
    290                 295                 300

Gln Ala Leu Glu Thr Val Gln Ala Leu Leu Pro Val Leu Cys Gln Ala
305                 310                 315                 320

His Gly Leu Thr Pro Gln Gln Val Val Ala Ile Ala Ser His Asp Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser His
        355                 360                 365

Asp Gly Gly Lys Gln Ala Leu Glu Thr Val Gln Arg Leu Leu Pro Val

```
                370            375             380
Leu Cys Gln Ala His Gly Leu Thr Pro Gln Gln Val Ala Ile Ala
385                 390                 395                 400

Ser Asn Gly Gly Gly Lys Gln Ala Leu Glu Thr Val Gln Arg Leu Leu
                405                 410                 415

Pro Val Leu Cys Gln Ala His Gly Leu Thr Pro Glu Gln Val Val Ala
                420                 425                 430

Ile Ala Ser Asn Ser Gly Gly Lys Gln Ala Leu Glu Thr Val Gln Ala
                435                 440                 445

Leu Leu Pro Val Leu Cys Gln Ala His Gly Leu Thr Pro Gln Gln Val
        450                 455                 460

Val Ala Ile Ala Ser Asn Ser Gly Gly Lys Gln Ala Leu Glu Thr Val
465                 470                 475                 480

Gln Ala Leu Leu Pro Val Leu Cys Gln Ala His Gly Leu Thr Pro Glu
                    485                 490                 495

Gln Val Val Ala Ile Ala Ser Asn Ile Gly Gly Lys Gln Ala Leu Glu
                500                 505                 510

Thr Val Gln Arg Leu Leu Pro Val Leu Cys Gln Ala His Gly Leu Thr
            515                 520                 525

Pro Gln Gln Val Val Ala Ile Ala Ser His Asp Gly Gly Lys Gln Ala
        530                 535                 540

Leu Glu Thr Val Gln Arg Leu Leu Pro Val Leu Cys Gln Ala His Gly
545                 550                 555                 560

Leu Thr Pro Gln Gln Val Val Ala Ile Ala Ser Asn Gly Gly Gly Lys
                565                 570                 575

Gln Ala Leu Glu Thr Val Gln Arg Leu Leu Pro Val Leu Cys Gln Ala
                580                 585                 590

His Gly Leu Thr Pro Glu Gln Val Val Ala Ile Ala Ser Asn Ile Gly
                595                 600                 605

Gly Lys Gln Ala Leu Glu Thr Val Gln Ala Leu Leu Pro Val Leu Cys
        610                 615                 620

Gln Ala His Gly Leu Thr Pro Gln Gln Val Val Ala Ile Ala Ser Asn
625                 630                 635                 640

Ser Gly Gly Lys Gln Ala Leu Glu Thr Val Gln Ala Leu Leu Pro Val
                645                 650                 655

Leu Cys Gln Ala His Gly Leu Thr Pro Glu Gln Val Val Ala Ile Ala
                660                 665                 670

Ser Asn Ile Gly Gly Lys Gln Ala Leu Glu Thr Val Gln Arg Leu Leu
                675                 680                 685

Pro Val Leu Cys Gln Ala His Gly Leu Thr Pro Glu Gln Val Val Ala
        690                 695                 700

Ile Ala Ser Asn Gly Gly Lys Gln Ala Leu Glu Thr Val Gln Arg
705                 710                 715                 720

Leu Leu Pro Val Leu Cys Gln Ala His Gly Leu Thr Pro Glu Gln Val
                725                 730                 735

Val Ala Ile Ala Ser Asn Ile Gly Gly Lys Gln Ala Leu Glu Thr Val
                740                 745                 750

Gln Ala Leu Leu Pro Val Leu Cys Gln Ala His Gly Leu Thr Pro Glu
                755                 760                 765

Gln Val Val Ala Ile Ala Ser Asn Gly Gly Gly Arg Pro Ala Leu Glu
                770                 775                 780

Ser Ile Val Ala Gln Leu Ser Arg Pro Asp Pro Ala Leu Ala Ala Leu
785                 790                 795                 800
```

Thr Asn Asp His Leu Val Ala Leu Ala Cys Leu Gly Arg Pro Ala
            805                 810                 815

Leu Asp Ala Val Lys Lys Gly Leu Pro His Ala Pro Ala Leu Ile Lys
            820                 825                 830

Arg Thr Asn Arg Arg Ile Pro Glu Arg Thr Ser His Arg Val Ala Asp
            835                 840                 845

His Ala Gln Val Val Arg Val Leu Gly Phe Phe Gln Cys His Ser His
            850                 855                 860

Pro Ala Gln Ala Phe Asp Asp Ala Met Thr Gln Phe Gly Met Ser Arg
865                 870                 875                 880

His Gly Leu Leu Gln Leu Phe Arg Arg Val Gly Val Thr Glu Leu Glu
            885                 890                 895

Ala Arg Ser Gly Thr Leu Pro Pro Ala Ser Gln Arg Trp Asp Arg Ile
            900                 905                 910

Leu Gln Ala Ser Gly Met Lys Arg Ala Lys Pro Ser Pro Thr Ser Thr
            915                 920                 925

Gln Thr Pro Asp Gln Ala Ser Leu His Ala Phe Ala Asp Ser Leu Glu
            930                 935                 940

Arg Asp Leu Asp Ala Pro Ser Pro Met His Glu Gly Asp Gln Thr Arg
945                 950                 955                 960

Ala Ser Ser Arg Lys Arg Ser Arg Ser Asp Arg Ala Val Thr Gly Pro
            965                 970                 975

Ser Ala Gln Gln Ser Phe Glu Val Arg Val Pro Glu Gln Arg Asp Ala
            980                 985                 990

Leu His Leu Pro Leu Ser Trp Arg Val Lys Arg Pro Arg Thr Ser Ile
            995                 1000                1005

Gly Gly Gly Leu Pro Asp Pro Gly Thr Pro Thr Ala Ala Asp Leu
            1010                1015                1020

Ala Ala Ser Ser Thr Val Met Arg Glu Gln Asp Glu Asp Pro Phe
            1025                1030                1035

Ala Gly Ala Ala Asp Asp Phe Pro Ala Phe Asn Glu Glu Glu Leu
            1040                1045                1050

Ala Trp Leu Met Glu Leu Leu Pro Gln
            1055                1060

<210> SEQ ID NO 114
<211> LENGTH: 13
<212> TYPE: DNA
<213> ORGANISM: Artificial Sequence
<220> FEATURE:
<223> OTHER INFORMATION: ARTBs4 box

<400> SEQUENCE: 114
ttgtatataa ctt                                                      13

<210> SEQ ID NO 115
<211> LENGTH: 13
<212> TYPE: DNA
<213> ORGANISM: Artificial Sequence
<220> FEATURE:
<223> OTHER INFORMATION: Hax3 target Poly-A box

<400> SEQUENCE: 115
tacacccaaa aaa                                                      13

<210> SEQ ID NO 116
<211> LENGTH: 13

```
<212> TYPE: DNA
<213> ORGANISM: Artificial Sequence
<220> FEATURE:
<223> OTHER INFORMATION: Hax3 target Poly-C box

<400> SEQUENCE: 116 tacaccccccc ccc                                                        13

<210> SEQ ID NO 117
<211> LENGTH: 13
<212> TYPE: DNA
<213> ORGANISM: Artificial Sequence
<220> FEATURE:
<223> OTHER INFORMATION: Hax3 target Poly-G box

<400> SEQUENCE: 117
tacacccggg ggg                                                         13

<210> SEQ ID NO 118
<211> LENGTH: 13
<212> TYPE: DNA
<213> ORGANISM: Artificial Sequence
<220> FEATURE:
<223> OTHER INFORMATION: Hax3 target Poly-T box

<400> SEQUENCE: 118 tacaccctttt ttt                                                        13

<210> SEQ ID NO 119
<211> LENGTH: 34
<212> TYPE: PRT
<213> ORGANISM: Artificial Sequence
<220> FEATURE:
<223> OTHER INFORMATION: Consensus sequence

<400> SEQUENCE: 119

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 120
<211> LENGTH: 35
<212> TYPE: PRT
<213> ORGANISM: Artificial Sequence
<220> FEATURE:
<223> OTHER INFORMATION: Consensus sequence

<400> SEQUENCE: 120

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

Pro His Asp
        35
```